United States Patent
Lam et al.

(10) Patent No.: US 11,833,251 B2
(45) Date of Patent: Dec. 5, 2023

(54) PHARMACEUTICAL METHODS AND COMPOSITIONS

(71) Applicant: THE UNIVERSITY OF SUSSEX, Sussex (GB)

(72) Inventors: Matthew Lam, Sussex (GB); Ali Nokhodchi, Sussex (GB)

(73) Assignee: THE UNIVERSITY OF SUSSEX, Sussex (GB)

( * ) Notice: Subject to any disclaimer, the term of this patent is extended or adjusted under 35 U.S.C. 154(b) by 47 days.

(21) Appl. No.: 17/262,572

(22) PCT Filed: Jul. 24, 2019

(86) PCT No.: PCT/GB2019/052065
§ 371 (c)(1),
(2) Date: Jan. 22, 2021

(87) PCT Pub. No.: WO2020/021254
PCT Pub. Date: Jan. 30, 2020

(65) Prior Publication Data
US 2021/0299054 A1    Sep. 30, 2021

(30) Foreign Application Priority Data

Jul. 24, 2018  (GB) .................................... 1812022

(51) Int. Cl.
*A61K 9/20* (2006.01)
*A61K 9/16* (2006.01)
*A61K 45/06* (2006.01)

(52) U.S. Cl.
CPC .............. *A61K 9/2095* (2013.01); *A61K 9/16* (2013.01); *A61K 9/2009* (2013.01); *A61K 9/2054* (2013.01); *A61K 45/06* (2013.01)

(58) Field of Classification Search
None
See application file for complete search history.

(56) References Cited

U.S. PATENT DOCUMENTS 6,096,337 A    8/2000  Spireas et al.
7,569,612 B1 *  8/2009  Arnold ................. A61K 9/2018
                                                    514/687

FOREIGN PATENT DOCUMENTS

| BR | 102016015553 A2 | 1/2018 |
| CN | 1121337 A | 6/1990 |
| EP | 3 335 699 A1 | 6/2018 |
| WO | 97/47290 A1 | 12/1997 |
| WO | 2018109158 A1 | 6/2018 |

OTHER PUBLICATIONS

English translation of BR102016015553A2 (2022).*
International Search Report for PCT/GB2019/052065 dated Oct. 1, 2019.
Written Opinion of the International Searching Authority for PCT/GB2019/052065 dated Oct. 1, 2019.
Search Report under Section 17(5) for Application No. GB1812022.0 dated Feb. 6, 2019 (6 pages).
Pezzini et al., "Liquisolid technology applied to pellets: Evaluation of the feasibility and dissolution performance using felodipine as a model drug", Chemical Engineering Research and Design, 110:62-69 (2016).
Bhavsar et al., "Enhancement of aqueous solubility of carvedilol by liquisolid technique", Indo American Journal of Pharmaceutical Research, pp. 537-549 (2017).
Krupa et al., "Preparation of solid self-emulsifying drug delivery systems using magnesium aluminometasilicates and fluid-bed coating process", Powder Technology, 266:329-339 (2014).

* cited by examiner

*Primary Examiner* — Patricia Duffy
*Assistant Examiner* — Garen Gotfredson
(74) *Attorney, Agent, or Firm* — Rodney J. Fuller; BOOTH UDALL FULLER, PLC

(57) ABSTRACT

The disclosure provides a method of producing a pharmaceutical composition. The method comprises (a) dissolving an active pharmaceutical ingredient (API) in a liquid vehicle to form a liquid medicament; (b) contacting the liquid medicament with a pharmaceutical carrier; (c) contacting the composition comprising the liquid medicament and pharmaceutical carrier with a pharmaceutical coating material to form a liqui-mass composition; and (d) pelletising the liqui-mass composition to form the pharmaceutical composition.

21 Claims, 17 Drawing Sheets

A

B

C

D

E

F

G

PHARMACEUTICAL METHODS AND COMPOSITIONS

This application is the U.S. National Stage of International Application No. PCT/GB2019/052065, filed Jul. 24, 2019, which claims the benefit of and priority to Great Britain Application No. 1812022.0, filed Jul. 24, 2018, the contents of each of which are incorporated herein by reference in their entireties.

The present disclosure relates to pharmaceutical compositions, and methods of producing the same. In particular embodiments, the disclosure is concerned with the invented pharmaceutical dosage form called liqui-pellet and liqui-tablet, comprising a poorly water soluble or water-insoluble active pharmaceutical ingredient (API).

Around 60% of active pharmaceutical ingredients (APIs) in the market and 40% APIs in development stage are poorly water-soluble. This poor water solubility means that the API cannot be dissolved efficiently in an aqueous environment, such as in the stomach, leading to poor bioavailability. To overcome this problem, pharmaceutical companies may try to apply various technologies, which can be categorized into chemical or physical modifications. These technologies include conversion of crystalline API into amorphous state, nanosuspension, co-grinding, micronization, self-emulsifying drug delivery system, solid dispersion and so forth. Despite these various technologies available, they may require advance preparation technique, sophisticated machinery, complicated technology or may not be cost effective. A simpler approach that a pharmaceutical company may take to improve the drug efficacy is to increase the amount of API which is administered. However, this increases the risk of side effects as well as the production cost of the pharmaceutical product.

Liquisolid technology is considered as a promising technology to overcome poor bioavailability of APIs whilst being simple and cost effective to produce. In this technology, an API is incorporated into a suitable non-volatile solvent, i.e. a liquid which the API is soluble in, to give a liquid medication. The liquid medication is then incorporated into a carrier (a material that holds the liquid medication) and a coating material (usually but not always nano-sized silicone dioxide) to make a free-flowing and dry looking powder admixture, called a liquisolid system. This admixture can then be filled into a capsule or compressed into a tablet, which is commonly termed liquisolid compact.

Liquisolid technology improves bioavailability because the API, or a fraction of the API, is already in a liquid state, and so does not need to be dissolved in an aqueous environment. For poorly water/water insoluble APIs, more often than not, the dissolution rate is the limiting step of the bioavailability. The liquisolid formulation's primary mechanism of enhanced drug dissolution rate is postulated to be mainly due to the increase in surface area available for dissolution, increase solubility of API and improved wettability of drug particles. Furthermore, liquisolid formulations hold key advantages over other technologies because they are cost effective, simple to manufacture and more often than not use green technology.

However, there are major problems inherent to the liquisolid formulation. In particular, the liquid and powder admixture has poor flow properties, which makes manufacture of the product challenging, due to difficulties in attaining uniform feed and reproducible filling for tablet and capsule production. This led to the Spireas mathematical equation being developed, this is used to determine the amount of carrier and coating material that can be used to achieve acceptable flow properties.

In particular, the flow properties can be improved by increasing the amount of the carrier and possibly coating material used, but this means that the liquisolid system cannot be used to deliver high dosages of API as the tablet or capsule produced would be too large. Furthermore, the admixture displays poor compressibility, preventing the production of a tablet.

The present invention arises from the inventors' work in attempting to overcome the problems associated with the prior art.

In accordance with a first aspect of the invention, there is provided a method of producing a pharmaceutical composition, the method comprising:

dissolving an active pharmaceutical ingredient (API) in a liquid vehicle to form a liquid medicament;

contacting the liquid medicament with a pharmaceutical carrier;

contacting the composition comprising the liquid medicament and pharmaceutical carrier with a pharmaceutical coating material to form a liqui-mass composition; and pelletising the liqui-mass composition to form the pharmaceutical composition.

The composition produced using the above method may be known as a liqui-pellet composition. Liqui-pellet compositions provide the potential to combine incompatible drugs or drugs with different release profiles in the same dose unit. They also reduce the risk of side effects due to dose dumping.

Advantageously, liqui-pellet compositions can have a high liquid load factor, high concentrations of liquid medication, and/or contain large amounts of a liquid vehicle whilst typically achieving excellent or good flow properties. Accordingly, the Spireas liquisolid mathematical equations are no longer required. Even without using this equation, the formulation easy to handle and produce commercially, this is reflected by almost no issue with flow properties in all examples.

Liqui-pellet compositions are also able to provide a high dose dosage form (i.e. API of 100 mg or more) whilst maintaining the weight and size of dosage form with acceptable limits suitable for swallowing (as shown in examples 10 to 12). In addition, liqui-pellet compositions exhibit the capability for remarkably rapid dissolution rate (as shown in examples 6, 8 and 9). This is due to higher potential of API being solubilized in the liquid vehicle and the potential of incorporation of additional functional excipients to assist dissolution rate without making the dosage form too bulky for swallowing (as shown in examples 5, 6, 8, 9 and 10).

Furthermore, the liqui-pellet composition may be manufactured using a simple method, as described above. Advance preparation and complex machinery are not required. The method is cost effective and allows versatile formulation modification (i.e. application of coating and functional excipients). It can be used with green technology. Furthermore, the method has the potential for scale-up of production.

Finally, the excipients used are usually common and easily obtainable.

Pelletising the liqui-mass composition may comprise using an extrusion-spheronisation technique. Accordingly, pelletising the liqui-mass may comprise:

extruding the liqui-mass through an extruder to form a cylinder-shaped extrudate; and spheronising the extrudate to cause it to break up and form pellets.

The extruder may be an axial screw feed extruder.

The extruder may comprise openings with a diameter between 0.001 mm and 10 mm, more preferably between 0.01 mm and 5 mm or between 0.1 mm and 2 mm, most preferably between 0.5 mm and 1.5 mm.

The spheronisation speed is preferably at least 500 rpm, more preferably at least 1000 rpm and most preferably at least 1500 rpm. The spheronisation speed is preferably less than 5000 rpm, more preferably less than 4500 rpm, and most preferably less than 400 rpm. The spheronisation speed is preferably between 500 and 5000 rpm, more preferably between 1000 and 4500 rpm and most preferably between 1500 and 4000 rpm.

Preferably, the pharmaceutical composition comprises pellets or granules with an average diameter of between 10 µm and 5000 µm, more preferably between 100 µm and 4000 µm or between 250 µm and 3000 µm and most preferably between 500 µm and 2000 µm.

It may be appreciated that the weight ratio of the liquid medicament to the carrier can be expressed by defining a liquid load factor, which is the weight of the liquid medication, i.e. the liquid vehicle comprising the API, divided by the weight of the carrier powder. Preferably, the liquid load factor is at least 0.5, more preferably at least 0.75, at least 1 or at least 1.25, and most preferably at least 1.4, at least 1.5 or at least 1.6.

The inventors believe that compositions with a high liquid load factor are novel and inventive per se.

Accordingly, in accordance with a second aspect, there is provided a method of producing a pharmaceutical composition, the method comprising:

dissolving an active pharmaceutical ingredient (API) in a liquid vehicle to form a liquid medicament;

contacting the liquid medicament with a pharmaceutical carrier comprising a material with a large Brunauer-Emmett-Teller (BET) specific surface area such that the liquid load factor of the resultant composition is at least 1; and contacting the composition comprising the liquid medicament and pharmaceutical carrier with a pharmaceutical coating to form a free flowing liqui-mass composition.

The free-flowing composition can be compressed into a tablet, filled into a capsule or extruded and spheronized to form pellets. The inventors believe that the free-flowing composition being able to be extruded without additional applied force is novel.

Preferably, the liquid load factor is at least 0.5, more preferably at least 0.75, at least 1 or at least 1.25, and most preferably at least 1.4, at least 1.5 or at least 1.6.

The API may be a water-insoluble API. A water-insoluble API may be an API which falls within class II or class IV of the Biopharmaceuticals Classification System (BCS). Alternatively or additionally, a water-insoluble API may be an API where 1 part of the drug is insoluble in less than 10 parts deionised water at room temperature, more preferably 1 part of the drug is insoluble in less than 100 parts deionised water at room temperature, in less than 500 parts deionised water at room temperature or in less than 1,000 parts deionised water at room temperature, and most preferably 1 part of the drug is insoluble in less than 5,000 parts deionised water at room temperature or in less than 10,000 parts deionised water at room temperature.

The API may comprise naproxen, hydrochlorothiazide, ketoprofen, griseofulvin, curcumin, ibuprofen, candesartan cilexetil, furosemide, valsartan, indomethacin, piroxicam, famotidine and/or clonazepam.

Preferably, the amount of the API used is sufficient to cause the liqui-mass composition to comprise at least 1 wt % API, more preferably at least 2 wt % or at least 3 wt % API, and most preferably at least 4 wt % API or at least 5 wt % API. Preferably, the amount of the API used is sufficient to cause the liqui-mass composition to comprise less than 60 wt % API, more preferably less than 50 wt % or less than 35 wt % API, and most preferably less than 25 wt % API or less than 20 wt % API. Preferably, the amount of the API used is sufficient to cause the liqui-mass composition to comprise between 1 wt % and 60 wt % API, more preferably between 2 wt % and 50 wt % or between 3 wt % and 35 wt % API, and most preferably between 4 wt % and 25 wt % API or between 5 wt % and 20 wt % API.

Preferably, the liquid vehicle comprises an organic solvent. Preferably, the organic solvent is a non-toxic, non-volatile organic solvent. It may be appreciated that the skilled person could select a suitable liquid vehicle for a specific API using a saturation solubility test.

The liquid vehicle may comprise at least one of a polyethylene glycol (PEG), a propylene glycol (PG), a polysorbate, a carboxylic acid, a mono-, di- and/or triglyceride, and/or an organic compound comprising a hydroxyl group, a carboxyl group and/or an ester group. The liquid vehicle may comprise kolliphor EL, labrafil, labrasol and/or span 80. The PEG may have an average molecular weight between 50 g/mol and 1000 g/mol, more preferably between 75 g/mol and 750 g/mol or between 100 g/mol and 500 g/mol, and most preferably between 150 g/mol and 250 g/mol or between 175 g/mol and 225 g/mol. The polysorbate may have an average molecular weight between 200 g/mol and 10,000 g/mol, more preferably between 500 g/mol and 5,000 g/mol or between 750 g/mol and 2,500 g/mol and most preferably between 1,000 g/mol and 1,500 g/mol.

The organic compound may have general formula (I):

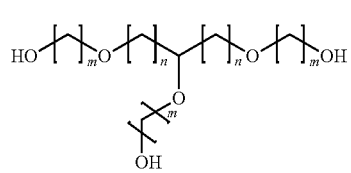

Formula (I)

where each n is independently an integer between 1 and 10; and each m is independently an integer between 1 and 10.

Preferably, each n is 1 and each m is 2. The carboxylic acid may comprise a $C_1$ to $C_{50}$ carboxylic acid, more preferably a $C_5$ to $C_{30}$ or a $C_{10}$ to $C_{25}$ carboxylic acid, and most preferably a $C_{15}$ to $C_{20}$ carboxylic acid. The carboxylic acid may comprise at least one of decanoic acid, undecanoic acid, dodecanoic acid, tridecanoic acid, tetradecanoic acid, pentadecanooic acid, hexadecanoic acid, heptadecanoic acid, octadecanoic acid, nonadecanoic acid or eicosanoic acid. The ester may comprise a mono- or di-ester.

The ester may comprise a $C_1$ to $C_{50}$ ester, more preferably a $C_2$ to $C_{30}$ or a $C_3$ to $C_{25}$ ester, and most preferably a $C_5$ to $C_{20}$ ester.

In some embodiments, the liquid vehicle may comprise a combination of a compound of formula (I) and a carboxylic acid. For instance, the liquid vehicle may comprise a compound of formula (I) where n is 1 and m is 2, hexadecanoic acid and octadecanoic acid, as sold under the brand name Labrafil®. Alternatively, the liquid vehicle may comprise a combination of a mono-, di- and/or triglyceride, a PEG and an ester as sold under the brand name Labrasol®.

It may be appreciated that the weight ratio of the API to the liquid vehicle may vary depending upon the liquid vehicle and the API which are used. Key factors which contribute to determining this weight ratio include:
a) the solubility of the API in the liquid vehicle;
b) the physicochemical properties of the formulation;
c) the size & weight of the final dosage form; and/or
d) on the desired drug dissolution rate.

A low amount of the API compared to the liquid vehicle would lead to a higher dissolution rate but a larger dosage form. Alternatively, a large amount of the API compared to the liquid vehicle would reduce the size of the dosage form but would also have a slower dissolution rate. Accordingly, the properties can be tweaked for a given application.

In one embodiment, the weight ratio of the API to the liquid vehicle may be between 1:20 and 10:1. In one embodiment, the weight ratio of the API to the liquid vehicle is between 1:10 and 10:5, or between 1:5 and 6:5, and most preferably the weight ratio of the API to the liquid vehicle is between 1:4 and 4:3, between 1:3 and 1:1 or between 1:2 and 2:3.

Preferably, the amount of the liquid vehicle used is sufficient to cause the liqui-mass composition to comprise at least 5 wt % liquid vehicle, more preferably at least 10 wt % or at least 15 wt % liquid vehicle, and most preferably at least 20 wt % liquid vehicle.

Preferably, the amount of the liquid vehicle used is sufficient to cause the liqui-mass composition to comprise less than 50 wt % liquid vehicle, more preferably less than 45 wt % or less than 40 wt % liquid vehicle, and most preferably less than 35 wt % liquid vehicle. Preferably, the amount of the liquid vehicle used is sufficient to cause the liqui-mass composition to comprise between 5 wt % and 50 wt % liquid vehicle, more preferably between 10 wt % and 45 wt % or between 15 wt % and 40 wt % liquid vehicle, and most preferably between 20 wt % and 35 wt % liquid vehicle.

The method may comprise contacting the liquid medicament, the composition comprising the liquid medicament and pharmaceutical carrier, the liqui-mass composition and/or the pelletised liquid-mass composition with an additional excipient.

Accordingly, the method may comprise dissolving an additional excipient into the liquid vehicle. The additional excipient may be dissolved in the liquid vehicle before, after or simultaneously to dissolving the API in the liquid vehicle. Preferably, the additional excipient is dissolved in the liquid vehicle prior to contacting the liquid medicament with a pharmaceutical carrier. Accordingly, the liquid medicament may comprise the additional excipient.

Additionally, or alternatively, prior to contacting the composition comprising the liquid medicament and pharmaceutical carrier with a pharmaceutical coating, the method comprises contacting the composition comprising the liquid medicament and pharmaceutical carrier with an additional excipient.

Additionally, or alternatively, subsequent to contacting the composition comprising the liquid medicament and pharmaceutical carrier with a pharmaceutical coating, the method comprises contacting the liqui-mass composition with an additional excipient.

The one or more additional excipient may be configured to:
a) promoting disintegration;
b) modulate pH to enhance or reduce solubility;
c) increase saturation solubility;
d) creating a floating system;
e) creating a eutectic system;
f) retard drug release; and/or
g) reduce tackiness.

Accordingly, the method may comprise:
dissolving an active pharmaceutical ingredient (API), and optionally an additional excipient, in a liquid vehicle to form a liquid medicament;
contacting the liquid medicament with a pharmaceutical carrier;
optionally contacting the composition comprising the liquid medicament and pharmaceutical carrier with an additional excipient;
contacting the composition comprising the liquid medicament, pharmaceutical carrier and at least one additional excipient with a pharmaceutical coating to form a liqui-mass composition; and
pelletising the liqui-mass composition to form the pharmaceutical composition.

The additional excipient may be configured to increase the saturation limit of the API in the liquid vehicle. Preferably, the method comprises dissolving the additional excipient in the liquid vehicle. The additional excipient may comprise polyvinylpyrrolidone (PVP). Advantageously, PVP inhibits crystal growth, thereby allowing a higher supersaturation limit.

Preferably, the amount of the additional excipient configured to increase the saturation limit used is sufficient to cause the liqui-mass composition to comprise at least 5 wt % additional excipient, more preferably at least 10 wt % or at least 20 wt % additional excipient, and most preferably at least 25 wt % additional excipient. Preferably, the amount of the additional excipient configured to increase the saturation limit used is sufficient to cause the liqui-mass composition to comprise less than 60 wt % additional excipient, more preferably less than 50 wt % or less than 40 wt % additional excipient, and most preferably less than 35 wt % additional excipient. Preferably, the amount of the additional excipient configured to increase the saturation limit used is sufficient to cause the liqui-mass composition to comprise between 5 and 60 wt % additional excipient, more preferably between 10 and 50 wt % or between 20 and 40 wt % additional excipient, and most preferably between 25 and 35 wt % additional excipient.

The additional excipient may comprise a disintegrant. Advantageously, a disintegrant increases the release rate of the API. The disintegrant may comprise alginate, chitin, chitosan, or a pharmaceutically acceptable salt thereof. The disintegrant may comprise a starch- or ceullulose-based excipient, or a pharmaceutically acceptable salt thereof, such as corn starch, partially pregelatinized starch, microcrystalline cellulose, and low-substituted hydroxypropyl cellulose. However, the disintegrant is preferably a superdisintegrant. The superdisintegrant may comprise starch glycolate, polyvinylpolypyrrolidone (PVPP), croscarmellose, chitin-silica, chitosan-silica, indion 414, mucilage of *Plantago* ovate, or a pharmaceutically acceptable salt thereof. The salt may comprise a sodium salt. Accordingly, the disintegrant or superdisintegrant may comprise sodium starch glycolate, croscarmellose sodium or sodium alginate. The method may comprise contacting the liquid medicament and/or the composition comprising the liquid medicament and pharmaceutical carrier with the disintegrant. Preferably, the amount of disintegrant used is sufficient to cause the liqui-mass composition to comprise at least 1 wt % disintegrant, more preferably at least 1.5 wt % or at least 2 wt % disintegrant, and most preferably at least 2.5 wt % disintegrant. Preferably, the amount of disintegrant used is sufficient to cause the liqui-mass composition to comprise less than 15 wt % disintegrant, more preferably less than 10 wt % or less than 8 wt % disintegrant, and most preferably less than 7 wt % disintegrant. Preferably, the amount of disintegrant used is sufficient to cause the liqui-mass composition to comprise between 1 wt % and 15 wt % disintegrant, more preferably between 1.5 wt % and 10 wt % or between 2 wt % and 8 wt % disintegrant, and most preferably between 2.5 wt % and 7 wt % disintegrant.

The additional excipient may comprise an effervescent agent. Advantageously, an effervescent increases the release rate of the API. Preferably, the method comprises contacting the composition comprising the liquid medicament and pharmaceutical carrier with the additional excipient. The effervescent agent may comprise a carbonate or bicarbonate, preferably an alkali metal carbonate or alkali metal bicarbonate, and most preferably a sodium bicarbonate. Preferably, the amount of effervescent used is sufficient to cause the liqui-mass composition to comprise at least 1 wt % effervescent, more preferably at least 5 wt %, at least 10 wt % or at least 15 wt % effervescent, and most preferably at least 20 wt % or at least 25 wt % effervescent. Preferably, the amount of effervescent used is sufficient to cause the liqui-mass composition to comprise less than 60 wt % effervescent, more preferably less than 50 wt %, less than 45 wt % or less than 40 wt % effervescent, and most preferably less than 35 wt % or less than 30 wt % effervescent. Preferably, the amount of effervescent used is sufficient to cause the liqui-mass composition to comprise between 1 wt % and 60 wt % effervescent, more preferably between 5 wt % and 50 wt %, between 10 wt % and 45 wt % or between 15 wt % and 40 wt % effervescent, and most preferably between 20 wt % and 35 wt % or between 25 wt % and 30 wt % effervescent.

Preferably, in embodiments where the one or more additional excipient comprises an effervescent, the one or more additional excipient does not further comprise a retarding agent.

The additional excipient may comprise a pH modulating agent. The pH modulating agent may be configured to raise the pH of the liqui-mass composition. For instance, sodium bicarbonate would increase the pH of the liqui-mass. Accordingly, the effervescent agent may also be the pH modulating agent. Advantageously, the solubility of a weakly acidic increases in a more alkaline environment.

The additional excipient may comprise a retarding agent. The retarding agent may be used in composition when the API is a water soluble API. The retarding agent may be a polymer configured to sustainably release the API. For instance, the polymer may be a polymer based on a cellulose. For instance, the polymer may be hydroxypropyl methylcellulose (HPMC) or ethyl cellulose. The polymer may be a copolymer configured to sustainably release the API. The copolymer may be a copolymer of ethyl acrylate, methyl methacrylate and/or trimethylammonioethyl methacrylate chloride.

Preferably, the copolymer is a copolymer of ethyl acrylate, methyl methacrylate and trimethylammonioethyl methacrylate chloride. The molar ratio of ethyl acrylate to methyl methacrylate may be between 1:100 and 100:1, more preferably between 1:10 and 10:1 or between 1:5 and 5:1, and most preferably between 1:3 and 1:1 or between 1:2.5 and 1:1.5. The molar ratio of ethyl acrylate to trimethylammonioethyl methacrylate chloride may be between 1:0.001 and 1:10, more preferably between 1:0.01 and 1:5 or between 1:0.05 and 1:1, and most preferably between 1:0.06 and 1:0.5, between 1:0.08 and 1:0.5 or between 1:0.09 and 1:1.2. Accordingly, the copolymer may by a copolymer sold under the brand name Eudragit®, optionally Eudragit® RS PO.

Preferably, the amount of the retarding agent used is sufficient to cause the liqui-mass composition to comprise at least 1 wt % retarding agent, more preferably at least 5 wt %, at least 10 wt % or at least 20 wt % retarding agent, and most preferably at least 30 wt % or at least 35 wt % retarding agent. Preferably, the amount of retarding agent used is sufficient to cause the liqui-mass composition to comprise less than 90 wt % retarding agent, more preferably less than 80 wt %, less than 70 wt % or less than 60 wt % retarding agent, and most preferably less than 50 wt % or less than 40 wt % retarding agent. Preferably, the amount of retarding agent used is sufficient to cause the liqui-mass composition to comprise between 1 wt % and 90 wt % retarding agent, more preferably between 5 wt % and 80 wt %, between 10 wt % and 70 wt % or between 20 wt % and 60 wt % retarding agent, and most preferably between 30 wt % and 50 wt % or between 35 wt % and 40 wt % retarding agent.

The additional excipient may comprise an anti-tack agent. The anti-tack agent may comprise or consist of a stearate (e.g. magnesium stearate), a silicate (e.g. magnesium silicate), microcrystalline cellulose (MCC), hydroxypropyl methylcellulose (HPMC), simeticon and/or fumed silica. The anti-tack agent may be hydrophilic or hydrophobic. For instance, magnesium stearate is hydrophobic and fumed silica is hydrophilic. It may be appreciated that a hydrophobic anti-tack agent will be more suitable for slow release and a hydrophilic anti-tack agent will be more suited for fast release. Preferably, the fumed silica has a BET surface area of between 50 and 500 $m^2/g$, more preferably between 100 and 400 $m^2/g$ or between 150 and 300 $m^2/g$, and most preferably between 175 and 250 $m^2/g$ or between 190 and 225 $m^2/g$.

Preferably, the amount of the anti-tack agent used is sufficient to cause the liqui-mass composition to comprise at least 0.1 wt % anti-tack agent, more preferably at least 0.2 wt %, at least 0.4 wt % or at least 0.5 wt % anti-tack agent. In embodiments where the anti-tack agent is hydrophilic, the amount of the anti-tack agent used may be sufficient to cause the liqui-mass composition to comprise at least 0.75 wt % anti-tack agent, more preferably at least 1 wt % or at least 1.1 wt % anti-tack agent.

Preferably, the amount of anti-tack agent used is sufficient to cause the liqui-mass composition to comprise less than 10 wt % anti-tack agent, more preferably less than 5 wt %, less than 2 wt % or less than 1.5 wt % anti-tack agent. In embodiments where the anti-tack agent is hydrophobic, the amount of the anti-tack agent used may be sufficient to cause the liqui-mass composition to comprise less than 1.2 wt % ant-tack agent, more preferably less than 1 wt % anti tack agent, less than 0.8 wt % anti-tack agent or less than 0.65 wt % anti-tack agent.

Preferably, the amount of anti-tack agent used is sufficient to cause the liqui-mass composition to comprise between 0.1 wt % and 10 wt % anti-tack agent, more preferably between 0.2 wt % and 5 wt %, between 0.4 wt % and 2 wt % or between 0.5 wt % and 1.5 wt % anti-tack agent. In embodiments where the anti-tack agent is hydrophilic, the amount of anti-tack agent used may be sufficient to cause the liqui-mass composition to comprise between 0.75 wt % and 10 wt % anti-tack agent, more preferably between 0.8 wt % and 1.75 wt %, between 1 wt % and 1.5 wt % or between 1.1 wt % and 1.3 wt % anti-tack agent. In embodiments where the anti-tack agent is hydrophobic, the amount of anti-tack agent used may be sufficient to cause the liqui-mass composition to comprise between 0.2 wt % and 1 wt % anti-tack agent, more preferably between 0.3 wt % and 0.8 wt %, between 0.4 wt % and 0.7 wt % or between 0.5 wt % and 0.65 wt % anti-tack agent.

It may be appreciated that the method could comprise adding multiple additional excipients to the formulation. Accordingly, in a more preferred embodiment, the method comprises:
- dissolving an active pharmaceutical ingredient (API), and optionally a first additional excipient, in a liquid vehicle to form a liquid medicament;
- contacting the liquid medicament with a pharmaceutical carrier and optionally with a second additional excipient;
- optionally contacting the composition comprising the liquid medicament and pharmaceutical carrier with a third additional excipient;
- contacting the composition comprising the liquid medicament, pharmaceutical carrier, and optionally additional excipients, with a pharmaceutical coating to form a liqui-mass composition; and
- pelletising the liqui-mass composition, and optionally contacting the pelletised liquid-mass composition with a further additional excipient, to form the pharmaceutical composition.

The first additional excipient may be configured to increase the saturation limit of the API in the liquid vehicle. The second and/or third additional excipient may be selected from a disintegrant, an effervescent agent, a pH modulating agent, a retarding agent and/or a combination thereof. The further additional excipient may be an anti-tack agent.

Prior to contacting the liquid medicament with a pharmaceutical carrier, the method may comprise processing the liquid medicament to increase the saturation limit of the API in the liquid vehicle. Accordingly, the method may comprise heating the liquid medicament or treating it with ultrasound.

Preferably, the pharmaceutical carrier is an inert material. Preferably, the pharmaceutical carrier comprises a powder. The pharmaceutical carrier may comprise cellulose, and preferably comprises cellulose powder. Preferably, the cellulose comprises microcrystalline cellulose (MCC), and more preferably MCC powder. The inventors have found that MCC is able to form a wet mass with suitable rheological properties, suitable plasticity and suitable cohesiveness for extrusion and spheronisation. The cellulose powder preferably comprises a plurality of granules with a mean diameter of between 1 µM and 500 µM, more preferably between 10 µM and 250 µM or between 20 µM and 100 µM, and most preferably between 30 µM and 70 µM or between 40 µM and 60 µM.

Alternatively, or additionally, the pharmaceutical carrier may comprise a material with a large BET specific surface area. The material may comprise a BET specific surface area of at least 10 $m^2/g$, at least 20 $m^2/g$, at least 30 $m^2/g$ or at least 40 $m^2/g$, more preferably at least 50 $m^2/g$, at least 100 $m^2/g$ or at least 150 $m^2/g$, and most preferably at least 200 $m^2/g$ or at least 250 $m^2/g$. The pharmaceutical carrier may comprise magnesium aluminometasilicate or calcium phosphate. Preferably, the calcium phosphate comprises dibasic calcium phosphate anhydrous. Preferably, the pharmaceutical carrier comprises a powder. The powder power preferably comprises a plurality of granules with a mean diameter of between 1 µM and 500 PM, more preferably between 10 µM and 400 µM or between 20 µM and 300 µM, and most preferably between 40 µM and 150 µM or between 60 µM and 120 µM. For example, neusilin US2® comprises magnesium aluminometasilicate and has a BET specific surface area of 300 $m^2/g$ and a mean particle size between 60 µM and 120 µM, and fujicalin® comprises dibasic calcium phosphate anhydrous and has a BET specific surface area of 40 $m^2/g$ and a mean particle size of 115 µM.

In a preferred embodiment, the carrier comprises a combination of cellulose and a material with a large BET specific surface area. Preferably, the weight ratio of cellulose to the material with a large BET specific surface area is between 1:99 and 99:1, more preferably between 10:90 and 90:10 or between 20:80 and 80:20, and most preferably between 30:70 and 70:30 or between 40:60 and 60:40.

Advantageously, the inventors have found compositions where the carrier comprises 50 wt % cellulose powder and 50 wt % magnesium aluminometasilicate powder are easier to process and have improved drug release rates.

Preferably, the amount of the carrier used is sufficient to cause the liqui-mass composition to comprise at least 5 wt % carrier, more preferably at least 10 wt % or at least 15 wt % carrier, and most preferably at least 20 wt % carrier. Preferably, the amount of the carrier used is sufficient to cause the liqui-mass composition to comprise less than 60 wt % carrier, more preferably less than 55 wt % or less than 50 wt % carrier, and most preferably less than 45 wt % carrier. Preferably, the amount of the carrier used is sufficient to cause the liqui-mass composition to comprise between 5 wt % and 60 wt % carrier, more preferably between 10 wt % and 55 wt % or between 15 wt % and 50 wt % carrier, and most preferably between 20 wt % and 45 wt % carrier.

The method may comprise contacting the composition comprising the liquid medicament and pharmaceutical carrier with a granulating liquid. The composition comprising the liquid medicament and pharmaceutical carrier may be contacted with a granulating liquid before or after the composition has been contacted with a pharmaceutical coating. Preferably, the composition comprising the liquid medicament and pharmaceutical carrier is contacted with a granulating liquid before the composition has been contacted with a pharmaceutical coating material. The granulation liquid may comprise water, alcohol and/or polyethylene glycol (PEG). Preferably, the water is deionised water. The alcohol may be a $C_1$ to $C_{10}$ alcohol. Preferably, the alcohol is a $C_2$ to $C_4$ alcohol, more preferably the alcohol is propanol and most preferably is propan-2-ol. In a preferred embodiment, the granulating liquid is water. Alternatively, the granulating liquid may be water and an alcohol. Preferably, the weight ratio of water to alcohol is between 1:10 and 10:1, more preferably between 1:5 and 5:1 or between 1:2 and 2:1 and most preferably between 1:1 and 2:1.

Advantageously, the addition of the granulating liquid better enables the composition to be formed into pellets.

The amount of granulating liquid may vary depending on formulation composition and intended formulation design. If too much or too little granulating liquid is used the pelletisation process tends to fail due to agglomeration or unsuccessful extrusion or spheronisation.

For enhanced drug release formulations it is beneficial to use a small amount of granulating liquid. This is because less granulating liquid causes less bonding within the MCC carrier. Hence, the pellets produced are easier to disintegrate, which consequently enhances the dissolution rate. Alternatively, for sustained drug release formulations it is beneficial to use more granulating liquid. The more granulating liquid, particularly water, the more bonding within the MCC carrier; hence, the pellets produced are more resistant to disintegration. It is commonly observed that MCC based pellet with high amount of water tends to not disintegrate at all, which consequently retards dissolution rate.

Preferably, the amount of the granulation liquid used is sufficient to cause the liquid-mass composition to comprise at least 1 wt % granulation liquid, more preferably at least 2 wt % or at least 3 wt % granulation liquid, and most preferably at least 5 wt % granulation liquid. Preferably, the amount of the granulation liquid used is sufficient to cause the liquid-mass composition to comprise less than 50 wt % granulation liquid, more preferably less than 30 wt % or less than 20 wt % granulation liquid, and most preferably less than 10 wt % granulation liquid. Preferably, the amount of the granulation liquid used is sufficient to cause the liquid-mass composition to comprise between 1 wt % and 50 wt % granulation liquid, more preferably between 2 wt % and 30 wt % or between 3 wt % and 20 wt % granulation liquid, and most preferably between 5 wt % and 10 wt % granulation liquid.

Preferably, the amount of the liquid vehicle and the granulation liquid used is sufficient to cause the liquid-mass composition to comprise at least 20 wt % liquid vehicle and the granulation liquid, more preferably at least 25 wt % or at least 30 wt % liquid vehicle and the granulation liquid, and most preferably at least 35 wt % liquid vehicle and the granulation liquid. Preferably, the amount of the liquid vehicle and the granulation liquid used is sufficient to cause the liquid-mass composition to comprise less than 60 wt % liquid vehicle and the granulation liquid, more preferably less than 55 wt % or less than 50 wt % liquid vehicle and the granulation liquid, and most preferably less than 45 wt % liquid vehicle and the granulation liquid. Preferably, the amount of the liquid vehicle and the granulation liquid used is sufficient to cause the liquid-mass composition to comprise between 20 wt % and 60 wt % liquid vehicle and granulation liquid, more preferably between 25 wt % and 55 wt % or between 30 wt % and 50 wt % liquid vehicle and granulation liquid, and most preferably between 35 wt % and 45 wt % liquid vehicle and granulation liquid.

Preferably, the pharmaceutical coating is an inert material. Preferably, the pharmaceutical coating comprises a powder. The pharmaceutical coating may comprise a BET specific surface area of at least 10 m$^2$/g, at least 20 m$^2$/g, at least 30 m$^2$/g or at least 40 m$^2$/g, more preferably at least 50 m$^2$/g, at least 100 m$^2$/g or at least 150 m$^2$/g, and most preferably at least 200 m$^2$/g or at least 250 m$^2$/g. The pharmaceutical coating may comprise silica, magnesium aluminometasilicate or calcium phosphate. The silica may comprise fumed silica. Preferably, the calcium phosphate comprises dibasic calcium phosphate anhydrous. Preferably, the pharmaceutical carrier comprises a powder. The powder may comprise a plurality of granules with a mean diameter of between 1 µM and 500 PM, more preferably between 10 µM and 400 µM or between 20 µM and 300 µM, and most preferably between 40 µM and 150 µM or between 60 µM and 120 µM. For example, neusilin US2® comprises magnesium aluminometasilicate and has a BET specific surface area of 300 m$^2$/g and a mean particle size between 60 µM and 120 µM, and fujicalin® comprises dibasic calcium phosphate anhydrous and has a BET specific surface area of 40 m$^2$/g and a mean particle size of 115 µM. Alternatively, the powder may comprise a plurality of granules with a mean diameter of between 0.1 nM and 1000 nM, more preferably between 1 nM and 100 µM or between 1.5 nM and 50 PM, and most preferably between 2 µM and 25 µM or between 2.5 nM and 15 nM. For example, AEROSIL® 300 comprises fumed silica and has a BET specific surface area of 300 m$^2$/g and a mean particle size between 7 nM.

Preferably, the amount of the coating used is sufficient to cause the liqui-mass composition to comprise at least 0.25 wt % coating, more preferably at least 0.5 wt % or at least 0.75 wt % coating, and most preferably at least 1 wt % coating. Preferably, the amount of the granulation liquid used is sufficient to cause the liquid-mass composition to comprise less than 7.5 wt % coating, more preferably less than 5 wt % or less than 3 wt % coating, and most preferably less than 2.5 wt % coating. Preferably, the amount of the coating used is sufficient to cause the liquid-mass composition to comprise between 0.25 wt % and 7.5 wt % coating, more preferably between 0.5 wt % and 5 wt % or between 0.75 wt % and 3 wt % coating, and most preferably between 1 wt % and 2.5 wt % coating.

Preferably, the weight ratio of the carrier to the coating is between 40:1 and 1:1, more preferably between 30:1 and 2:1 or between 25:1 and 4:1, and most preferably is between 20:1 and 5:1.

The method may comprise drying the pharmaceutical composition. Accordingly, the method may comprise holding the pharmaceutical composition at a predetermined temperature for at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours or at least 24 hours. The predetermined temperature may be between 15° C. and 80° C., and is preferably between 20° C. and 70° C. or between 25° C. and 60° C., more preferably between 30° C. and 50° C. or between 35° C. and 45° C. Accordingly, the resultant pharmaceutical composition may comprise almost no granulating liquid due to evaporation.

The technology encompasses another new dosage form called liqui-tablet. Liqui-tablet is compressed liqui-pellet; hence, the intrinsic advantages of liqui-tablet is essentially the same or similar to that of liqui-pellet. In the preferred embodiment, once the liqui-tablet contact the dissolution medium, it reverts back to its multi-particulate form, which is essentially liqui-pellet. The method may comprise compressing the pharmaceutical composition into a tablet. Accordingly, the method may comprise compressing the composition using a force of at least 100 psi, more preferably at least 200 psi or 300 psi, and most preferably at least 400 psi. The method may comprise compressing the composition using a force of between 100 psi and 2,000 psi, preferably between 200 psi and 1,500 psi, more preferably between 300 psi and 1,000 psi and most preferably between 400 psi and 800 psi.

Advantageously, a tablet dosage form is one of the most commercial favourable dosage forms due to cost effectiveness. Tablets have low production costs and high production rate. There is also a lower risk of a tablet adhering to the oesophagus during ingestion compared to other dosage forms. A tablet allows a higher dose strength to be administered and reduces the risk of a dosage form being tampered with. Finally, a tablet leads to improved patient compliance, particularly for those who prefer not to ingest gelatine capsule.

The inventors also believe that the composition is novel and inventive per se.

In accordance with a third aspect, there is provided a pharmaceutical composition obtained or obtainable from the method of the first or second aspect.

In accordance with a fourth aspect, there is provided a pharmaceutical composition comprising a plurality of pellets or granules comprising an API, a liquid vehicle, a pharmaceutical carrier and a pharmaceutical coating material.

Preferably, the pellets or granules have an average diameter of between 10 μm and 5000 μm, more preferably between 100 μm and 4000 μm or between 250 μm and 3000 μm and most preferably between 500 μm and 2000 μm.

In accordance with a fifth aspect, there is provided a pharmaceutical composition comprising an API, a liquid vehicle, a pharmaceutical carrier and a pharmaceutical coating material, wherein the composition has a liquid load factor of at least 1.

Preferably the API is as defined in relation to the first or second aspect. Preferably, the composition comprises at least 1 wt % API, more preferably at least 5 wt % API, at least 10 wt % API, at least 15 wt % API or at least 20 wt % API, and most preferably at least 25 wt % API, at least 30 wt % API or at least 35 wt % API. The composition may comprise between 1 and 80 wt % API, more preferably between 5 and 75 wt % API, between 10 and 70 wt % API, between 15 and 65 wt % API or between 20 and 60 wt % API, and most preferably between 25 and 55 wt % API, between 30 and 50 wt % API or between 35 and 40 wt % API.

Preferably, the liquid vehicle is as defined in relation to the first or second aspect. Preferably, the composition comprises at least 5 wt % liquid vehicle, more preferably at least 10 wt %, at least 15 wt % or at least 20 wt % liquid vehicle and most preferably at least 25 wt % or 30 wt % liquid vehicle. Preferably, the composition comprises less than 65 wt % liquid vehicle, more preferably less than 60 wt %, less than 55 wt % or less than 50 wt % liquid vehicle and most preferably less than 45 wt % or 40 wt % liquid vehicle. Preferably, the composition comprises between 5 and 65 wt % liquid vehicle, more preferably between 10 and 60 wt %, between 15 and 55 wt % or between 20 and 50 wt % liquid vehicle and most preferably between 25 and 45 wt % or between 30 and 40 wt % liquid vehicle.

Preferably, the pharmaceutical carrier is as defined in relation to the first or second aspect. Preferably, the composition comprises at least 5 wt % carrier, more preferably at least 10 wt %, at least 15 wt % or at least 20 wt % carrier and most preferably at least 25 wt % or 30 wt % carrier. Preferably, the composition comprises less than 65 wt % carrier, more preferably less than 60 wt %, less than 55 wt % or less than 50 wt % carrier and most preferably less than 45 wt % or 40 wt % carrier. Preferably, the composition comprises between 5 and 65 wt % carrier, more preferably between 10 and 60 wt %, between 15 and 55 wt % or between 20 and 50 wt % carrier and most preferably between 25 and 45 wt % or between 30 and 40 wt % carrier.

Preferably, the composition comprises less than 5 wt % granulation liquid, more preferably less than 4 wt %, less than 3 wt %, less than 2 wt % or less than 1 wt % granulation liquid, and most preferably less than 0.5 wt % granulation liquid.

The pellets or granules may further comprise one or more additional excipients. The or each additional excipient may be as defined in relation to the first or second aspect.

Accordingly, the one or more additional excipients may comprise an additional excipient configured to increase the saturation limit of the API in the liquid vehicle.

Alternatively, or additionally, the one or more additional excipients may comprise a disintegrant. Preferably, the disintegrant is as defined in relation to the first or second aspect. Preferably, the composition comprises at least 1 wt % disintegrant, more preferably at least 2 wt %, or at least 3 wt % disintegrant and most preferably at least 3.5 wt % disintegrant. Preferably, the composition comprises less than 20 wt % disintegrant, more preferably less than 15 wt %, or less than 10 wt % disintegrant and most preferably less than 8 wt % disintegrant. Preferably, the composition comprises between 1 and 20 wt % disintegrant, more preferably between 2 and 15 wt % or between 3 and 10 wt % disintegrant and most preferably between 3.5 and 8 wt % disintegrant.

Alternatively, or additionally, the one or more additional excipients may comprise an effervescent agent. Preferably, the effervescent agent is as defined in relation to the first or second aspect. Preferably, the composition comprises at least 5 wt % or at least 10 wt % effervescent agent, more preferably at least 20 wt %, or at least 25 wt % effervescent agent and most preferably at least 30 wt % effervescent agent. Preferably, the composition comprises less than 60 wt % effervescent agent or less than 50 wt % effervescent agent, more preferably less than 45 wt %, or less than 40 wt % effervescent agent and most preferably less than 35 wt % effervescent agent. Preferably, the composition comprises between 5 and 60 wt % or between 10 and 50 wt % effervescent agent, more preferably between 20 and 45 wt % or between 25 and 40 wt % effervescent agent and most preferably between 30 and 40 wt % effervescent agent.

Alternatively, or additionally, the one or more additional excipients may comprise a pH modulating agent.

Alternatively, or additionally, the one or more additional excipients may comprise a retarding agent. Preferably, the retarding agent is as defined in relation to the first and second aspects. Preferably, the composition comprises at least 1 wt % retarding agent, more preferably at least 5 wt %, at least 10 wt % or at least 20 wt % retarding agent, and most preferably at least 30 wt %, at least 35 wt % or at least 40 wt % retarding agent. Preferably, the composition comprises less than 90 wt % retarding agent, more preferably less than 80 wt %, less than 70 wt % or less than 60 wt % retarding agent, and most preferably less than 50 wt %, less than 45 wt % or less than 42.5 wt % retarding agent. Preferably, the composition comprises between 1 wt % and 90 wt % retarding agent, more preferably between 5 wt % and 80 wt %, between 10 wt % and 70 wt % or between 20 wt % and 60 wt % retarding agent, and most preferably between 30 wt % and 50 wt %, between 35 wt % and 45 wt % or between 40 wt % and 42.5 wt % retarding agent.

Alternatively, or additionally, the one or more additional excipients may comprise an anti-tack agent. Preferably, the anti-tack agent is as defined in relation to the first and second aspects. Preferably, the composition comprises at least 0.1 wt % anti-tack agent, more preferably at least 0.2 wt %, at least 0.4 wt % or at least 0.5 wt % anti-tack agent. In embodiments where the anti-tack agent is hydrophilic, the composition may comprise at least 0.75 wt % anti-tack agent, more preferably at least 1 wt % or at least 1.2 wt % anti-tack agent. Preferably, the composition comprises less than 10 wt % anti-tack agent, more preferably less than 5 wt %, less than 2 wt % or less than 1.5 wt % anti-tack agent. In embodiments where the anti-tack agent is hydrophobic, the composition may comprise less than 1.2 wt % ant-tack agent, more preferably less than 1 wt % anti tack agent, less than 0.8 wt % anti-tack agent or less than 0.65 wt % anti-tack agent.

Preferably, the composition comprises between 0.1 wt % and 10 wt % anti-tack agent, more preferably between 0.2 wt % and 5 wt %, between 0.4 wt % and 2 wt % or between 0.5 wt % and 1.5 wt % anti-tack agent. In embodiments where the anti-tack agent is hydrophilic, the composition may comprise between 0.75 wt % and 10 wt % anti-tack agent, more preferably between 0.8 wt % and 1.75 wt %, between 1 wt % and 1.5 wt % or between 1.2 wt % and 1.3 wt % anti-tack agent. In embodiments where the anti-tack agent is hydrophobic, the composition may comprise between 0.2 wt % and 1 wt % anti-tack agent, more preferably between 0.3 wt % and 0.8 wt %, between 0.4 wt % and 0.7 wt % or between 0.5 wt % and 0.65 wt % anti-tack agent.

Preferably, the pharmaceutical coating material is as defined in relation to the first or second aspect. Preferably, the composition comprises at least 0.25 wt % coating, more preferably at least 0.5 wt %, or at least 0.75 wt % coating and most preferably at least 1 wt % or 1.5 wt % coating. Preferably, the composition comprises less than 15 wt % coating, more preferably less than 10 wt % or less than 7.5 wt % coating and most preferably less than 5 wt % or 3 wt % coating. Preferably, the composition comprises between 0.25 and 15 wt % coating, more preferably between 0.5 and 10 wt % or between 0.75 and 7.5 wt % coating and most preferably between 1 and 5 wt % or between 1.5 and 3 wt % coating.

The inventors also believe that a tablet produced from the composition of the third, fourth or fifth aspects is novel and inventive per se.

In accordance with a sixth aspect, there is provided a tablet comprising an API, a liquid vehicle, a pharmaceutical carrier and a pharmaceutical coating material.

The components of the tablet may be as defined in relation to the first, second, fourth and fifth aspects.

All features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:-

EXAMPLES

The inventors have developed a novel pharmaceutical composition which may be used to increase the bioavailability of an API with poor water solubility.

Figure 1:
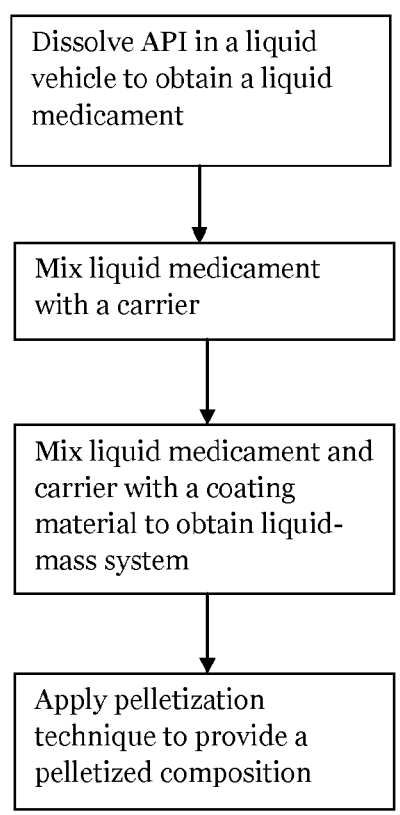
FIG. 1 is a diagram showing a method for producing a pharmaceutical composition according to the present invention.

As shown in FIG. 1, the method of producing the pharmaceutical composition comprises dissolving an API in a liquid vehicle to obtain a liquid medicament. While not shown in FIG. 1, if desired an additional excipient may be added to the liquid vehicle or the liquid vehicle may be heated or treated with ultrasound.

The liquid medicament may then be incorporated into a carrier. Again, while not shown in FIG. 1, additional excipients may be added at this stage. A coating can then be applied to the composition to provide a liqui-mass system or composition, this is usually a wet mass or paste but could also be a free-flowing powder.

Finally, the liqui-mass system or composition is pelletized to provide a pelletized composition, in the form of spherical particles. It will be appreciated that additional excipients may be added to the pelletized composition. Furthermore, the pelletized composition can be provided as free granules, in a capsule or compressed to form a tablet.

Example 1: Naproxen Liquid-Pellets

Naproxen is a nonsteroidal anti-inflammatory drug with analgesic and anti-pyretic action. It is practically insoluble in water and more so in an aqueous acidic environment, such as the stomach.

Materials and Methods Materials Naproxen was obtained from Tokyo Chemical Industry Co (Japan). Other excipients used to prepare the liqui-pellet included microcrystalline cellulose (avicel PH-101), (FMC corp., UK); colloidal silicon dioxide (aerosil 300), (Evonik Industries AG, Hanau, Germany); polyethylene glycol 200 (Fisher Scientific, Leicester, UK); propylene glycol (SAFC, Spain); polysorbate 80 (Tween 80), (Acros, Netherlands); linoleoyl macrogol-6 glycerides (Labrafil), (Gattefosse, Saint Priest, France); caprylocaproyl macrogol-8 glycerides (Labrasol), (Gattefosse, Saint Priest, France) and macrogolglycerol ricinoleate 35 (Kolliphor EL), (BASF SE, Ludwigshafen, Germany). All other reagents and solvent were of analytical grades.

Solubility Studies

Saturated solubility studies were carried out in 6 different liquid vehicles, i.e. polyethylene glycol 200 (PEG 200), propylene glycol (PG), tween 80, labrafil, labrasol and kolliphor EL. Saturated solutions were prepared by adding excess pure naproxen in a small vial containing 10 ml of liquid vehicle. The sample was then left in a bath shaker (OLS Aqua Pro, Grant Instruments Ltd, UK) for 48 h under constant temperature of 37° C. and shaking speed of 40 rpm. The supernatant was then filtered through a pre-heated filter (pore size 0.22 μm, Millex GP, Merk Millipore Ltd, Ireland), and diluted with phosphate buffer solution. This was then analyzed via UV/vis spectrophotometer (Biowave II, Biochrom Ltd, UK) to determine the concentration of naproxen in each sample. Each test was carried out in triplicate.

Preparation of Naproxen Liqui-Pellet

The liqui-pellets were prepared by mixing pure naproxen in the chosen liquid vehicle (PEG 200, PG, tween 80, labrafil, labrasol and kolliphor EL) using pestle and mortar method. All formulations contained avicel PH-101 and aerosil 300 as carrier and coating materials respectively, with a weight ratio of carrier to coating material of 20 (R-value). Avicel PH-101 was mixed into the admixture to make sure the wet liquid medication was absorbed by the carrier and not leaving residual in the mortar when transferred into a mixer (Caleva Multitab, Caleva Process Solutions Ltd, UK). The sample was mixed for 10 min at a constant rate of 125 rpm with deionized water added bit by bit to achieve reasonable plasticity for extrusion (Caleva Multitab, Caleva Process Solutions Ltd, UK). Aerosil 300 was then added into the admixture and further mixed for 10 min before extrusion-spheronization process. Spheronization was set at an almost constant rotation at 4000 rpm (decrease to 3500 rpm if agglomeration seemed likely or increase to 4500 rpm to increase pellet sphericity), however in each formulation, spheronization time varied depending on the extrudate plasticity property. Pellets were then placed in an oven under constant temperature of 50° C. overnight to remove water from pellets.

A physical mixture pellet was prepared in a similar manner except the liquid vehicle was excluded.

Table 1 shows the details of each formulation with different liquid vehicles.

| Formulation | Water content in extrudate (% w/w) | Liquid vehicle | Liquid vehicle conc in extrudate (% w/w) | Carrier conc in extrudate (% w/w) | Coating conc in extrudate (% w/w) | Naproxen conc in extrudate (% w/w) |
|---|---|---|---|---|---|---|
| Physical mixture pellet | 62.34 | | | 28.66 | 1.30 | 10.39 |
| LP-1 | 46.75 | PEG 200 | 15.59 | 25.97 | 1.30 | 10.39 |
| LP-2 | 38.80 | PG | 15.59 | 29.85 | 1.49 | 11.94 |
| LP-3 | 32.80 | Tween 80 | 17.92 | 32.78 | 1.64 | 13.11 |
| LP-4 | 30.51 | Labrafil | 19.67 | 33.90 | 1.69 | 13.56 |
| LP-5 | 25.46 | Labrasol | 20.34 | 36.36 | 1.82 | 14.54 |
| LP-6 | 32.80 | Kolliphor EL | 21.82 | 32.78 | 1.64 | 13.11 |

Table 1a: Formulation characteristics of extrudate

| Formulation | Liquid vehicle | Liquid vehicle conc. after drying (% w/w) | Carrier conc. after drying (% w/w) | Coating conc. after drying (% w/w) | Naproxen conc. after drying (% w/w) | Total weight of 25 mg naproxen liqui-pellet (mg) |
|---|---|---|---|---|---|---|
| Physical mixture pellet | | | 68.96 | 3.45 | 27.58 | 90.63 |
| LP-1 | PEG 200 | 29.27 | 48.78 | 2.44 | 19.51 | 128.13 |
| LP-2 | PG | 29.27 | 48.78 | 2.44 | 19.51 | 128.13 |
| LP-3 | Tween 80 | 29.27 | 48.78 | 2.44 | 19.51 | 128.13 |

Table 1b: Formulation characteristics of unit dose

| | | | | | | |
|---|---|---|---|---|---|---|
| LP-4 | Labrafil | 29.27 | 48.78 | 2.44 | 19.51 | 128.13 |
| LP-5 | Labrasol | 29.27 | 48.78 | 2.44 | 19.51 | 128.13 |
| LP-6 | Kolliphor EL | 29.27 | 48.78 | 2.44 | 19.51 | 128.13 |

The values for the formulation characteristics of the unit dose are calculated based on the assumption that all of the water is removed in the drying step.

The liquid load factor is defined as the weight of the liquid medication, i.e. the liquid vehicle comprising the API, divided by the weight of the carrier powder. It is calculated for the pellets based on the assumption that all of the water is removed due to the liqui-pellet being placed in the oven overnight. Accordingly, the liquid load factor is independent of the amount of granulating liquid (i.e. water) which was added to achieve reasonable plasticity. All of LP-1 to LP-6 have a liquid load factor of 1.

Assay of Drug Content

Assays were carried out in all naproxen liqui-pellet samples in order to confirm that all formulations contained the expected amount of drug that meets USP standard of 90-110%. Assays were carried out via crushing specified amount of pellets, and dissolving sample in specified amount of phosphate buffer (pH 7.4) solution for spectrophotometric analysis (Biowave II, Biochrom Ltd, UK) at a wavelength of 271 nm where naproxen can be detected.

Flowability Test on Liqui-Pellet

Techniques of measuring flow properties of the liqui-pellet that were used were: flow rate in g/sec (Flowability tester, Copley Scientific, UK), angle of repose (Flowability tester, Copley Scientific, UK and Digimatic height gage, Mitutoyo, Japan) and Carr's compressibility index using the SVM tapped density tester (D-63150, Erweka, Germany). Flow rates were measured by recording the weight (g) and time (sec) of pellets flowing through a 10 mm diameter orifice. Shutter was applied before funnel became empty of pellets. As for the angle of repose, the pellets were placed in a funnel with 10 mm diameter orifice and let to flow onto a 100 mm diameter circular test platform. The digimatic height gauge and micrometer were used to measure the height and diameter of the heap of sample, so that the angle of repose could be determined.

Carr's compressibility index (CI %) was calculated from the poured (Pb) and tapped (Pt) densities using CI equation (Eq. 1). Tapped density was measured using the tapped density tester, which was set for 100 taps. All measurements were done in triplicate.

$$CI\% = (Pt-Pb)/Pt \times 100 \quad (Eq. 1)$$

Friability Test on Liqui-Pellet

Since there is no official standard for friability test on pellets, friability test was adapted using a similar method used by Hu et al.[30]. All formulations were tested. Pellets (3 g) and glass beads (3 g) were placed in Erweka friabilator (D-63150, Erweka, Germany) under constant rotation of 25 rpm for 4 minutes. Note that the friabilator was sealed in order to prevent pellets leaving the container. Weight of the pellets before and after the friability test was recorded in order to calculate % weight loss.

Particle Size Analysis Via Sieve Method

Sieves (Test sieve, Retsch, Germany) were used to determine the size distributions of all formulations. Pellets (5 g) were sieved under vibration via mechanical shaker (AS 200, Retsch, Germany) for 1 min with an amplitude of 50, then a further 9 min with amplitude of 40, using 2000, 1000, 850, 500, 250 μm sieves. The pellets yield was determined based on the pellet fraction between 250 μm and 2000 μm and shown as the % of total pellet weight.

Stereoscopic analysis Stereoscopic analysis was performed on all formulations using an optical microscope (Nikon Labophot, Nikon, Japan), which is attached to a camera (Panasonic camera WVCL310, Panasonic, Japan). This allowed the mean Feret's diameter, roundness and elongation ratio to be calculated using particle size analysis software V1999 (designed in-house at King's College London). Note that 100 pellets per formulation were analyzed and roundness and elongation ratio was calculated using Eqs 2 and Eq. 3 respectively.

$$Roundness = (perimeter)^2/(4 \times \pi \times Area) \quad (Eq. 2)$$

$$Elongation\ ratio = Maximum\ Feret\ diameter/Minimum\ Feret\ diameter \quad (Eq. 3)$$

In-Vitro Drug Release Test

All dissolution tests were carried out using USP paddle method (708-DS Dissolution Apparatus & Cary 60 UV-Vis, Agilent Technologies, USA). The pellets in a hard gelatin capsule were under constant condition of 900 ml dissolution medium, paddle agitation of 50 rpm and temperature of 37.3 f 0.5° C. Dissolution tests used either HCl buffer solution of pH 1.2 or phosphate buffer solution of pH 7.4 to simulate gastric fluid and intestinal fluid respectively without enzymes. Absorbance (at 271 nm) was taken at time interval of 5 min until 1 hour then time interval of 10 min for another hour.

All formulation contained 25 mg of naproxen. The reason for choosing 25 mg of naproxen was because of naproxen poor solubility profile at pH 1.2 due to its weak acidic properties. According to studies by Mora and Martinez[32], naproxen solubility at 35° C. and pH 1.2 was $1.16 \times 10^{-4}$ mol/L or 27 mg/L, hence 25 mg used in test seemed reasonable. As for pH 7.4, naproxen was extremely soluble with solubility of $1.455 \times 10^{-2}$ mol/L or ~3347 mg/L. It should be noted that pH 1.2 sink condition was not maintained and this pH was only used for comparison of various formulations.

Differential Scanning Calorimetry (DSC) Studies

DSC (DCS 4000, Perkin Elmer, USA) was performed on the excipients, pure naproxen and the chosen formulations with the fastest dissolution rate in order to assess their thermal behaviour. Samples weighing between 3-6 mg were sealed in aluminium pan and thermal behavior was investigated at a scanning rate of 10° C./min, from 25° C. to 200° C. under a nitrogen atmosphere.

Statistical & Mathematical Analysis

Mean cumulative % drug release after 2 h from dissolution test were statistically analyzed by one-way analysis of variance (ANOVA). Results were quoted as significant where $p<0.05$.

Specific mathematical equations were used to analyze and compare dissolution profiles, which includes difference factor ($f_1$) equation Eq. 4 and similarity factor ($f_2$) equation Eq. 5 as described by Moore and Flanner. Both methods have been recommended by the US FDA (Food and drug administration)[35] and implemented by the FDA in various guidance documents. In brief, $f_1$ value between 0-15 and $f_2$ value between 50-100 indicates equivalence of the two dissolution profiles. Details of the equations can be found in various literature. The n represents the number of dissolution sample times and $R_t$ and $T_t$ represent the mean % of drug dissolved at each time point (t).

$$f_1 = \{[\Sigma_{t=1}^{n}|R_t - T_t|]/[\Sigma_{t=1}^{n} R_t]\} \cdot 100 \tag{Eq. 4}$$

$$f_2 = 50 \cdot \log\{[1+(1/n)\Sigma_{t=1}^{n}(R_t - T_t)^2]^{-100}\} \tag{Eq. 5}$$

Results and Discussion

Solubility Studies

As shown in Table 2, of the liquid vehicles tested, naproxen has the highest solubility in kolliphor EL and the lowest in tween 80. Despite this, the formulation containing tween 80 (LP-3) unexpectedly shows the fastest dissolution rate at pH 1.2. It is generally thought that formulation containing the liquid vehicle with the highest solubility to the drug would exhibit the fastest drug release rate; however, this is not always the case, hence, additional dissolution tests are strongly encouraged.

TABLE 2

Solubility of naproxen in a variety of liquid vehicles

| Non-volatile solvent | Mean concentration (mg/ml) ± SD | Inference |
|---|---|---|
| PEG 200 | 7.88 ± 4.87 | Slightly soluble |
| PG | 5.13 ± 0.78 | Slightly soluble |
| Tween 80 | 2.99 ± 1.01 | Slightly soluble |
| Labrafil | 10.73 ± 1.15 | Sparingly soluble |
| Labrasol | 5.14 ± 2.44 | Slightly soluble |
| Kolliphor EL | 15.83 ± 0.77 | Sparingly soluble |

Extrusion and Spheronization

Figure 2:
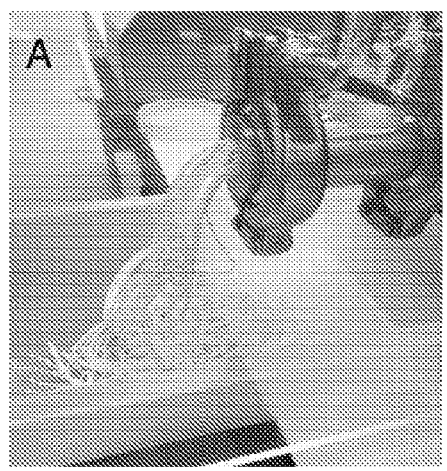
FIG. 2 shows photos of extrudate of (A) a formulation (naproxen, tween 80, avicel and aerosil) containing high water content, exhibiting high plasticity; (B) of a formulation (naproxen, PG, avicel and aerosil) containing lower water content, exhibiting lower plasticity; (C) of a physical mixture formulation (naproxen, avicel and aerosil)
Figure 2:
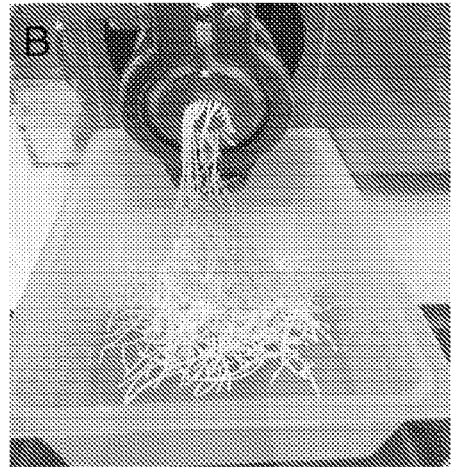
Figure 2:
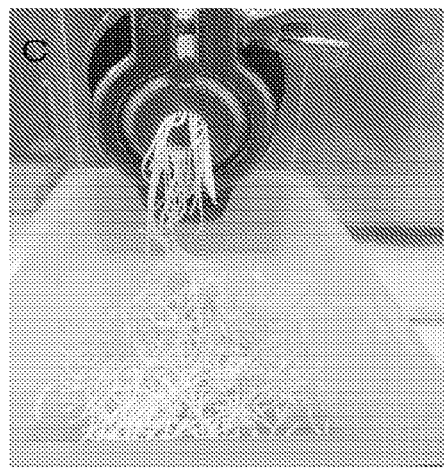

It should be noted that in the preliminary work, the moisture level or plastic properties of extrudates greatly affect the success of spheronization. Extrudate plastic property is directly linked to the amount of water added. The more water added the greater the plastic property. When the extrudate's plasticity reaches above a critical point it would usually be in a form of long threads, which are usually 3-5 cm in length, as shown in FIG. 2A. This extrudate was found to agglomerate during the spheronization, as shown in FIG. 3A. Thus, it is desirable to find the optimal water content of the extrudate. In addition, spheronization speed and time should also be considered as high speed and long duration of spheronization could lead to agglomeration.

Figure 3:
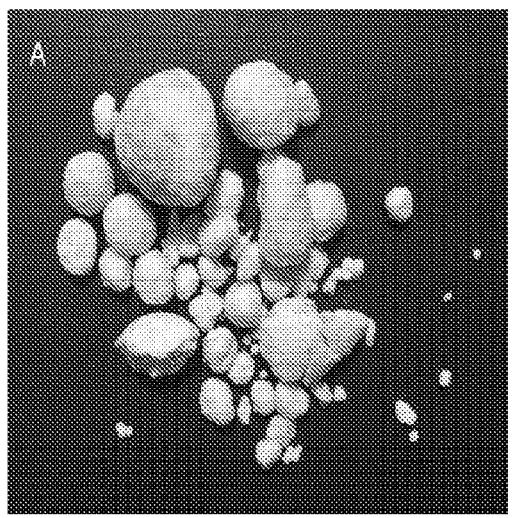
FIG. 3 shows photos of (A) an agglomerated product after spheronizing the extrudate of FIG. 2A; (B) good quality pellets after spheronizing the extrudate of FIG. 2B; and (C) reasonable quality pellets of the extrudate of FIG. 2C.
Figure 3:
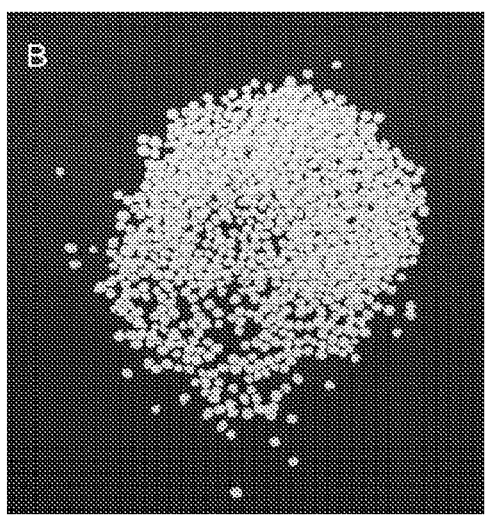
Figure 3:
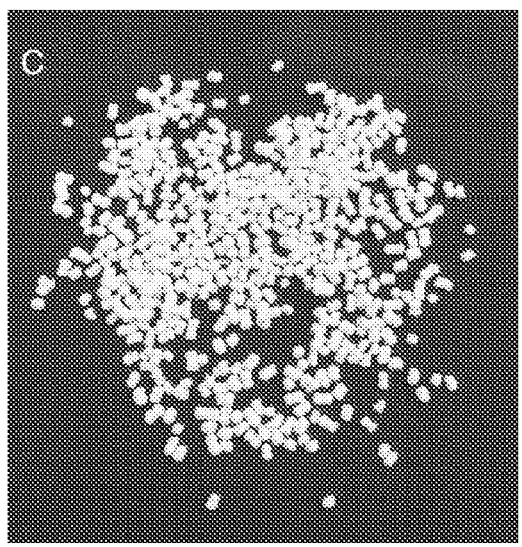

As shown in FIG. 3, the quality of pellets from formulation (B) can be similar or better than that of pellets without liquid vehicle (C). This could be due to liquid vehicle improving the rheological property in extrudate to form good spherical pellets.

Liqui-Pellet Flow Property

The results obtained from the flowability studies are given in Table 3.

TABLE 3

Results of flowability studies

| Formulation | Flow Rate (g/sec) ± SD | Angle of repose ± SD | CI % ± SD | Inference according to Angle of repose | Inference according to CI % |
|---|---|---|---|---|---|
| Physical mixture pellet | 8.02 ± 0.24 | 27.95 ± 0.14 | 9.08 ± 0.87 | Excellent flow property | Excellent flow property |
| LP-1 | 8.85 ± 0.16 | 25.89 ± 0.95 | 6.07 ± 1.71 | Excellent flow property | Excellent flow property |
| LP-2 | 8.88 ± 0.07 | 23.53 ± 0.19 | 8.93 ± 0.93 | Excellent flow property | Excellent flow property |
| LP-3 | 5.67 ± 0.28 | 30.26 ± 0.09 | 3.38 ± 0.71 | Excellent-good flow property | Excellent flow property |
| LP-4 | 6.64 ± 0.23 | 27.37 ± 0.21 | 4.16 ± 1.67 | Excellent flow property | Excellent flow property |
| LP-5 | 7.10 ± 0.16 | 27.52 ± 0.24 | 3.18 ± 1.58 | Excellent flow property | Excellent flow property |
| LP-6 | 7.12 ± 0.07 | 29.24 ± 0.57 | 3.42 ± 0.00 | Excellent flow property | Excellent flow property |

This indicates that liqui-pellet is indeed a very promising approach to overcome poor flowability. According to the angle of repose results, all formulations achieved excellent flow property apart from LP-3, which is in the borderline between excellent to good flow property. CI % results show that all formulations achieved excellent flow property.

Such results have never been achieved in a liquisolid formulation with a high liquid load factor.

This is particularly surprising given that the liquid load factor (Lf) in all the liqui-pellet formulations was 1, which is considered very high in liquisolid formulations. In fact, 28% of the total mass of the pellets were co-solvent and yet the flow properties are excellent. In other words, high Lf can be achieved whilst maintaining excellent flow properties.

Assay Via Spectrophotometer of Liqui-Pellet Formulations

Assay via spectrophotometer is shown in Table 4.

TABLE 4

Spectrophotometric assay (wavelength 271 nm) showing % drug release in 25 mg naproxen formulations and pure naproxen powder

| Formulation | Mean % drug release ± SD |
|---|---|
| Pure naproxen powder | 98.78 ± 0.23 |
| Physical mixture pellet | 96.54 ± 2.30 |
| LP-1 | 95.68 ± 1.22 |
| LP-2 | 129.68 ± 0.58 |
| LP-3 | 100.88 ± 1.10 |
| LP-4 | 101.84 ± 0.66 |
| LP-5 | 99.94 ± 0.46 |
| LP-6 | 101.79 ± 1.27 |

This shows that all of the formulations, except LP-2, show a good amount of drug release nearing to 100%. What is unusual is that LP-2 shows~30% more naproxen in the formulation than expected. Initially, it was thought that this was due to experimental or processing error and so the LP-2 was remade but the assay still showed~130% drug content. It is unclear as to why liqui-pellet with propylene glycol liquid vehicle shows that it contains more drugs than expected. This could be due to the presence of PG in the formulation causing interference in the absorption reading.

Friability Test

The results obtained from the friability test are provided in Table 5.

TABLE 5

Weight loss of 3 g of each formulation under rotational speed of 25 rpm for 4 min

| Formulation | % Weight loss |
| --- | --- |
| Physical mixture pellet | 0.54 |
| LP-1 | 0.03 |
| LP-2 | 0 |
| LP-3 | 0.29 |
| LP-4 | 0.53 |
| LP-5 | 0.3 |
| LP-6 | 0.43 |

This shows all formulations have % weight loss below 1%, which is considered acceptable for tablets under USP standard. This indicates that liqui-pellets are ideal for commercial manufacturing as it is robust to friability. The microcrystalline cellulose carrier forms strong bonding within its structure when water is added, producing pellets with strong structure which is resistant to being friable. Also, the liquid vehicle in liqui-pellet increases the pellet plasticity, which effectively increases the pellet resistant to being friable.

Particle Size of Liqui-Pellet Via Sieve Method

Figure 4:
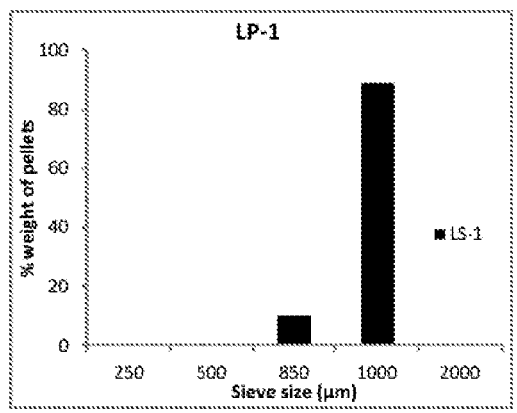
FIG. 4 shows the particle size distribution of formulations LP-1 to LP-6 and the physical mixture pellet formulation.
Figure 4:
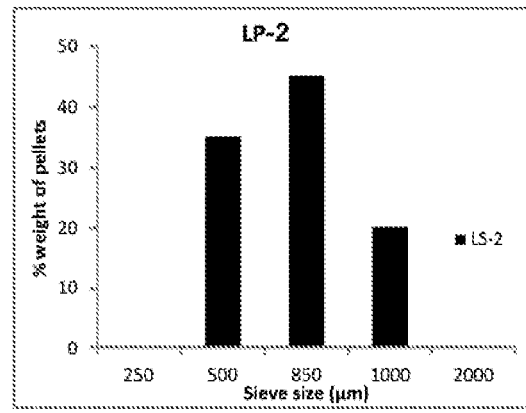
Figure 4:
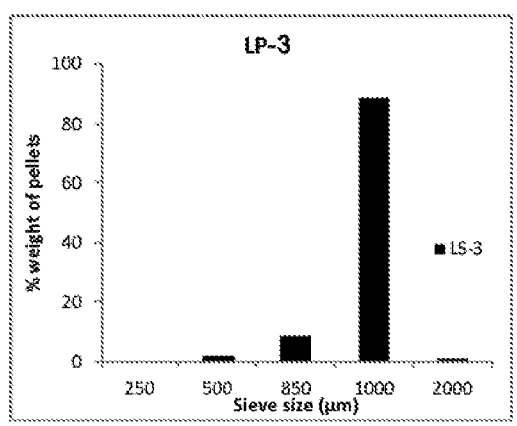
Figure 4:
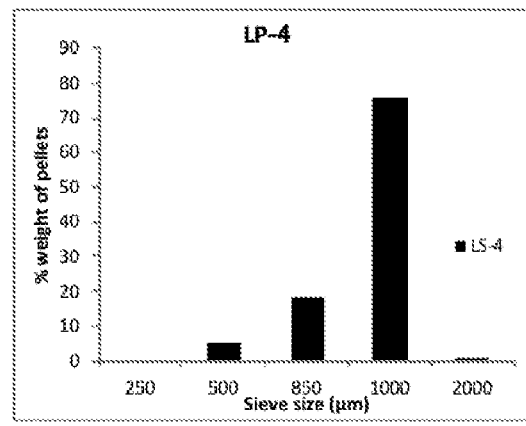
Figure 4:
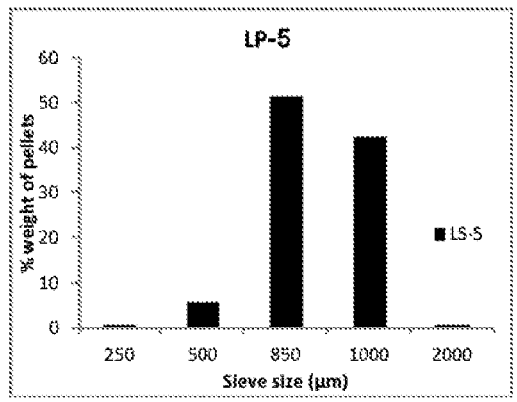
Figure 4:
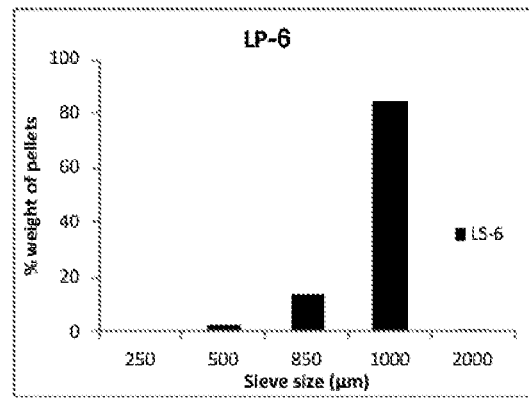
Figure 4:
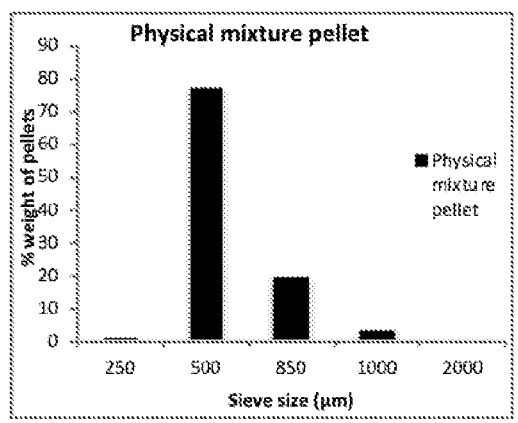

The particle size distribution of the formulation is shown in FIG. 4. As shown in FIGS. 4A, 4C, 4D and 4F, the majority of the pellets in formulations LP-1, LP-3, LP-4 and LP-6 have a diameter between 1 mm and 2 mm. This shows that it is possible to produce a uniform size of liqui-pellet.

As shown in FIGS. 4B and 4E, formulations LP-2 and LP-5 exhibit a broader size distribution with smaller sized pellets compared to the rest of the liqui-pellet formulations. For the LP-2 formulation, ~45% of the total pellets have a diameter between 850 μm and 1 mm and ~35% have a diameter between 500 μm and 850 μm. For LP-5 formulation, ~51% of total pellets have a diameter between 850 μm and 1 mm and ~5.8% have a diameter between 500 μm and 850 μm. This indicates the liquid vehicle can have an effect on liqui-pellet size distribution, which can be assumed to be due to its effect on extrudate plasticity. Meanwhile, in the physical mixture pellet, which does not contain a liquid vehicle, ~77% of the pellets pellet have a diameter between 500 μm and 850 μm. This indicates that the liquid vehicle tends to increase pellet size.

Since of the vast majority of the pellets have a diameter of less than 2 mm, they will pass from the stomach into the small intestine relatively quickly, similar to a liquid. This is advantageous for weakly acidic drugs, such as naproxen, as they undergo dissolution at a faster rate in less acidic and more alkaline environment such as the small intestine.

Stereoscopic Analysis

The results from the stereoscopic analysis are given in Table 6.

TABLE 6

Stereoscopic analysis showing the mean Feret's diameter, mean roundness and mean elongation of each formulation

| Formulations | Mean Feret's diameter (mm) | Mean roundness ± SD | Mean elongation ratio ± SD |
| --- | --- | --- | --- |
| Physical mixture pellet | 1.028 | 1.25 ± 0.12 | 1.41 ± 0.19 |
| LP-1 | 1.294 | 1.12 ± 0.07 | 1.15 ± 0.10 |
| LP-2 | 1 | 1.12 ± 0.03 | 1.17 ± 0.09 |
| LP-3 | 1.517 | 1.14 ± 0.09 | 1.18 ± 0.17 |
| LP-4 | 1.303 | 1.18 ± 0.07 | 1.25 ± 0.11 |
| LP-5 | 1.268 | 1.24 ± 0.11 | 1.41 ± 0.21 |
| LP-6 | 1.535 | 1.38 ± 0.18 | 1.47 ± 0.18 |

In general, the Feret's diameter of the formulations seems to agree with most of the results from particle size analysis via sieve method. Thus, supporting the claim that different liquid vehicles can influence pellet size and generally increase pellet size.

However, there are some discrepancies between the two data. It can be seen that the mean ferret diameter of the physical mixture pellet, LP-2 and LP-5 could be overestimated.

Formulations LP-6, LP-5 and physical mixture pellet showed the least roundness and largest elongation ratio. Among them, LP-6 has the highest deviation from perfect roundness (1.38) and largest mean elongation ratio (1.47). Nevertheless, as discussed above, the pellets are good enough to achieve excellent flowability. As for the rest of the formulation, the results seem to suggest the rest of the liqui-pellets have good roundness and minimal elongation.

Drug Release Study

Figure 5:
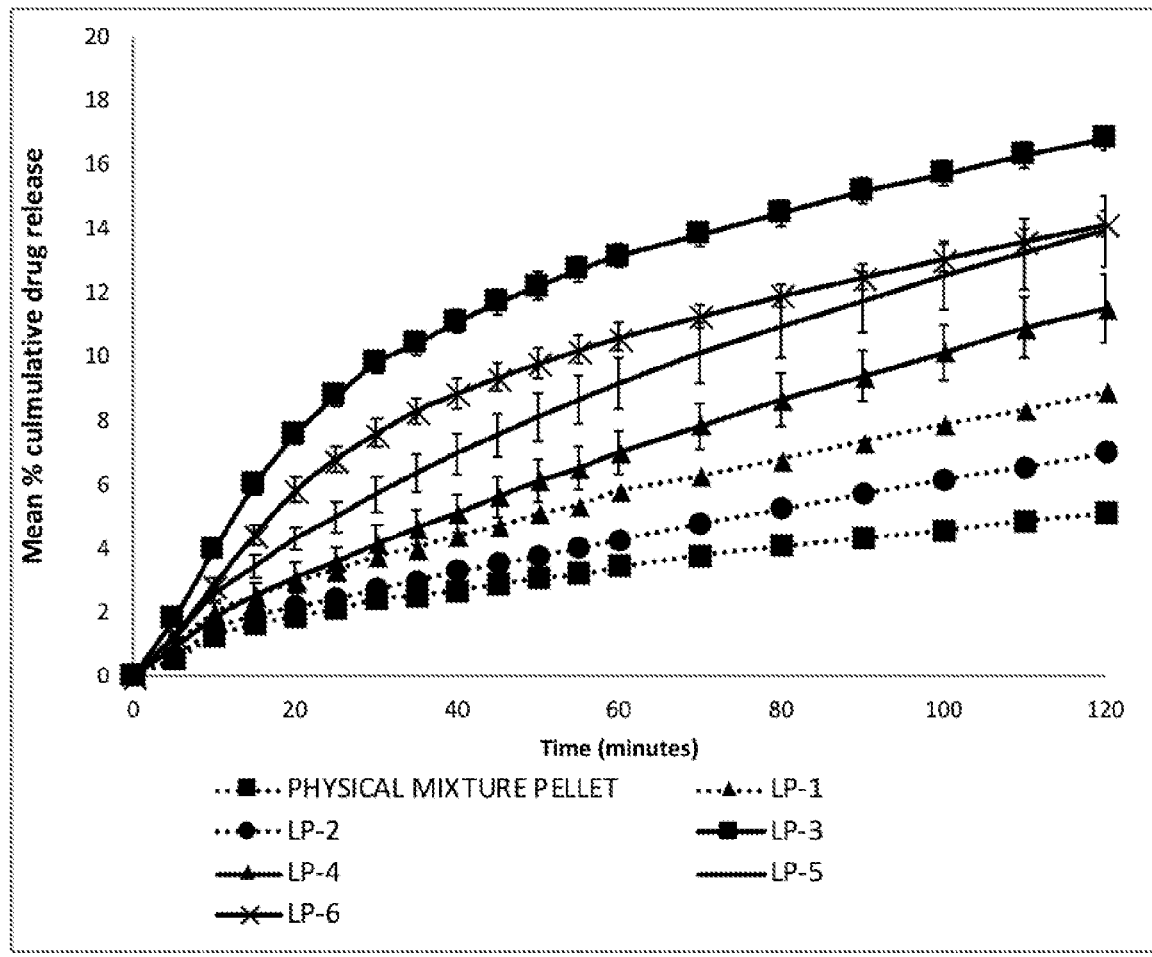
FIG. 5 is a graph showing the dissolution profile of formulations LP-1 to LP-6 and the physical mixture pellet formulation at pH 1.2.
Figure 6:
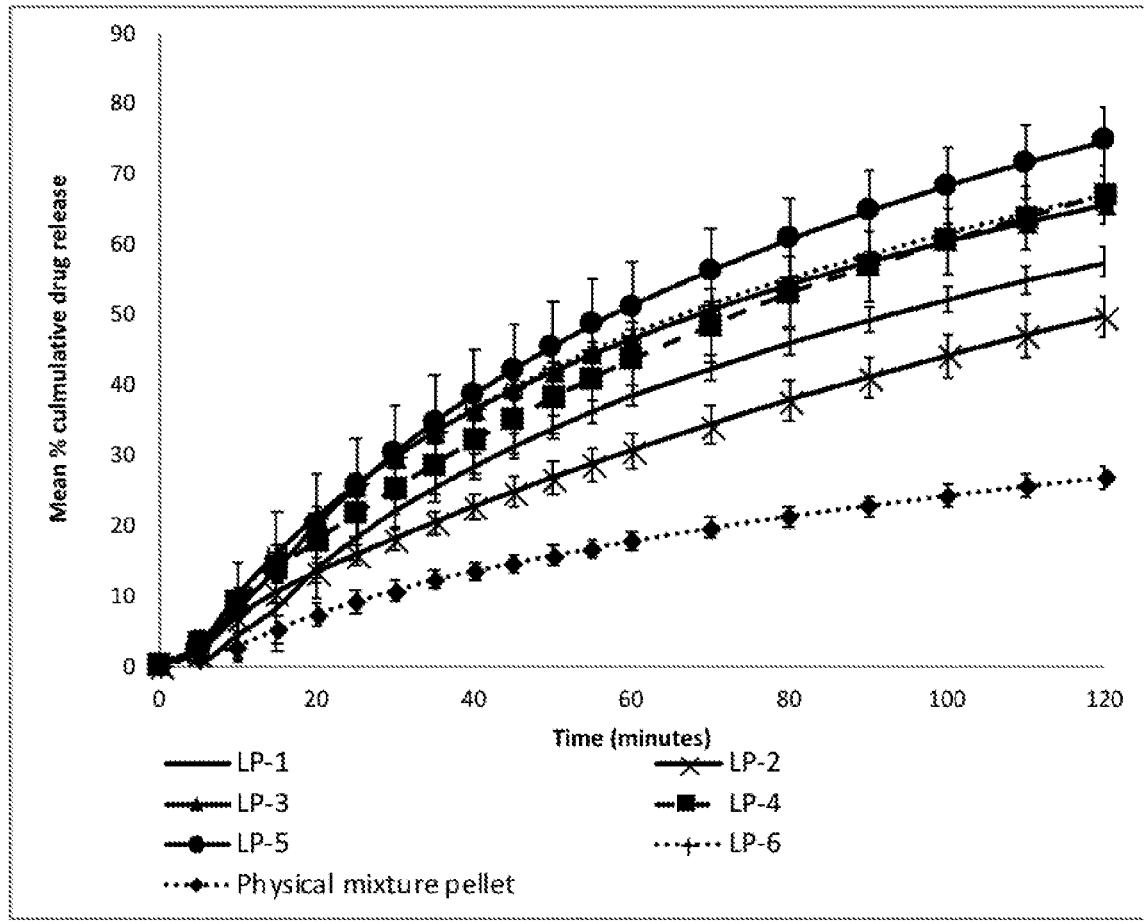
FIG. 6 is a graph showing the dissolution profile of formulations LP-1 to LP-6 and the physical mixture pellet formulation at pH 7.4.

The dissolution profiles of the liqui-pellet formulations at pH 1.2 are shown in FIG. 5, and the dissolution profiles of the liqui-pellet formulations at pH 7.4 are shown in FIG. 6. As shown in the Figures, in each case a liquid vehicle considerably enhances drug release compared to the physical mixture pellet ($p<0.05$), which does not contain a liquid vehicle. The difference factor ($f_1$) and similarity factor ($f_2$) for LP-3 and the physical mixture, are 272.56 and 53.53 respectively. This indicates a marked difference in the two dissolution profiles.

In contrast to the results obtained from the solubility test, the dissolution results at pH 1.2 show that LP-3 achieved the fastest drug release rate. Admittedly, even though formulation with tween 80 has the fastest dissolution rate, the percentage cumulative drug release is about 17% after 2 hours, which is poor. Nonetheless the poor dissolution rate is expected as the solubility of naproxen at pH 1.2 and 35° C. is about 27 mg/L.

As expected, the drug release rate increased significantly at pH 7.4. At this pH, LP-5 has the fastest drug release rate, with a cumulative drug release of ~75% achieved after 2 h, whereas LP-3 had released about ~66% after 2 h. It is noted that their $f_1$ and $f_2$ are 9.23 and 66.04 respectively, indicating little difference in dissolution profile. The changes between the results suggest that the pH can affect the drug release rate of different liquid vehicle at different rates.

In this case for the inventors believe that tween 80 is the most suitable liquid vehicle for naproxen since the aim is to have fast onset of action and fast release. Thus, it is prudent that the drug release rate is high in acidic condition as the drug will be in the stomach before entering the small intestine. It should be noted that although the aim is to have fast onset of action and fast drug release, in reality, drug like naproxen would have enteric coat due to potential GI irritation and the main site of absorption will be in the small intestine. For this reason, labrasol and kolliphor EL may also be a suitable liquid vehicle for naproxen.

DCS Studies

Figure 7:
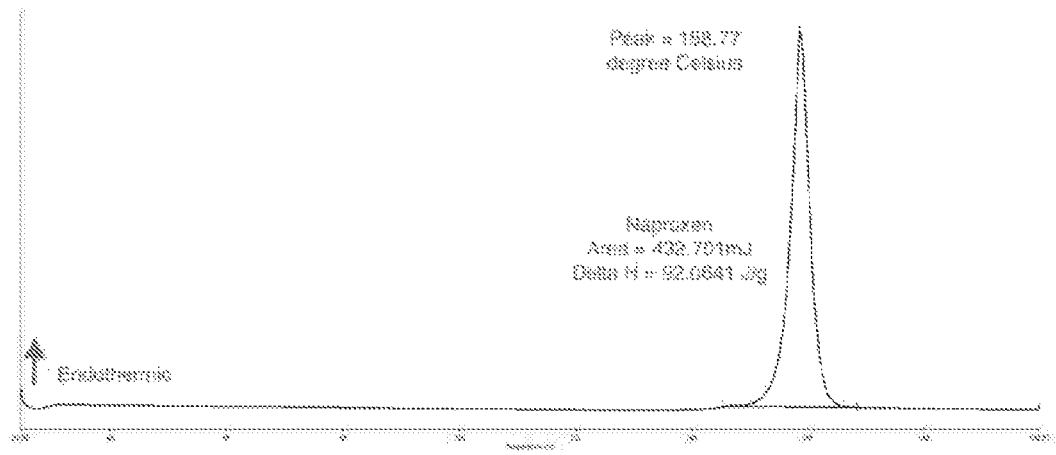
FIG. 7 shows a differential scanning calorimetry (DSC) thermogram of naproxen.
Figure 8:
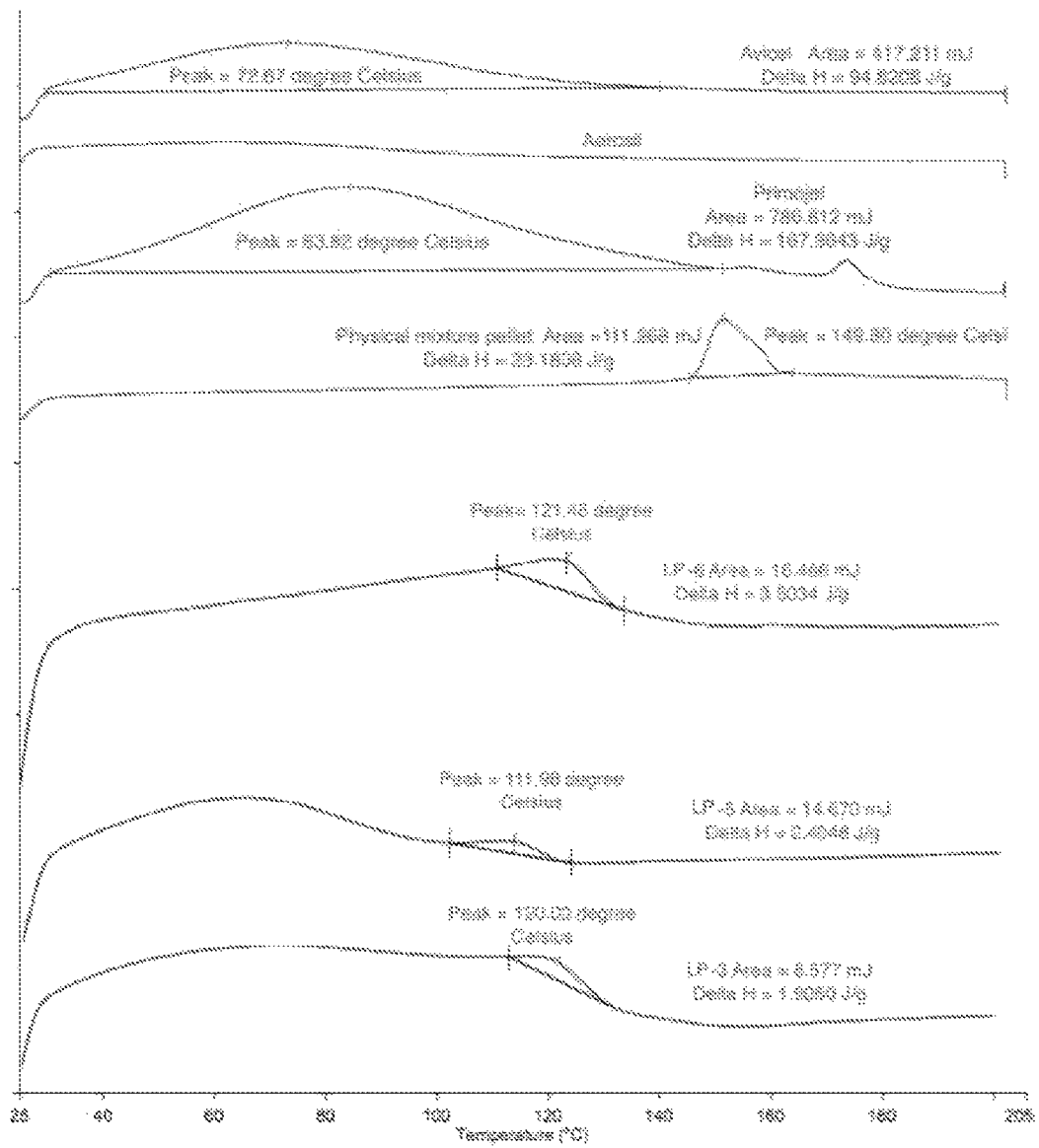
FIG. 8 shows a DSC thermogram of avicel, aerosil, primojel, physical mixture pellet, LP-3, LP-5 and LP-6.

Thermograms obtained from differential scanning calorimetry include naproxen; avicel; aerosil; primojel; physical mixture pellets; LP-3; LP-5 and LP-6. FIG. 7 shows a sharp endothermic peak ($T_m$=158.77° C. and $\Delta H$=92.06 J/g) for naproxen, indicating its crystalline state. As shown in FIG. 8, avicel ($T_m$=72.67° C. and $\Delta H$=94.82 J/g) and primojel ($T_m$=83.82° C. and $\Delta H$=167.36 J/g) traces both have a broad peak, which could be due to water within avicel and primojel evaporating, as they are hygroscopic materials. The thermogram for aerosil had no definitive peak.

The thermogram for the physical mixture pellet shows a peak at 149.8° C., a lower temperature than for naproxen. The peak shift could be due to the avicel affecting the overall peak of naproxen in the physical mixture pellets. Nevertheless, the presence of the peak shows that naproxen is present in the crystalline state.

However, for formulation LP-3 ($T_m$=1200° C. and $\Delta H$=1.9060 J/g), LP-5 ($T_m$=111.98° C. and $\Delta H$=2.4048 J/g) and LP-6 ($T_m$=121.48° C. and $\Delta H$=3.5034 J/g), the DSC traces did not include a naproxen peak, and had a lower $T_m$ than the trace for the physical mixture pellet. This indicates that the naproxen in the liqui-pellets has reduced crystallinity and has become more amorphous.

Conclusion

The liqui-pellet is able to achieve high liquid load factor whilst maintaining excellent flow properties. Excellent-good flow properties were obtained from all liqui-pellet formulations which had Lf of 1. DSC showed that the crystallinity of liqui-pellet is reduced, and this is one of the key factors for the observed improvement in enhanced drug release.

Example 2: Optimising the Release Rate

As mentioned above, the inventors believe that tween 80 is the most suitable co-solvent for naproxen. Accordingly, Example 2 focuses on liqui-pellets which use tween 80 as a co-solvent, and by changing other variables attempts to optimise the release rate.

Materials and Methods

Materials

Naproxen was obtained from Tokyo Chemical Industry Co (Japan). Other excipients used to prepare the liqui-pellet included microcrystalline cellulose (avicel PH-101), (FMC corp., UK); colloidal silicon dioxide (aerosil 300), (Evonik Industries AG, Hanau, Germany); sodium starch glycolate Type A (primojel), (DFE Pharma, Goch, Germany); croscarmellose (primellose), (DFE Pharma., Goch, Germany), 2-propranol (VWR Chemicals, Fontenay Sous Bois France); polysorbate 80 (Tween 80) and PEG mw of 1500. All other reagents and solvent were of analytical grades.

Preparation of Naproxen Liqui-Pellet

The naproxen liqui-pellet formulations were prepared in a similar manner described in Example 1. However, in all of LP-7 to LP-17, a superdisintegrant was added. For all of the formulations except LP-13, the superdisintegrant was added intragranularly, i.e. it was added at the same time as the carrier, prior to the granulating liquid. For LP-13 the superdisintegrant was added extragranularly, i.e. after the granulating liquid.

When formulations LP-10 to LP-12 were prepared the step of adding a liquid vehicle was omitted.

Formulation between LP-7 to LP-12 mainly focused on investigating the effect of varying the concentration of primojel with and without the presence of a liquid vehicle. Formulation LP-10 to LP-12 have no liquid vehicle. Formulation between LP-13 to LP-17 mainly focused on modifying the formulation to improve the dissolution rate. In LP-16, a mixture of PEG and deionised water (5% w/v) was used instead of only deionised water; and in LP-17 a mixture of propan-2-ol and deionised water of equal ratio was used instead of only deionised water.

Details of the various formulations are given in Table 7.

TABLE 7

Key extrudate characteristics

| Formulation | Pre-extrusion liquid | Pre-extrusion liquid content in extrudate (% w/w) | Liquid vehicle conc in extrudate (% w/w) | Carrier conc in extrudate (% w/w) | Coating conc in extrudate (% w/w) |
|---|---|---|---|---|---|
| Physical mixture pellet | Water | 62.34 | | 28.66 | 1.30 |
| LP-7 | Water | 30.09 | 19.73 | 32.88 | 1.65 |
| LP-8 | Water | 30.43 | 18.87 | 31.49 | 1.58 |
| LP-9 | Water | 30.75 | 18.03 | 30.01 | 1.50 |
| LP-10 | Water | 53.13 | | 30.66 | 1.53 |
| LP-11 | Water | 53.13 | | 29.09 | 1.46 |
| LP-12 | Water | 61.54 | | 22.54 | 1.13 |
| LP13 | Water | 30.09 | 19.73 | 32.88 | 1.65 |
| LP-14 | Water | 8.63 | 35.13 | 34.48 | 1.72 |
| LP-15 | Water | 30.09 | 19.73 | 32.88 | 1.65 |
| LP-16 | Water and PEG in a weight ratio of 20:1 | 32.36 | 19.09 | 31.81 | 1.59 |
| LP-17 | Water and 2-propanol in a weight ratio of 10:7.9 | 29.94 | 19.78 | 32.95 | 1.65 |

| Formulation | Super-disintegrant type | Superdisintegrant conc in extrudate (% w/w) | Naproxen conc in extrudate (% w/w) |
|---|---|---|---|
| Physical mixture pellet | | | 10.39 |
| LP-7 | Primojel | 2.63 | 13.15 |
| LP-8 | Primojel | 5.03 | 12.58 |
| LP-9 | Primojel | 7.21 | 12.02 |
| LP-10 | Primojel | 2.46 | 12.28 |
| LP-11 | Primojel | 4.65 | 11.62 |
| LP-12 | Primojel | 5.42 | 9.03 |
| LP13 | Primojel | 2.63 | 13.15 |
| LP-14 | Primojel | 3.44 | 17.22 |
| LP-15 | Primellose | 2.63 | 13.15 |
| LP-16 | Primojel | 2.54 | 12.72 |
| LP-17 | Primojel | 2.63 | 13.17 |

Key formulation characteristics of the liqui-pellet compositions

| Formulation | Liquid vehicle conc. after drying (% w/w) | Carrier conc. after drying (% w/w) | Coating conc. after drying (% w/w) |
|---|---|---|---|
| Physical mixture pellet | | 68.96 | 3.45 |
| LP-7 | 28.23 | 47.03 | 2.35 |
| LP-8 | 27.12 | 45.26 | 2.26 |
| LP-9 | 26.04 | 43.34 | 2.17 |

TABLE 7-continued

| Formulation | Super-disintegrant conc after drying (% w/w) | Naproxen conc after drying (% w/w) | Total weight of 25 mg naproxen liqui-pellet (mg) |
|---|---|---|---|
| LP-10 | 0.00 | 65.41 | 3.27 |
| LP-11 | 0.00 | 62.07 | 3.10 |
| LP-12 | 0.00 | 58.60 | 2.93 |
| LP13 | 28.23 | 47.03 | 2.35 |
| LP-14 | 38.45 | 37.74 | 1.88 |
| LP-15 | 28.23 | 47.03 | 2.35 |
| LP-16 | 28.23 | 47.03 | 2.35 |
| LP-17 | 28.23 | 47.03 | 2.35 |

| Formulation | Super-disintegrant type | Super-disintegrant conc after drying (% w/w) | Naproxen conc after drying (% w/w) | Total weight of 25 mg naproxen liqui-pellet (mg) |
|---|---|---|---|---|
| Physical mixture pellet |  |  | 27.58 | 90.63 |
| LP-7 | Primojel | 5 | 18.80 | 132.95 |
| LP-8 | Primojel | 10 | 18.08 | 138.24 |
| LP-9 | Primojel | 15 | 17.36 | 144.03 |
| LP-10 | Primojel | 5 | 26.20 | 95.42 |
| LP-11 | Primojel | 10 | 24.80 | 100.81 |
| LP-12 | Primojel | 15 | 23.47 | 106.53 |
| LP13 | Primojel | 5 | 18.80 | 132.95 |
| LP-14 | Primojel | 5 | 18.85 | 132.66 |
| LP-15 | Primellose | 5 | 18.80 | 132.95 |
| LP-16 | Primojel | 5 | 18.80 | 132.95 |
| LP-17 | Primojel | 5 | 18.80 | 132.95 |

As explained in Example 1, the values for the formulation characteristics of the unit dose are calculated based on the assumption that all of the granulating liquid is removed in the drying step.

The remaining methods were the same as described in Example 1.

Results and Discussion

Liqui-Pellet Flow Property

Results from the flowability tests are shown in Table 8.

TABLE 8

Flow rate (g/sec), Angle of repose and Carr's compressible index (CI %) of physical mixture formulation and LP-7 to LP-17

| Formulation | Flow Rate (g/sec) ± SD | Angle of repose ± SD | CI % ± SD | Inference according to Angle of repose | Inference according to CI % |
|---|---|---|---|---|---|
| Physical Mixture Pellet | 8.02 ± 0.24 | 27.95 ± 0.14 | 9.08 ± 0.87 | Excellent flow property | Excellent flow property |
| LP-7 | 7.60 ± 0.10 | 26.98 ± 0.74 | 5.25 ± 0.86 | Excellent flow property | Excellent flow property |
| LP-8 | 7.61 ± 0.12 | 27.75 ± 0.31 | 8.13 ± 1.65 | Excellent flow property | Excellent flow property |
| LP-9 | 7.42 ± 0.22 | 28.68 ± 0.53 | 6.07 ± 1.44 | Excellent flow property | Excellent flow property |
| LP-10 | 10.68 ± 0.06 | 23.81 ± 0.40 | 9.95 ± 0.08 | Excellent flow property | Excellent flow property |
| LP-11 | 8.59 ± 0.08 | 28.20 ± 0.16 | 11.17 ± 0.85 | Excellent flow property | Good flow property |
| LP-12 | 6.96 ± 0.28 | 29.21 ± 0.26 | 10.37 ± 0.79 | Excellent flow property | Excellent-good flow property |
| LP-13 | 7.13 ± 0.07 | 28.68 ± 0.22 | 7.24 ± 2.33 | Excellent flow property | Excellent flow property |
| LP-14 | 5.82 ± 0.09 | 30.51 ± 0.38 | 3.90 ± 2.30 | Excellent-good flow property | Excellent flow property |
| LP-15 | 7.35 ± 0.05 | 28.57 ± 0.50 | 7.63 ± 1.42 | Excellent flow property | Excellent flow property |
| LP-16 | 6.47 ± 0.19 | 30.13 ± 0.19 | 9.24 ± 0.73 | Excellent-good flow property | Excellent flow property |
| LP-17 | 6.03 ± 0.25 | 30.47 ± 0.51 | 7.76 ± 0.76 | Excellent-good flow property | Excellent flow property |

Similar to the results obtained in Example 1, all of the formulations have excellent or in the borderline between excellent to good flow properties. The $L_f$ for LP-14 is as high as 1.52, where 38.45 wt % of the pellet total mass is co-solvent, and yet excellent-good flow properties are still achieved.

Particle Size Analysis Via Sieve Method

The particle size analysis suggests that ~97% of the pellets in formulation LP-14 have a diameter of between 1 mm and 2 mm. This is similar to the results obtained for LP-3 in example 1 (see FIG. 4C), and indicates that increasing the liquid load factor to 1.52 and adding a superdisintegrant has little effect on the pellet size.

Formulation LP-17 shows a wider size distribution with ~64% of the pellets having a diameter between 850 μm and 1 mm and ~32% having a diameter of between 1 mm and 2 mm. This could be due to reduced plastic property due to the granulating liquid being a mixture of water and propan-2-ol.

Drug Release Study

Figure 9:
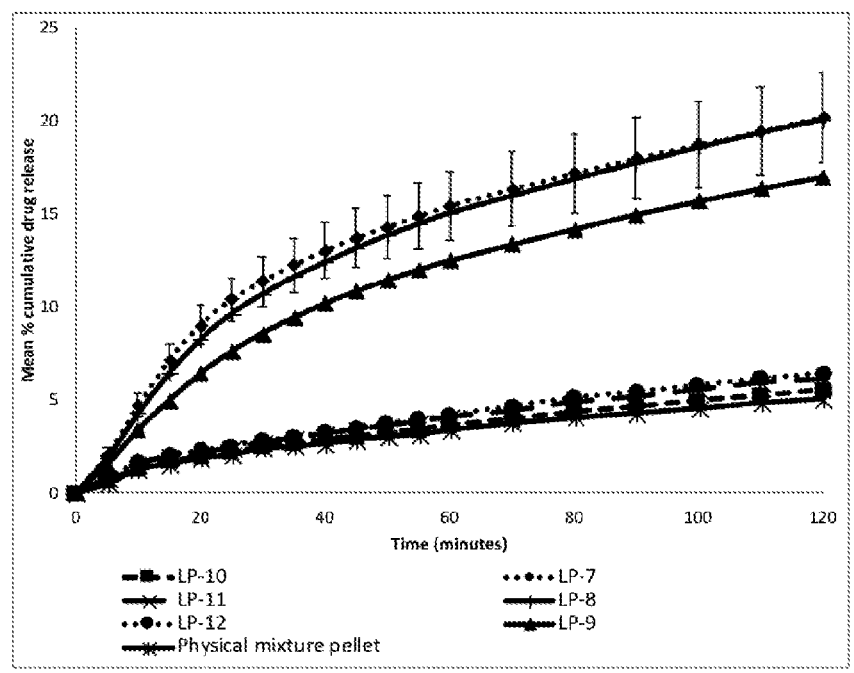
FIG. 9 is a graph showing the dissolution profile of formulations LP-7 to LP-12 and the physical mixture pellet formulation at pH 1.2.

Dissolution test of formulations LP-7 to LP-12 and the physical mixture pellet formulation are shown in FIG. 9. As shown in Table 7b (above), LP-7 to LP-9 contain Tween 80 co-solvent and between 5-15 wt % primojel (a superdisintegrant). By way of contrast, LP-10 to LP-12 also contain between 5-15 wt % primojel, but do not contain any co-solvent.

Formulations LP-7 and LP-8, containing 5 wt % and 10 wt % primojel respectively, had similar dissolution profiles ($F_1$=3.3 and $F_2$=97.84). These formulations had a faster dissolution rate than LP-3 (example 1), which did not contain any superdisintegrant. It can be seen that formulation LP-9, which contained 15 wt % primojel did not perform quite as well as LP-7 or LP-8. This suggests that increasing the amount of superdisintegrant to 15 wt % slightly impedes dissolution. This may be due to primojel forming a gel at higher concentrations, which can slow down dissolution rate.

Meanwhile, formulations LP-10 to LP-12 all displayed a considerably slower drug release rate (p<0.05). Even with different concentrations of primojel incorporated into the formulation, the dissolution profiles of LP-10 to LP-12 are similar to that of physical mixture pellet (p>0.05). This further confirms that the incorporation of a co-solvent is advantageous.

Figure 10:
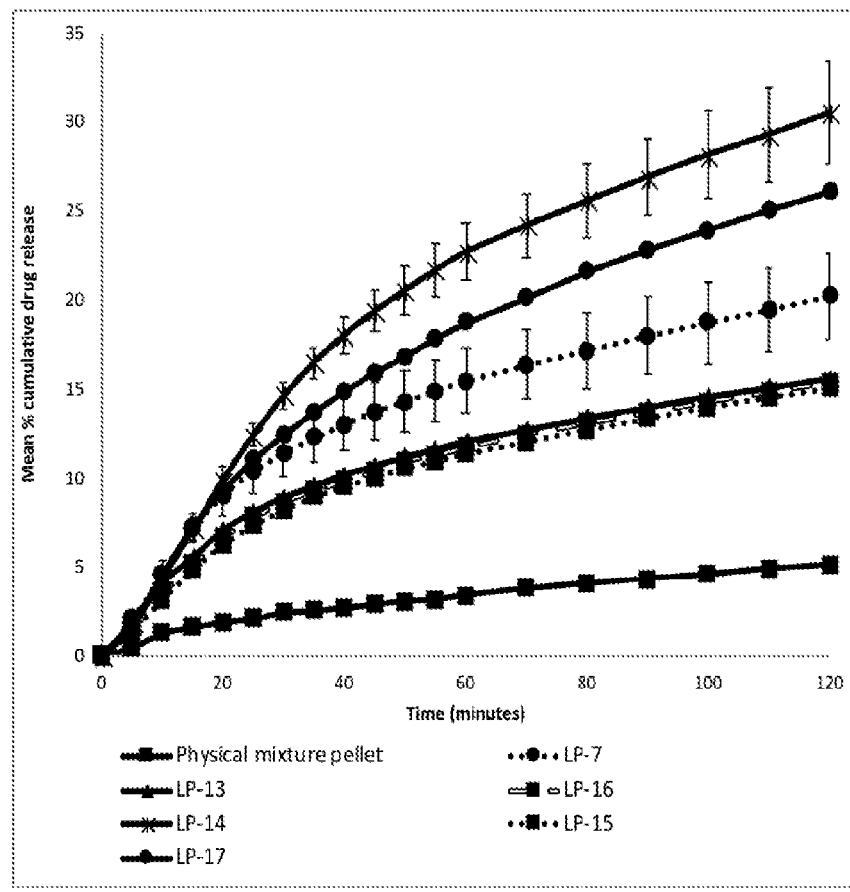
FIG. 10 is a graph showing the dissolution profile of formulations LP-7 and LP-13 to LP-17 and the physical mixture pellet formulation at pH 1.2.

Dissolution test of formulations LP-7 and LP-13 to LP-17 and the physical mixture pellet formulation are shown in FIG. 10. As shown in Table 7 (above), LP-7 and LP-13 to LP-17 all contain Tween 80 co-solvent and 5 wt % of a superdisintegrant.

As shown in FIG. 10, LP-14, which has a liquid loading factor of 1.52, shows the best enhanced drug release profile. It is noted that a drug release of about 30% is observed for LP-14 after two hours. Conversely, the non-optimized LP-3 formulation in FIG. 5 only showed a release of about 18% of the drug release after 2 hours. Accordingly, the increase of the amount of liquid vehicle and the inclusion of a superdisintegrant significantly increases the amount of drug which is released.

Formulation LP-17, where propan-2-ol and water were used as the pre-extrusion liquid, has the second best enhanced release rate, with about ~26% of the drug being released within 2 hours. It is hypothesised that the improvement in release rates for both LP-14 and LP-17 is due to a decreased amount of water being present in the formulation.

The inventors note that LP-13, where the primojel was added later in the manufacturing process (extragranularly), shows a slower drug release rate than LP-7, where the primojel was added at the same time as the carrier (intragranularly). This indicates that intragranular incorporation of primojel is more effective than extragranular incorporation.

LP-15, where the superdisintegrant used was primellose, shows a slower drug release rate than LP-7 where the superdisintegrant used were primojel. Accordingly, it appears that for the naproxen liqui-pellets, primojel is a preferred superdisintegrant compared to primellose, and should be added early in the manufacturing process.

Finally, it is noted that LP-16, where PEG and water were used as the granulating liquid, does not show an improvement in the dissolution rate.

Figure 11:
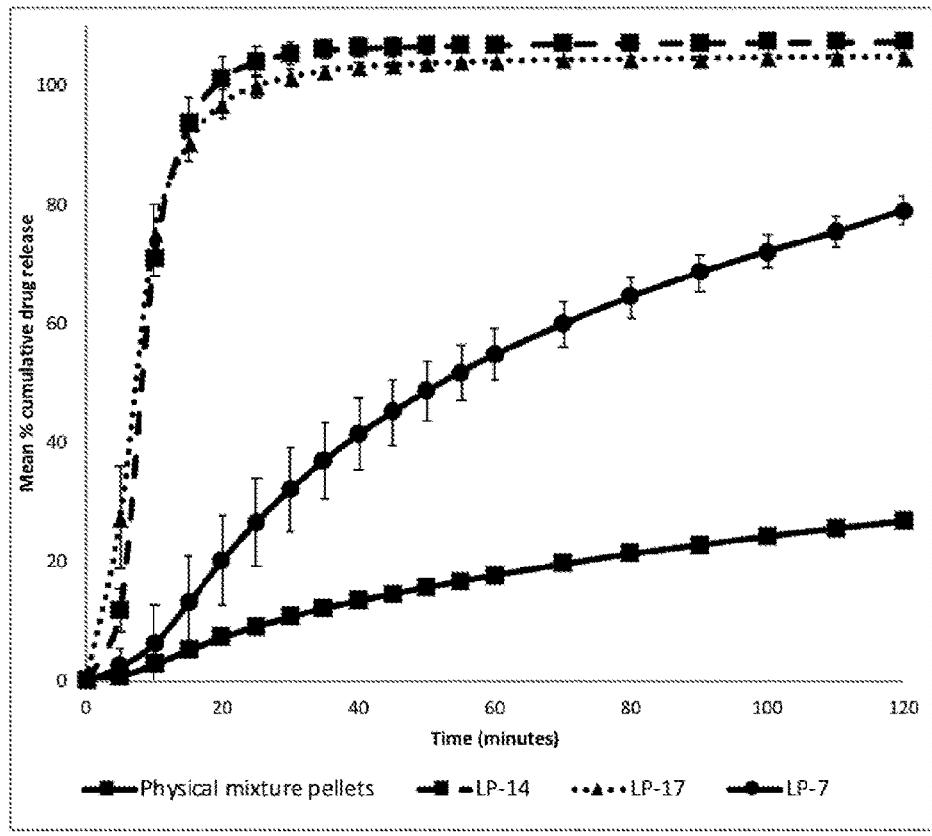
FIG. 11 is a graph showing the dissolution profile of formulations LP-7, LP-14 and LP-17 and the physical mixture pellet formulation at pH 7.4.

LP-14 and LP-17 showed the best drug release rates at pH 1.2. Accordingly, the inventors selected these formulations for further testing at pH 7.4, and the results are shown in FIG. 11. As shown in the figure, both LP-14 and LP-17 were found to have 100% drug release after 20 minutes. This shows that naproxen liqui-pellets are capable of achieving fast drug release, which is likely to improve bioavailability.

Conclusion

As demonstrated above, it is possible to obtain a liqui-pellet with good flow properties which has a high liquid load factor. The inventors have also shown that the dissolution rates of the liqui-pellet can be improved by:

1) increasing the amount of co-solvent in the formulation;

2) using a superdisintegrant, this effect is enhanced when the superdisintegrant is primojel and is added intragranularly; and/or 3) decreasing the concentration of water in the pellet, e.g. by using a combination of water and propan-2-ol as the pre-extrusion liquid.

Example 3: Investigating the Effect of Water and Co-Solvent

The inventors wanted to investigate the effect that the amount of water added as a pre-extrusion liquid and the co-solvent had on the liqui-pellets.

Materials and Methods

Materials

Naproxen was obtained from Tokyo Chemical Industry Co (Japan). Other excipients used to prepare the liqui-pellet included microcrystalline cellulose (avicel PH-101), (FMC corp., UK); colloidal silicon dioxide (aerosil 300), (Evonik Industries AG, Hanau, Germany); sodium starch glycolate Type A (primojel), (DFE Pharma, Goch, Germany); polysorbate 20 (tween 20), (Acros, Netherlands); polysorbate 80 (tween 80), (Acros, Netherlands) and polysorbate 85 (tween 85), (Acros, Netherlands). All other reagents and solvent were of analytical grades.

Preparation of Naproxen Liqui-Pellet with Different Tween Co-Solvent

The naproxen liqui-pellet formulations were prepared in the similar manner as described in Example 1. All formulations contained 25 mg of naproxen and the carrier to coating ratio of 20:1 respectively. Also, all of the formulations contained roughly 5 wt % primojel. However, the type and amount of liquid vehicle in the formulation, the water content of the formulation, and the presence of primojel was varied as set out in Table 9.

TABLE 9 a: Key extrudate characteristics of LP-1 to LP-19

| Formulation | Water content in extrudate (% w/w) | Liquid vehicle | Liquid vehicle conc in extrudate (% w/w) | Liquid load factor | Carrier conc in extrudate (% w/w) |
|---|---|---|---|---|---|
| Physical mixture pellet | 23.11 | | | | 49.36 |
| LPF-1 | 30.12 | Tween 20 | 19.57 | 1.00 | 32.87 |
| LPF-2 | 30.12 | Tween 80 | 19.57 | 1.00 | 32.87 |
| LPF-3 | 30.12 | Tween 85 | 19.57 | 1.00 | 32.87 |
| LPF-4 | 30 | Tween 80 | 22.40 | 1.18 | 30.37 |
| LPF-5 | 30 | Tween 80 | 25.20 | 1.38 | 27.84 |
| LPF-6 | 30 | Tween 80 | 28.00 | 1.63 | 25.30 |
| LPF-7 | 30 | Tween 80 | 30.80 | 1.94 | 22.77 |
| LPF-8 | 19.22 | Tween 80 | 25.85 | 1.18 | 35.04 |
| LPF-9 | 19.22 | Tween 80 | 29.08 | 1.38 | 32.12 |
| LPF-10 | 19.22 | Tween 80 | 32.31 | 1.63 | 29.19 |
| LPF-11 | 19.22 | Tween 80 | 35.54 | 1.94 | 26.27 |
| LPF-12 | 8.68 | Tween 80 | 29.22 | 1.18 | 39.62 |
| LPF-13 | 8.68 | Tween 80 | 32.88 | 1.38 | 36.32 |
| LPF-14 | 8.68 | Tween 80 | 36.53 | 1.63 | 33.01 |
| LPF-15 | 8.68 | Tween 80 | 40.18 | 1.94 | 29.70 |
| LPF-16 | 4.53 | Tween 80 | 30.55 | 1.18 | 41.42 |
| LPF-17 | 4.53 | Tween 80 | 34.37 | 1.38 | 37.96 |
| LPF-18 | 4.53 | Tween 80 | 38.19 | 1.63 | 34.50 |
| LPF-19 | 4.53 | Tween 80 | 42.00 | 1.94 | 31.05 |

| Formulation | Coating conc in extrudate (% w/w) | Super-disintegrant conc in extrudate (% w/w) | Naproxen conc in extrudate (% w/w) | Successfully spheronized into pellet? (Yes/No) |
|---|---|---|---|---|
| Physical mixture pellet | 2.46 | 3.84 | 21.22 | Yes |
| LPF-1 | 1.64 | 3.49 | 13.17 | Yes |
| LPF-2 | 1.64 | 3.49 | 13.17 | Yes |
| LPF-3 | 1.64 | 3.49 | 13.17 | Yes |
| LPF-4 | 2.05 | 3.50 | 13.19 | Yes |
| LPF-5 | 1.39 | 3.50 | 13.19 | No |
| LPF-6 | 1.27 | 3.50 | 13.19 | No |
| LPF-7 | 1.14 | 3.50 | 13.19 | No |
| LPF-8 | 2.36 | 4.04 | 15.22 | Yes |
| LPF-9 | 1.61 | 4.04 | 15.22 | Yes |
| LPF-10 | 1.46 | 4.04 | 15.22 | No |
| LPF-11 | 1.31 | 4.04 | 15.22 | No |
| LPF-12 | 2.67 | 4.57 | 17.21 | Yes |
| LPF-13 | 1.82 | 4.57 | 17.21 | Yes |
| LPF-14 | 1.65 | 4.57 | 17.21 | No |
| LPF-15 | 1.49 | 4.57 | 17.21 | No |
| LPF-16 | 2.79 | 4.77 | 17.99 | Yes |
| LPF-17 | 1.90 | 4.77 | 17.99 | No |
| LPF-18 | 1.73 | 4.77 | 17.99 | No |
| LPF-19 | 1.55 | 4.77 | 17.99 | No |

The physical mixture pellet, LPF-1 to LPF-4, LPF-8, LPF-9, LPF-12, LPF-13 and LPF-16 were successfully spheronized into pellets and then dried. The concentrations of the components in the final compositions are given below.

b: Key formulation characteristics of formulations which were spheronized

| Formulation | Liquid vehicle | Liquid vehicle conc after drying (% w/w) | Liquid load factor | Carrier conc after drying (% w/w) |
|---|---|---|---|---|
| Physical mixture pellet | | | | 64.20 |
| LPF-1 | Tween 20 | 19.57 | 1.00 | 47.03 |
| LPF-2 | Tween 80 | 19.57 | 1.00 | 47.03 |
| LPF-3 | Tween 85 | 19.57 | 1.00 | 47.03 |
| LPF-4 | Tween 80 | 22.40 | 1.18 | 43.38 |
| LPF-8 | Tween 80 | 25.85 | 1.18 | 43.38 |
| LPF-9 | Tween 80 | 29.08 | 1.38 | 39.77 |

TABLE 9-continued

| | | | | |
|---|---|---|---|---|
| LPF-12 | Tween 80 | 29.22 | 1.18 | 43.38 |
| LPF-13 | Tween 80 | 32.88 | 1.38 | 39.77 |
| LPF-16 | Tween 80 | 30.55 | 1.18 | 43.38 |

| Formulation | Coating conc after drying (% w/w) | Super-disintegrant conc after drying (% w/w) | Naproxen conc after drying (% w/w) | Total mass of 25 mg naproxen liqui-pellet (mg) |
|---|---|---|---|---|
| Physical mixture pellet | 3.20 | 5.00 | 27.60 | 90.58 |
| LPF-1 | 2.34 | 5.00 | 18.84 | 132.7 |
| LPF-2 | 2.34 | 5.00 | 18.84 | 132.7 |
| LPF-3 | 2.34 | 5.00 | 18.84 | 132.7 |
| LPF-4 | 2.92 | 5.00 | 18.84 | 132.7 |
| LPF-8 | 2.92 | 5.00 | 18.84 | 132.7 |
| LPF-9 | 1.99 | 5.00 | 18.84 | 132.7 |
| LPF-12 | 2.92 | 5.00 | 18.84 | 132.7 |
| LPF-13 | 1.99 | 5.00 | 18.84 | 132.7 |
| LPF-16 | 2.92 | 5.00 | 18.84 | 132.7 |

The remaining methods were the same as described in Example 1.

Results and Discussion

Saturation Solubility Test

Table 10 shows the solubility of naproxen in a variety of tween co-solvents. It is noted that all of the solvents were sparingly soluble, but tween 80 showed the best solubility and tween 85 the poorest.

TABLE 10

Solubility of naproxen in a variety of tween co-solvents

| Non-volatile solvent | Mean concentration (mg/ml) ± SD | Inference |
|---|---|---|
| Tween 20 | 17.98 ± 3.09 | Sparingly soluble |
| Tween 80 | 21.85 ± 1.88 | Sparingly soluble |
| Tween 85 | 14.27 ± 1.58 | Sparingly soluble |

Success of Spheronizing Formulation

As mentioned above, the physical mixture pellet, LPF-1 to LPF-4, LPF-8, LPF-9, LPF-12, LPF-13 and LPF-16 were successfully spheronized into pellets. However, LPF-5 to LPF-7, LPF-10, LPF-11, LPF-14, LPF-15 and LPF-17 to LPF-19 were not successfully spheronized into pellets. In general, there seems to be a limit of how much water and co-solvent that can be added until the formulation is prone to agglomeration, leading to failure in liqui-pellet production.

For instance, in formulations where the extrudate comprised about 30 wt % of water it was only possible to successfully spheronize the extrudate into pellets when the extrudate contained 22.5 wt % or less of co-solvent (which resulted in formulations comprising 32 wt % or less of co-solvent after drying), i.e. formulations LPF-1 to LPF-4. Conversely, the extrudates for LPF-5 to LPF-7 all contained 30 wt % water and at least 25 wt % co-solvent, and the extrudate formed has sticky surface and highly plastic properties, which led to agglomeration during the spheronization process.

The extrudates of LPF-8 to LPF-11 contained 19.22 wt % water, and it was possible to successfully spheronize these formulations when they contained up to 29.08 wt % co-solvent (which resulted in formulations comprising 36 wt % or less of co-solvent after drying). Similarly, the extrudates of LPF-12 to LPF-15 contained 8.68 wt % water, and it was possible to successfully spheronize these formulations when they contained 32.88 wt % co-solvent or less (which again resulted in formulations comprising 36 wt % or less of co-solvent after drying). It is noted that when less water is used it is possible to use more co-solvent before the overall plasticity of the extrudate is above the limit that causes agglomeration.

However, it is noted that the extrudates of LPF-16 to LPF-19 all contained 4.53 wt % water, and it was only possible to successfully spheronize the formulation into pellets when the extrudate contained 30.55 wt % of co-solvent (which resulted in a formulation comprising 32 wt % co-solvent), i.e. formulation LPF-16. This is because when low concentrations of water and high concentrations of co-solvent are used, the extrudate is soft and cohesive, and will agglomerate during the spheronization process.

Flow Properties

The flowability of all of the formulations which were formed into pellets was analysed and the results are shown in Table 11.

TABLE 11

Flow rate (g/sec), Angle of repose and Carr's compressible index (CI %) of physical mixture formulation and LPF-1 to LPF-4, LPF-8, LPF-9, LPF-12, LPF-13 and LPF-16

| Formulation | Flow Rate (g/sec) ± SD | Angle of repose ± SD | CI % ± SD | Inference according to Angle of repose | Inference according to CI % |
|---|---|---|---|---|---|
| Physical mixture formulation | 10.72 ± 0.33 | 19.96 ± 1.43 | 11.11 ± 0.62 | Excellent flowability | Good flowability |
| LPF-1 | 8.77 ± 0.16 | 23.81 ± 0.74 | 10.08 ± 0.55 | Excellent flowability | Excellent-good flowability |

TABLE 11-continued

Flow rate (g/sec), Angle of repose and Carr's compressible index (CI %) of physical
mixture formulation and LPF-1 to LPF-4, LPF-8, LPF-9, LPF-12, LPF-13 and LPF-16

| Formulation | Flow Rate (g/sec) ± SD | Angle of repose ± SD | CI % ± SD | Inference according to Angle of repose | Inference according to CI % |
|---|---|---|---|---|---|
| LPF-2 | 8.22 ± 0.29 | 23.51 ± 0.19 | 12.11 ± 0.64 | Excellent flowability | Good flowability |
| LPF-3 | 8.08 ± 0.07 | 23.95 ± 0.21 | 12.73 ± 0.00 | Excellent flowability | Good flowability |
| LPF-4 | 6.74 ± 0.08 | 28.7 ± 0.20 | 11.05 ± 1.36 | Excellent flowability | Good flowability |
| LPF-8 | 7.17 ± 0.10 | 27.63 ± 0.31 | 10.17 ± 0.63 | Excellent flowability | Excellent-good flowability |
| LPF-9 | 7.07 ± 0.11 | 27.65 ± 1.00 | 6.31 ± 0.70 | Excellent flowability | Excellent flowability |
| LPF-12 | 6.12 ± 0.18 | 31.02 ± 0.66 | 7.33 ± 0.00 | Good flowability | Excellent flowability |
| LPF-13 | 6.4 ± 0.19 | 29.52 ± 0.85 | 3.96 ± 0.00 | Excellent flowability | Excellent flowability |
| LPF-16 | 5.57 ± 0.25 | 30.87 ± 0.55 | 5.80 ± 0.74 | Excellent-good flowability | Excellent flowability |

Again, all of the formulations show excellent, excellent-good or good flowability.

Particle Size of Formulated Liqui-Pellet Via Sieve Method

The particle size distribution tests clearly showed a narrow size distribution for all formulations, as shown in table 12.

TABLE 12

Particle size distribution for physical mixture pellet,
LPF-1 to LPF-4, LPF-8, LPF-9, LPF-12, LPF-13 and LPF-16

| Formulation | % weight of pellets | | | | |
|---|---|---|---|---|---|
| | 250 μM to 500 μM | 500 μM to 850 μM | 850 μM to 1000 μM | 1000 μM to 2000 μM | >2000 μM |
| Physical mixture pellet | 0.07 | 53.95 | 45.21 | 0.24 | 0.00 |
| LPF-1 | 0 | 2.82 | 32.45 | 64.25 | 0.00 |
| LPF-2 | 0.00 | 1.16 | 28.09 | 70.28 | 0.00 |
| LPF-3 | 0.00 | 1.22 | 12.57 | 85.67 | 0.00 |
| LPF-4 | 0.00 | 0.00 | 0.12 | 99.09 | 0.32 |
| LPF-8 | 0.00 | 0.17 | 4.38 | 94.47 | 0.47 |
| LPF-9 | 0.00 | 0.00 | 0.86 | 99.08 | 0.00 |
| LPF-12 | 0.00 | 0.10 | 1.30 | 98.22 | 0.26 |
| LPF-13 | 0.00 | 0.06 | 1.69 | 97.71 | 0.49 |
| LPF-16 | 0.00 | 0.12 | 1.42 | 97.92 | 0.49 |

These narrow size distributions are ideal for commercial manufacturing, particularly when considering the uniformity of drug content during the filling process into capsule or filling stage during tabletting.

It is noted that the changes in water content and tween 80 concentration did not have a significant impact on the liqui-pellet size distribution.

Dissolution Studies

Figure 12:
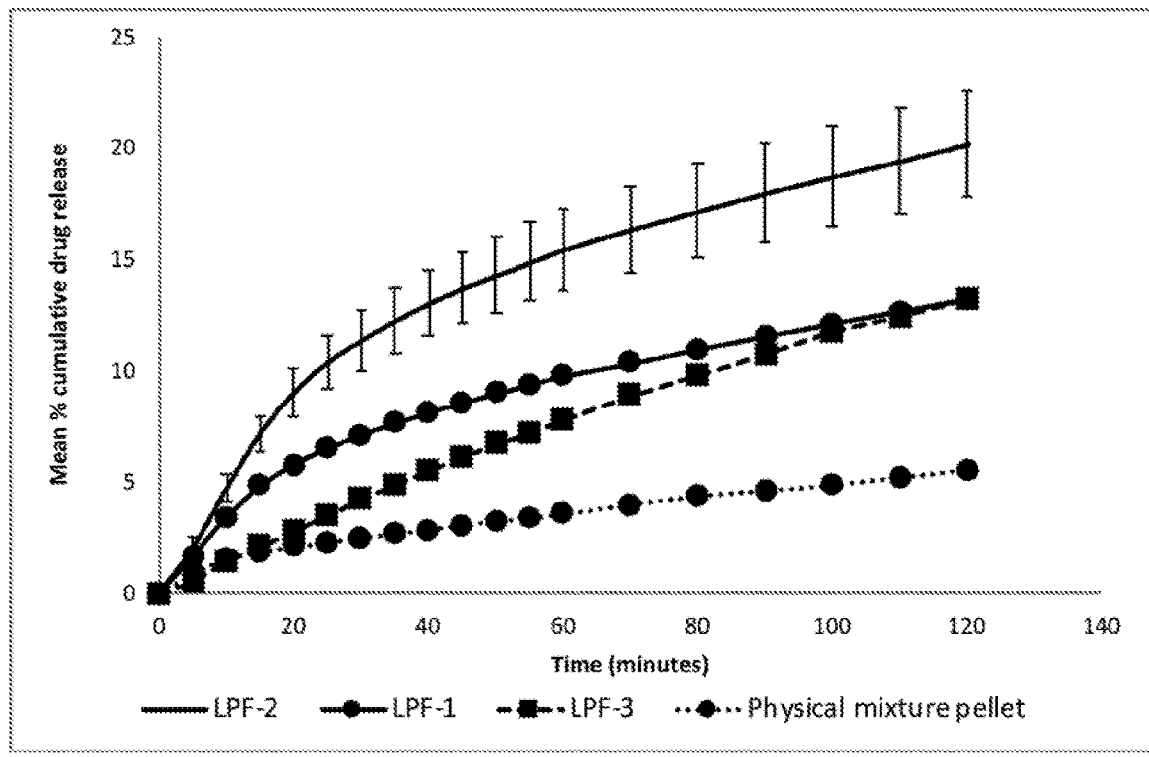
FIG. 12 is a graph showing the dissolution of formulations LPF-1 to LPF-3 and the physical mixture pellet formulation at pH 1.2.

As shown in FIG. 12, LPF-2, the formulation where the co-solvent is tween 80, has the fastest drug release rate. Conversely, LPF-3, the formulation where the co-solvent is tween 85, has the slowest. These results correspond with the solubility studies.

Figure 13:
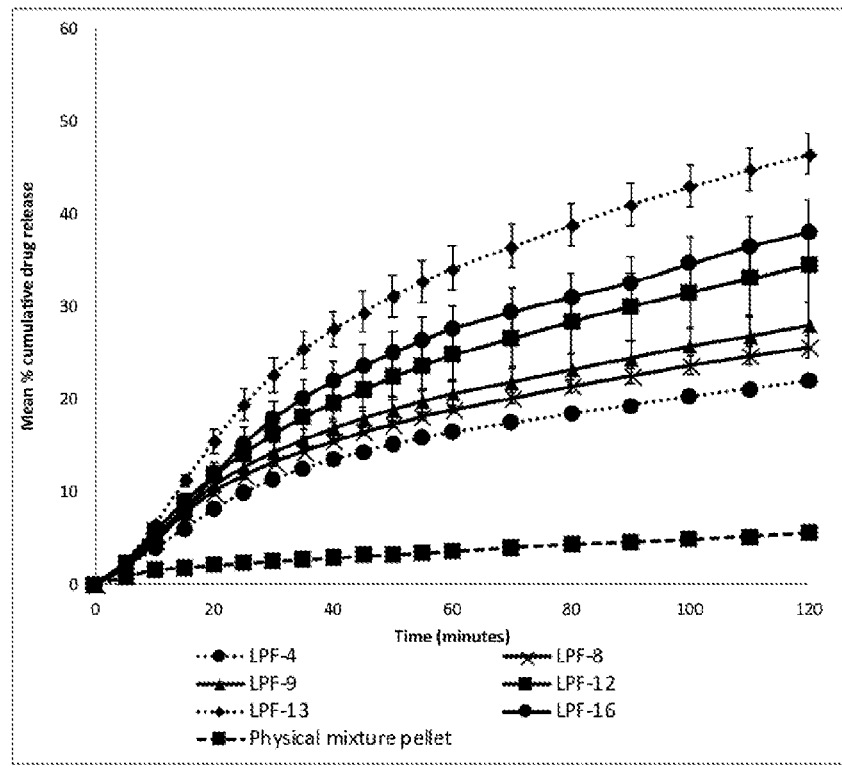
FIG. 13 is a graph showing the dissolution of formulations LPF-4, LPF-8, LPF-9, LPF-12, LPF-13, LPF-16 and the physical mixture pellet formulation at pH 1.2.
Figure 14:
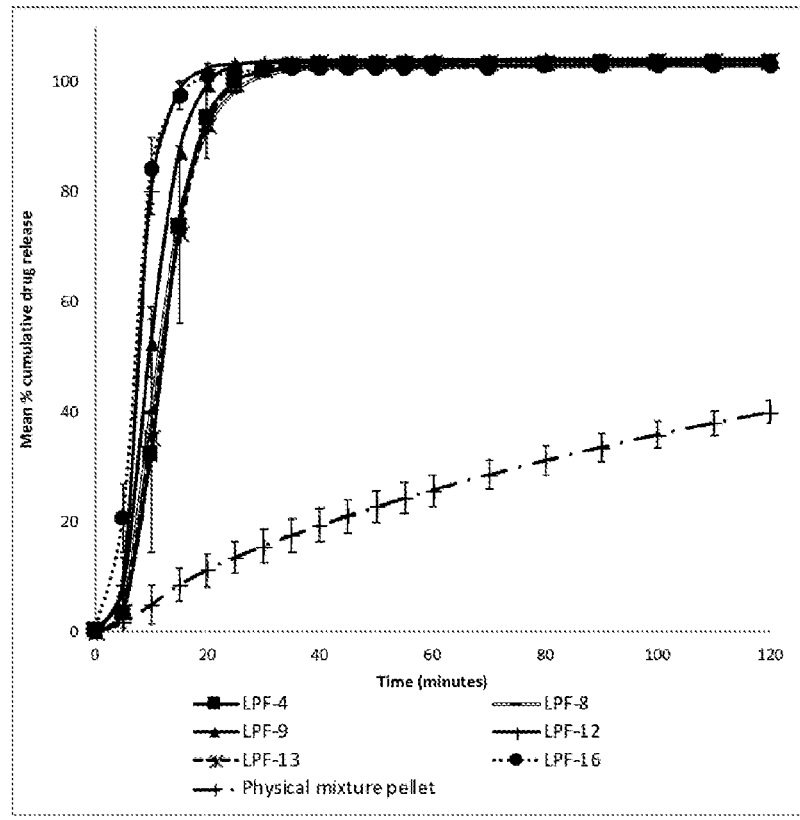
FIG. 14 is a graph showing the dissolution of formulations LPF-4, LPF-8, LPF-9, LPF-12, LPF-13, LPF-16 and the physical mixture pellet formulation at pH 7.4.

Meanwhile, FIG. 13 shows the dissolution profiles for LPF-4, LPF-8, LPF-9, LPF-12, LPF-13, LPF-16 and the physical mixture pellet formulation at a pH of 1.2. From these results, it is clear that the amount of water added as a pre-extrusion/granulating liquid and co-solvent concentration has an effect on the drug release rate on liqui-pellet. In general, reduced water content (as in formulations LPF-12, LPF-13 and LPF-16) increases drug release rate, and increased tween 80 concentration (as in formulations LP-9 and LPF-13) increases drug release rate. In support of this, Table 13 demonstrates the effect that the amount of water added as a pre-extrusion/granulating liquid has on the rate of release is provided below.

TABLE 13

Mean % cumulative drug release at pH 1.2 after
1.2 hours for a variety of formulations

| Formulation | Water content of extrudate (% w/w) | Mean % cumulative drug release at pH 1.2 after two hours |
|---|---|---|
| LPF-4 | 30.00 | 21.86 |
| LPF-8 | 19.22 | 25.59 |
| LPF-12 | 8.68 | 34.50 |
| LPF-16 | 4.53 | 38.01 |

It will be appreciated that LPF-4, LPF-8, LPF-12 and LPF-16 all comprised 32 wt % co-solvent, and so the only variable was the amount of water added as a pre-extrusion liquid. Accordingly, it will be appreciated that reducing the amount of water clearly increases the drug release rate.

Similarly, the extrudates of LPF-12 and LPF-13 comprised 8.68 wt % water. However, LPF-12 contained 32 wt % tween 80, after drying, and LPF-13 contained 36 wt % tween 80, after drying. After two hours, the mean cumulative drug release at pH 1.2 for LPF-12 was 34.50% and for LP-13 it was 46.44%. Accordingly, it will be appreciated that increasing the amount of tween 80 increases the drug release rate. A less marked effect is observed for LPF-8 and LPF-9. Accordingly, it appears that changes in the concentration of the tween 80 have a greater effect on drug release rate when the amount of water used as a pre-extrusion/granulating liquid is lower.

Finally, it is noted that LPF-13 where the formulation comprised only 8.68 wt % water, and had a tween 80 concentration of 36 wt %, had the fastest drug release rate of the formulations tested.

As shown in FIG. 12, LPF-4, LPF-8. LPF-9, LPF-12, LPF-13 and LPF-16 all have fast dissolution rates at pH 7.4, with the rate starting to plateau after ~25 min.

Conclusion

The amount of water and tween 80 in liqui-pellet formulation are important parameters, which influences drug release rate. The reduction of water content effectively reduces cohesive strength of the liqui-pellet, improving its disintegrating properties and enhancing drug release rate. The increase in tween 80 concentration increases the proportion of drug being in solubilized or molecularly dispersed state, which increases surface available for dissolution. Also, tween 80 reduces surface tension or cohesive force, improving disintegration; hence, enhancing drug release rate.

Despite reducing water and increasing tween 80 content resulting in faster drug release rate, there is a limit of how much water can be reduced and tween 80 can be increased. Outside of this limit the formulation is likely to fail to produce liqui-pellet due to agglomeration.

Example 4: Investigating the Effect of the Ratio of Coating Material and Carrier on the Liqui-Pellet The inventors decided to investigate the influence of the ratio of carrier and coating material on liqui-pellet, particularly on the drug release rate.

Material and methods Materials Naproxen was obtained from Tokyo Chemical Industry Co (Japan). Other excipients used to prepare the liqui-pellet included microcrystalline cellulose (avicel PH-101), (FMC corp., UK); colloidal silicon dioxide (aerosil 300), (Evonik Industries AG, Hanau, Germany); liquid nitrogen; sodium starch glycolate Type A (primojel), (DFE Pharma, Goch, Germany) and polysorbate 80 (tween 80), (Acros, Netherlands). All other reagents and solvent were of analytical grades.

Preparation of Naproxen Liqui-Pellet

The preparation of liqui-pellet involved solubilizing 25 mg of naproxen in a specified amount of tween 80 (non-volatile co-solvent) using pestle and mortar. Once naproxen was well mixed and solubilized, specified amount of avicel (carrier) was added and further mixed. The admixture was then transferred into a mixer (Caleva Multitab, Caleva Process Solutions Ltd, UK), where primogel (concentration of 5% w/w) was added to improve disintegration of formulation. The admixture was then mixed/granulated under a constant rate of 125 rpm for 7 min with specified amount of deionized water added bit by bit. At this point aerosil 300 (coating material) was added into the wet mass and further undergo another 7 min of mixing/granulating. The wet mass was then extruded and spheronized at an almost constant rotation at 4000 rpm (decrease to 2500 rpm if agglomeration seemed likely or increase to 4500 rpm to increase pellet sphericity), however in each formulation, spheronization time varied depending on the extrudate plasticity property. The key parameters that were varied were water content, tween 80 concentration and R-value. Some formulation extrudates were frozen in a freezer, frozen due to being placed in liquid nitrogen or were sphereonized little by little.

Details of each formulation are given in Table 14.

Table 14a: Key extrudate characteristics of NLP-1 to NLP-14

| Formulation | Water conc in extrudate (% w/w) | Liquid vehicle conc in extrudate (% w/w) | Liquid load factor | Carrier conc in extrudate (% w/w) | Coating conc in extrudate (% w/w) | Ratio of carrier to coating material (R value) |
|---|---|---|---|---|---|---|
| Physical mixture pellet | 37.5 | | | 42.24 | 2.11 | 20:01 |
| NLP-1 | 30 | 25.2 | 1.38 | 25.66 | 2.7 | 19:02 |
| NLP-2 | 19.22 | 32.31 | 1.63 | 26.77 | 2.81 | 19:02 |
| NLP-3 | 19.22 | 32.31 | 1.63 | 26.77 | 2.81 | 19:02 |
| NLP-4 | 8.68 | 36.53 | 1.63 | 30.26 | 3.18 | 19:02 |
| NLP-5 | 8.68 | 36.53 | 1.63 | 30.26 | 3.18 | 19:02 |
| NLP-6 | 8.68 | 36.53 | 1.63 | 30.26 | 3.18 | 19:02 |
| NLP-7 | 4.53 | 34.37 | 1.38 | 35 | 3.68 | 19:02 |
| NLP-8 | 4.53 | 34.37 | 1.38 | 35 | 3.68 | 19:02 |
| NLP-9 | 19.22 | 29.08 | 1.38 | 31.28 | 1.56 | 20:01 |
| NLP-10 | 19.22 | 29.08 | 1.38 | 29.61 | 3.12 | 19:02 |
| NLP-11 | 19.22 | 29.08 | 1.38 | 27.55 | 4.59 | 06:01 |
| NLP-12 | 8.68 | 32.88 | 1.38 | 35.36 | 1.77 | 20:01 |
| NLP-13 | 8.68 | 32.88 | 1.38 | 33.48 | 3.52 | 19:02 |
| NLP-14 | 8.68 | 32.88 | 1.38 | 31.14 | 5.19 | 06:01 |

| Formulation | Superdisintegrant conc in extrudate (% w/w) | Naproxen conc in extrudate (% w/w) | Additional treatment | Successfully spheronized into pellet? (Yes/No) |
|---|---|---|---|---|
| Physical mixture pellet | | 18.16 | | Yes |
| NLP-1 | 3.50 | 12.94 | | No |
| NLP-2 | 4.04 | 14.85 | | No |
| NLP-3 | 4.04 | 14.85 | Froze in freezer | No |

-continued

| | | | | |
|---|---|---|---|---|
| NLP-4 | 4.57 | 16.79 | | No |
| NLP-5 | 4.57 | 16.79 | Froze in freezer | No |
| NLP-6 | 4.57 | 16.79 | Sphronized little by little | Yes |
| NLP-7 | 4.77 | 17.64 | | No |
| NLP-8 | 4.77 | 17.64 | Treated with liquid nitrogen | No |
| NLP-9 | 4.04 | 14.82 | | Yes |
| NLP-10 | 4.04 | 14.93 | | Yes |
| NLP-11 | 4.04 | 15.52 | | Yes |
| NLP-12 | 4.57 | 16.75 | | Yes |
| NLP-13 | 4.57 | 16.88 | | Yes |
| NLP-14 | 4.57 | 17.55 | | Yes |

Table 14b: Key formulation characteristics of the formulations which successfully spheronized

| Formulation | Liquid vehicle conc after drying (% w/w) | Liquid load factor | Carrier conc after drying (% w/w) | Coating conc after drying (% w/w) | Ratio of carrier to coating material (R value) |
|---|---|---|---|---|---|
| Physical mixture pellet | | | 67.58 | 3.37 | 20:1 |
| NLP-6 | 40 | 1.63 | 33.14 | 3.48 | 19:2 |
| NLP-9 | 36 | 1.38 | 38.72 | 1.94 | 20:1 |
| NLP-10 | 36 | 1.38 | 36.66 | 3.86 | 19:2 |
| NLP-11 | 36 | 1.38 | 34.10 | 5.68 | 6:1 |
| NLP-12 | 36 | 1.38 | 38.72 | 1.94 | 20:1 |
| NLP-13 | 36 | 1.38 | 36.66 | 3.86 | 19:2 |
| NLP-14 | 36 | 1.38 | 34.10 | 5.68 | 6:1 |

| Formulation | Superdisintegrant conc after drying (% w/w) | Naproxen conc after drying (% w/w) | Total weight of 25mg naproxen liqui-pellet (mg) |
|---|---|---|---|
| Physical mixture pellet | | 29.05 | 85.03 |
| NLP-6 | 5 | 18.38 | 131.25 |
| NLP-9 | 5 | 18.34 | 132.7 |
| NLP-10 | 5 | 18.48 | 131.25 |
| NLP-11 | 5 | 19.22 | 128.63 |
| NLP-12 | 5 | 18.34 | 132.7 |
| NLP-13 | 5 | 18.48 | 131.25 |
| NLP-14 | 5 | 19.22 | 128.63 |

Particle Size Analysis

Particle size analysis was carried out to all successful formulation (except for NLP-6 as its surface was too cohesive/sticky for this test) using sieve method. Formulation of liqui-pellet weighing 5 g were placed in a sieve (Test sieve, Retsch, Germany). The sieve size that were used were 2000, 1000, 850, 500 and 250 μm. The sieve then placed on a mechanical shaker (AS 200, Retsch, Germany), which was set under constant vibration with amplitude of 60 for 1 min, then a further 9 min with amplitude of 40. The size distribution of liqui-pellet was determined based on pellet fraction between 250 μm and 2000 μm and shown as the % of total pellet weight.

The remaining methods were the same as described in Example 1.

Results and Discussion

Success of spheronizing formulation Formulations NLP-6 and NLP-9 to NLP-14 were successfully made into liqui-pellets.

The rest of the formulations agglomerated during spheronization due to the extrudate surface being too cohesive/sticky.

Formulations NLP-9 to NLP-14 have different R-values but were all able to be spheronize into liqui-pellet. Accordingly, the ratio of carrier and coating material does not seem to have an observable effect on the success of the liqui-pellet production.

It is noted that freezing the extrudate in a freezer or with liquid nitrogen did not improve the ability of the extrudate to be spheronised into liqui-pellets.

Particle Size of Formulated Liqui-Pellet Via Sieve Method

Results obtained from the particle size analysis are shown in table 15.

TABLE 15

Size distribution of pellets with varying R values

| | | % weight of pellets | | | | |
|---|---|---|---|---|---|---|
| Formulation | R-value | 250 μM | 500 μM | 850 μM | 1000 μM | 2000 μM |
| NLP-9 | 20:1 | 0.00 | 64.25 | 32.45 | 2.82 | 0.00 |
| NLP-10 | 19:2 | 2.90 | 96.56 | 0.70 | 0.00 | 0.00 |
| NLP-11 | 6:1 | 26.76 | 72.71 | 0.59 | 0.00 | 0.00 |
| NLP-12 | 20:1 | 0.49 | 97.71 | 1.69 | 0.06 | 0.00 |
| NLP-13 | 19:2 | 0.44 | 96.46 | 3.04 | 0.17 | 0.00 |
| NLP-14 | 6:1 | 0.00 | 98.83 | 1.06 | 0.00 | 0.00 |

The extrudates of NLP-9, NLP-10 and NLP-11 all contained 19.22 wt % water, and once dried contained 36% w/w tween 80. However, the R-values are different, and this appears to affect the pellet size; the smaller the R-value, the higher the proportion of smaller size pellets.

However, the trend of decreasing pellet size on decreasing R-value is not observed for the extrudates containing 8.68 wt % water, and 36 wt % co-solvent after drying (i.e. NLP-12, NLP-13 and NLP-14). This could indicate that when a small amount of water content is used, the effect of the R-value on liqui-pellet size is reduced.

Flow Properties

NLP-6 liqui-pellet surface was too cohesive/sticky for flowability testing. The physical mixture and NLP-9 to NLP-14 underwent flowability test, and the results are shown in table 16.

TABLE 16

Flow rate (g/sec), Angle of repose and Carr's compressible index (CI %) of physical mixture formulation and NLP-9 to NLP-14

| Formulation | Flow Rate (g/sec) ± SD | Angle of repose ± SD | CI % ± SD | Inference according to Angle of repose | Inference according to CI % |
|---|---|---|---|---|---|
| Physical mixture pellet | 10.72 ± 0.33 | 19.96 ± 1.43 | 11.11 ± 0.62 | Excellent flowability | Good flowability |
| NLP-9 | 7.07 ± 0.11 | 27.65 ± 1.00 | 6.31 ± 0.70 | Excellent flowability | Excellent flowability |
| NLP-10 | 5.28 ± 0.06 | 32.74 ± 0.40 | 6.38 ± 1.20 | Good flowability | Excellent flowability |
| NLP-11 | 3.96 ± 0.18 | 36.51 ± 0.95 | 8.44 ± 1.21 | Good-fair flowability | Excellent flowability |
| NLP-12 | 6.4 ± 0.19 | 29.52 ± 0.85 | 3.96 ± 0.00 | Excellent flowability | Excellent flowability |
| NLP-13 | 6.10 ± 0.09 | 29.29 ± 0.50 | 4.48 ± 1.27 | Excellent flowability | Excellent flowability |
| NLP-14 | 6.09 ± 0.18 | 30.35 ± 0.58 | 6.01 ± 1.14 | Excellent-good flowability | Excellent flowability |

All of the tested formulations showed excellent, excellent-good or good-fair flow properties.

Dissolution Studies

Figure 15:
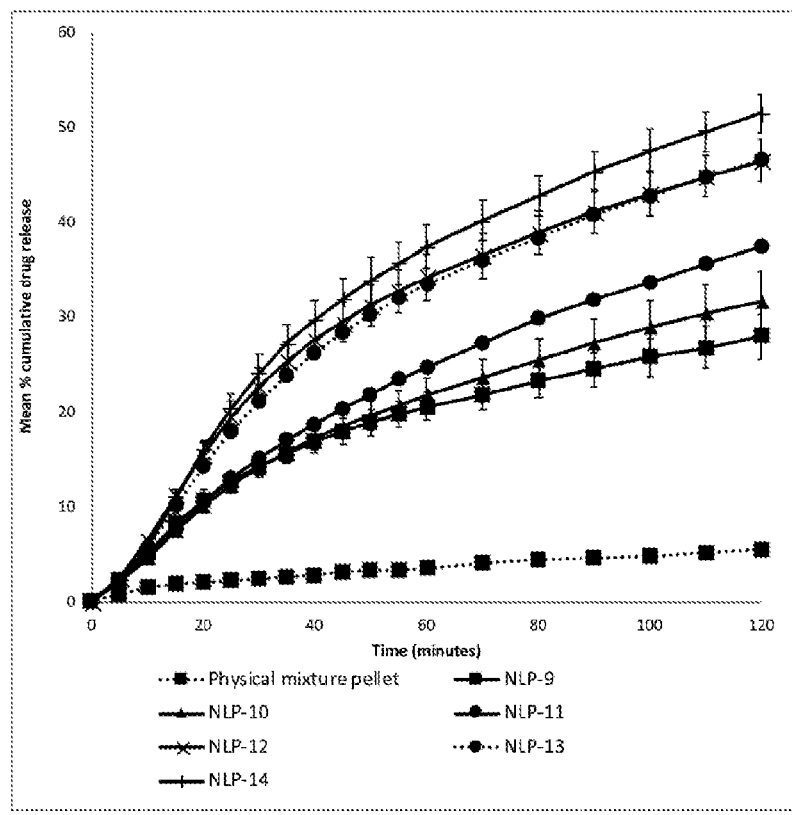
FIG. 15 is a graph showing the dissolution of formulations NLP-9 to NLP-14 and the physical mixture pellet formulation at pH 1.2.

As shown in FIG. 15, extrudates containing 8.68 wt % of water (NLP-12, NLP-13 and NLP-14) have faster drug release rate than extrudates containing 19.22 wt % of water (NLP-9, NLP-10 and NLP-11), this is in line with the results obtained in Example 3.

FIG. 15 also indicates that almost all of the formulations show a general trend that reduction in R-value (or increased aerosil and decrease avicel ratio) increases the dissolution rate.

Accordingly, it seems that the R-value has an effect on drug release rate, although this is less pronounced than the effect of varying the water content or co-solvent concentration.

Conclusion

The data obtained from this investigation suggest that the ratio of avicel (carrier) and aerosil (coating material) does not have a major effect on the success of liqui-pellet production. However, the R-value appears to affect the size of the pellets produced, particularly when the water content is high.

Furthermore, the dissolution studies show that increased aerosil and decrease avicel ratio increases the dissolution rate. However, the effect of varying the R-value on dissolution rate is less pronounced than the effect of varying the water content or co-solvent concentration.

Example 5: Investigating the Effect of an Effervescent Agent on the Liqui-Pellet The inventors decided to investigate whether the inclusion of an effervescent agent would affect the properties of the liqui-pellet formulations.

Materials and Methods

Materials

Naproxen was obtained from Tokyo Chemical Industry Co (Japan). Other excipients used to prepare the liqui-pellet included microcrystalline cellulose (avicel PH-101), (FMC corp., UK); colloidal silicon dioxide (aerosil 300), (Evonik Industries AG, Hanau, Germany); sodium starch glycolate Type A (primojel), (DFE Pharma, Goch, Germany), sodium bicarbonate, (Acros, New Jersey, USA); synthetic magnesium alumino-metasilicate (Neusilin US2), (Fuji Chemicals, Japan) and polysorbate 80 (tween 80), (Acros, Netherlands). All other reagents and solvent were of analytical grades.

Preparation of Naproxen Effervescent Liqui-Pellet

The liquid medication was prepared by mixing naproxen with tween 80 using the pestle and mortar method. The liquid medication was then incorporated into avicel PH-101 (carrier) along with specified amount NaHCO₃ (effervescent agent) and primojel (superdisintegrant) and mixed for 2 min at a constant rate of 125 rpm (Caleva Multitab, Caleva Process Solutions Ltd, UK). Specified amount of deionized water, which was the granulation liquid, was then incorporated into the admixture bit by bit to achieve reasonable plastic property for extrusion (Caleva Multitab, Caleva Process Solutions Ltd, UK). The duration of mixing of the admixture with granulation liquid was 5 min. Aerosil 300 (coating material) was then added into the admixture and further mixed for 5 min before extrusion. Once the sample was extruded, the extrudate was spheronized at an almost constant rotation at 4000 rpm (decrease to 2000 rpm if agglomeration seems likely). The spheronization time varied depending on the extrudate's plastic property to avoid agglomeration. The spheroids were then placed in an oven under a constant temperature of 40° C. overnight to remove water content.

Apart from the different concentrations of NaHCO₃ and water content, all other compositions were kept constant for all formulation, and the carrier to coating ratio was kept constant at 20:1 respectively. Details of each formulation are given in Table 17.

TABLE 17

| a: Key formulation characteristics of extrudate of F-1 to F-5 | | | | |
|---|---|---|---|---|
| Formulation | Water content in extrudate (% w/w) | Liquid vehicle conc in extrudate (% w/w) | Carrier conc in extrudate (% w/w) | Coating conc in extrudate (% w/w) |
| Physical mixture pellet | 37.88 | | 40.13 | 2.00 |
| F-1 | 27.95 | 20.76 | 34.62 | 1.74 |
| F-2 | 20.24 | 19.54 | 32.64 | 1.64 |
| F-3 | 18.23 | 17.74 | 29.42 | 1.48 |
| F-4 | 22.77 | 14.85 | 24.78 | 1.25 |
| F-5 | 18.67 | 13.09 | 21.84 | 1.10 |

| Formulation | Superdisintegrant conc in extrudate (% w/w) | Sodium bicarbonate conc in extrudate (% w/w) | Naproxen conc in extrudate (% w/w) |
|---|---|---|---|
| Physical mixture pellet | 2.75 | | 17.25 |
| F-1 | 3.27 | 3.91 | 13.84 |
| F-2 | 3.08 | 9.53 | 13.05 |
| F-3 | 2.79 | 17.89 | 11.76 |
| F-4 | 2.34 | 25.00 | 9.90 |
| F-5 | 2.06 | 33.90 | 8.73 |

| b: Key formulation characteristics of F-1 to F-5 | | | | |
|---|---|---|---|---|
| Formulation | Liquid vehicle conc. after drying (% w/w) | Carrier conc. after drying (% w/w) | Coating conc. after drying (% w/w) | Super-disintegrant conc. after drying (% w/w) |
| Physical mixture pellet | | 64.20 | 3.20 | 4.40 |
| F-1 | 26.56 | 44.29 | 2.23 | 4.18 |
| F-2 | 24.63 | 41.09 | 2.07 | 3.87 |
| F-3 | 21.82 | 36.17 | 1.82 | 3.43 |
| F-4 | 19.02 | 31.71 | 1.60 | 2.99 |
| F-5 | 16.23 | 27.06 | 1.36 | 2.55 |

| Formulation | Sodium bicarbonate conc after drying (% w/w) | Naproxen conc after drying (% w/w) | Total weight of 25 mg naproxen liqui-pellet (mg) |
|---|---|---|---|
| Physical mixture pellet | | 27.60 | 90.58 |
| F-1 | 5 | 17.71 | 141.2 |
| F-2 | 12 | 16.43 | 152.2 |
| F-3 | 22 | 14.46 | 172.9 |
| F-4 | 32 | 12.68 | 197.2 |
| F-5 | 42 | 10.82 | 231.1 |

All formulations had a liquid load factor of 1.

The remaining methods were the same as described in Example 1.

Results and Discussion

Preparation of Naproxen Effervescent Liqui-Pellet

All formulations were successfully made into a pellet form. It is observed that liqui-pellet formulations F-4 and F-5 required more granulating liquid than the other formulations to produce liqui-pellet. This is because these two formulations have the two highest amount of $NaHCO_3$ content, which means that the admixture contains a larger amount of powder and more granulating liquid is required to obtain reasonable plastic property of wet mass for extrusion.

The fact that liqui-pellet can contain 42 wt % of $NaHCO_3$ in the dosage form is surprising. The previous liquisolid technology did not allow such a large amount of a functional excipient to be added whilst maintaining good dosage size and mass for Swallowing.

Flowability Studies

The physical mixture and F-1 to F-5 underwent flowability test, and the results are shown in table 18.

dissolution rate. Accordingly, 32% $NaHCO_3$ seems sufficient for drug release enhancement. In fact, the drug release rate of F-4 and F-5 is superior to the formulations tested in the previous examples. The $NaHCO_3$ enhances the dissolution rate by disrupting diffusion boundary layer, promoting disintegration and modulating the pH and microenvironment.

Conclusion

The inventors have shown that it is possible to incorporate an effervescent agent into the liqui-pellet formulation, whilst achieving excellent or good flowability and maintaining the overall dosage in a small enough form for swallowing. For instance, with 42% w/w $NaHCO_3$ in the total liqui-pellet mass, the total liqui-pellet mass in the capsule was only 231 mg.

The dissolution results show a remarkable increase in drug release rate with $NaHCO_3$. Furthermore, when the $NaHCO_3$ concentration increases, so does the dissolution rate.

TABLE 18

Flow rate (g/sec), Angle of repose and Carr's compressible index (CI %) of physical mixture formulation and F1-F5

| Formulation | Flow Rate (g/sec) ± SD | Angle of repose ± SD | CI % ± SD | Inference according to Angle of repose | Inference according to CI % |
|---|---|---|---|---|---|
| Physical mixture pellet | 10.72 ± 0.33 | 19.96 ± 1.43 | 11.11 ± 0.62 | Excellent flowability | Good flowability |
| F-1 | 6.77 ± 0.49 | 28.95 ± 1.62 | 10.82 ± 1.33 | Excellent flowability | Excellent-good flowability |
| F-2 | 7.55 ± 0.21 | 26.98 ± 0.37 | 9.85 ± 0.00 | Excellent flowability | Excellent flowability |
| F-3 | 8.35 ± 0.25 | 25.37 ± 0.68 | 11.32 ± 0.65 | Excellent flowability | Good flowability |
| F-4 | 8.10 ± 0.17 | 26.71 ± 0.20 | 10.23 ± 0.00 | Excellent flowability | Excellent-good flowability |
| F-5 | 8.10 ± 0.19 | 27.84 ± 0.05 | 10.01 ± 0.00 | Excellent flowability | Excellent-good flowability |

All formulations showed excellent, excellent-good or good flow properties.

Particle Size Studies

All of the liquid-pellet formulations have a narrow size distribution. This suggests that increasing the $NaHCO_3$ content in liqui-pellet formulation does not seem to have an effect on its size.

Dissolution Studies

Figure 16:
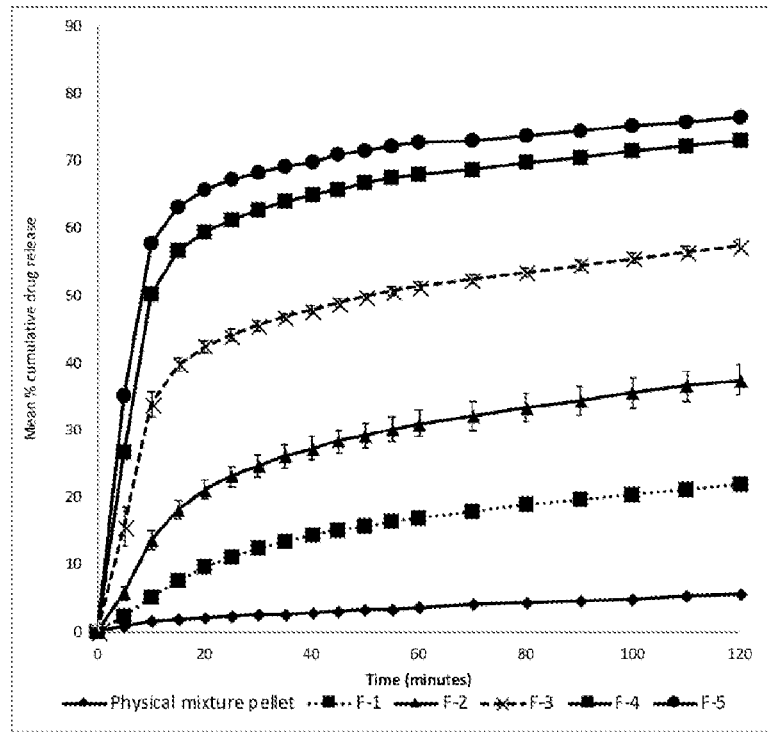
FIG. 16 is a graph showing the dissolution of formulations F-1 to F-5 and the physical mixture pellet formulation at pH 1.2.

FIG. 16 shows the results from the dissolution studies at pH 1.2. This shows a marked increase of drug release rate for formulation F-4 ($NaHCO_3$ 32% w/w) and F-5 ($NaHCO_3$ 42% w/w) in comparison to physical mixture pellet. The cumulative dissolution rate of F-4 after 2 h is ~64% higher than the physical mixture and F-5 is ~71% higher than physical mixture. This shows that $NaHCO_3$ is an effective functional excipient in naproxen liqui-pellet for enhanced drug release.

F-4 (32% $NaHCO_3$) and F-5 (42% $NaHCO_3$) did not show a significant difference in the dissolution profile. This suggests that there is a limit of $NaHCO_3$ concentration that can cause a noticeable improvement of drug release rate; above this limit, $NaHCO_3$ have less influence on liqui-pellet Example 6: Producing Exploding Liqui-Pellet for Rapid Drug Release Materials and Methods The materials used were as set out in example 5.

Preparation of Naproxen Effervescent Liqui-Pellet

All liqui-pellet formulations were prepared in a similar manner except for the variation in parameters such as: carrier composition; tween 80 concentration, water content and liquid load factor, as given in table 19 below. The liquid medication was prepared by adding a specified amount of naproxen (API) and tween 80 (liquid vehicle) into a mortar then mixing it with a pestle. The liquid medication was then incorporated into specified carrier material where 32% w/w $NaHCO_3$ (effervescent agent) and primojel (superdisintegrant) was added. The admixture was mixed for 2 min at a constant rate of 125 rpm (Caleva Multitab, Caleva Process Solutions Ltd, UK). The primojel was added intragranularly. Specified amount of granulating liquid (deionized water) was added bit by bit to achieve reasonable plastic property for extrusion (Caleva Multitab, Caleva Process Solutions Ltd, UK). The duration of mixing of the admixture with granulating liquid was 5 min. Aerosil 300 (coating material) was then added into the admixture and further mixed for 5 min before extrusion. Once the sample was extruded, the extrudate was spheronized at an almost constant rotation at 4000 rpm (decrease to 2000 rpm if agglomeration seemed likely). The spheronization time varied depending on the extrudate's plastic property to avoid agglomeration. The pellets were then placed in an oven under a constant temperature of 40° C. overnight to remove water content.

Furthermore, the physical mixture pellet was prepared in a similar manner as above including 32% w/w $NaHCO_3$, but without liquid vehicle incorporated. All formulation's carrier to coating material ration were kept constant at 20:1 respectively.

TABLE 19 a: Key formulation characteristics of extrudate of F-6 to F-12

| Formulation | Water content in extrudate (% w/w) | Liquid vehicle conc in extrudate (% w/w) | Liquid load factor | Carrier type | Carrier conc in extrudate (% w/w) |
|---|---|---|---|---|---|
| Physical mixture pellet | 25.93 | | | 100% avicel PH101 | 31.80 |
| F-6 | 21.88 | 14.84 | 1 | 100% avicel PH101 | 24.78 |
| F-7 | 13.83 | 18.10 | 1.14 | 100% avicel PH101 | 25.47 |
| F-8 | 13.49 | 19.90 | 1.23 | 100% avicel PH101 | 24.15 |
| F-9 | 7.41 | 25.00 | 1.65 | 100% avicel PH101 | 22.33 |
| F-10 | 24.24 | 14.39 | 1 | 100% avicel PH101 | 24.03 |
| F-11 | 13.79 | 16.38 | 1 | 50% avicel PH101 & 50% neusilin US2 | 27.34 |
| F-12 | 13.79 | 19.83 | 1.23 | 50% avicel PH101 & 50% neusilin US2 | 24.07 |

| Formulation | Coating conc in extrudate (% w/w) | Primojel conc in extrudate (% w/w) | Sodium bicarbonate conc in extrudate (% w/w) | Naproxen conc in extrudate (% w/w) | Successfully spheronized into pellet? (Yes/No) |
|---|---|---|---|---|---|
| Physical mixture pellet | 1.59 | 3.24 | 23.70 | 13.69 | Yes |
| F-6 | 1.25 | 2.35 | 25.00 | 9.90 | Yes |
| F-7 | 1.27 | 2.59 | 27.57 | 10.97 | Yes |
| F-8 | 1.21 | 3.37 | 27.68 | 10.97 | Yes |
| F-9 | 1.11 | 2.78 | 29.63 | 11.74 | No |
| F-10 | 1.21 | 2.27 | 24.24 | 9.60 | No |
| F-11 | 1.38 | 2.59 | 27.59 | 10.93 | Yes |
| F-12 | 1.20 | 2.59 | 27.59 | 10.93 | Yes | b: Key formulation characteristics of formulations which were successfully spheronized

| Formulation | Liquid vehicle conc after drying (% w/w) | Liquid load factor | Carrier type | Carrier conc after drying (% w/w) | Coating conc after drying (% w/w) |
|---|---|---|---|---|---|
| Physical mixture pellet | | | 100% avicel PH101 | 42.93 | 2.14 |
| F-6 | 19.00 | 1.00 | 100% avicel PH101 | 31.71 | 1.60 |
| F-7 | 21.00 | 1.14 | 100% avicel PH101 | 29.56 | 1.48 |
| F-8 | 23.00 | 1.23 | 100% avicel PH101 | 27.92 | 1.39 |
| F-11 | 19.00 | 1.00 | 50% avicel PH101 & 50% neusilin US2 | 31.71 | 1.60 |
| F-12 | 23.00 | 1.23 | 50% avicel PH101 & 50% neusilin US2 | 27.92 | 1.39 |

TABLE 19-continued

| Formulation | Primojel conc after drying (% w/w) | Sodium bicarbonate conc after drying (% w/w) | Naproxen conc after drying (% w/w) | Total weight of 25 mg naproxen liqui-pellet (mg) |
|---|---|---|---|---|
| Physical mixture pellet | 4.37 | 32.00 | 18.48 | 135.25 |
| F-6 | 3.00 | 32.00 | 12.68 | 197.20 |
| F-7 | 3.01 | 32.00 | 12.73 | 196.41 |
| F-8 | 3.90 | 32.00 | 12.68 | 197.20 |
| F-11 | 3.00 | 32.00 | 12.68 | 197.20 |
| F-12 | 3.00 | 32.00 | 12.68 | 197.20 |

All of the formulations contained 25 mg of naproxen, 32% w/w NaHCO$_3$ and carrier to coating material ratio were kept constant at 20:1 respectively.

The remaining methods were the same as described in Example 1.

Results and Discussion

Preparation of Naproxen Effervescent Liqui-Pellet

All liqui-pellet formulations were successfully formed except for F-9 and F-10. However, it is noted that Formulation F-9 has the highest amount of tween 80 of 27% w/w and F-10 has the highest amount of water with 24.24 wt % in the extrudate.

Formulation F-11 and F-12 use 50% avicel PH101 and 50% Neusilin US2 as carrier material, which gave the pre-extrusion admixture a remarkably smooth flow during extrusion process. Usually the wet mass would be cohesive like a sticky paste which requires some intervention to process the wet mass through the machine for extrusion. However, F-11 and F-12 pre-extrusion admixtures flowed smoothly through the machine, and did not require intervention, such as pushing the wet mass into the extruder. Neusilin US2 has high specific surface of 300 m$^2$/g and high oil adsorption capacity of 3.2 ml/g. This may be the reason for the smooth flow of pre-extrusion admixture.

Flowability Studies

The physical mixture and F-6 to F-8, F11 and F12 underwent flowability test, and the results are shown in table 20.

TABLE 20

Flow rate (g/sec), Angle of repose and Carr's compressible index (CI %) of physical mixture pellet and F-6 to F-8, F-11 and F-12

| Formulation | Flow Rate (g/sec) ± SD | Angle of repose ± SD | CI % ± SD | Inference according to Angle of repose | Inference according to CI % |
|---|---|---|---|---|---|
| Physical mixture pellet | 8.75 ± 0.19 | 24.39 ± 0.56 | 13.32 ± 0.00 | Excellent flowability | Good flowability |
| F-6 | 8.10 ± 0.17 | 26.71 ± 0.20 | 10.23 ± 0.00 | Excellent flowability | Excellent to good flowability |
| F-7 | 8.12 ± 0.27 | 27.32 ± 0.44 | 10.33 ± 0.57 | Excellent flowability | Excellent to good flowability |
| F-8 | 7.81 ± 0.28 | 28.92 ± 0.49 | 10.33 ± 1.14 | Excellent flowability | Excellent to good flowability |
| F-11 | 7.86 ± 0.19 | 28.58 ± 1.00 | 11.17 ± 0.00 | Excellent flowability | Good flowability |
| F-12 | 8.37 ± 0.11 | 26.83 ± 0.79 | 10.23 ± 0.00 | Excellent flowability | Excellent to good flowability |

All formulations obtain excellent, excellent to good or good flow properties.

Particle Size Studies

All of the Liqui-Pellet Formulations have a Narrow Size Distribution.

Drug Release Studies

Figure 17:
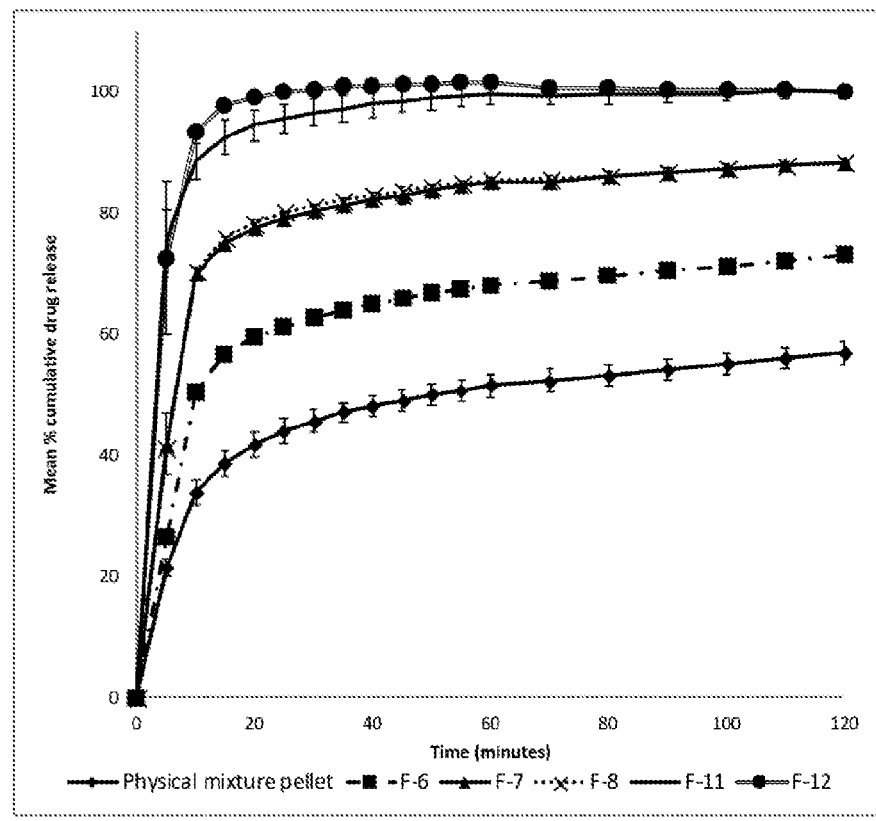
FIG. 17 is a graph showing the dissolution of formulations F-6 to F-8, F-11 and F-12 and the physical mixture pellet formulation at pH 1.2.

As shown in FIG. 17, the optimized naproxen effervescent liqui-pellet formulation F-11 and F-12 show a remarkable enhanced release dissolution profile at pH 1.2.

Formulation F-12 drug release rate was extremely fast, with the cumulative drug release nearing 100% at 10 min at pH 1.2. Formulation F-12 has been optimized by using the upper limit of tween 80 concentration (2300 w/w) and lower limit of water content (13.79 wt % in the extrudate).

However, the single most significant factor contributing to F-12's remarkable rapid and explosive drug release other than NaHCO$_3$, is the use of neusilin US2 in the formulation.

Formulation F-11 also shows a very fast dissolution profile similar to F-12. Despite F-11 having lower tween 80 concentration (19% w/w) than F-12 (23% w/w). Again, this supports the view that neusilin US2 seems to be a major factor in drug release enhancement.

Meanwhile, it is observed that an increased in tween 80 and reduction in water content increases the drug release rate. For instance, F-7 (containing 21% w/w tween 80, when dried, and the extrudate contained 13.83 wt % water) shows faster dissolution rate than F-6 (containing 19% w/w tween 80, when dried, and the extrudate contained 21.88 wt % water) by ~15% after 2 h. However, F-8 (containing 23% w/w tween 80, when dried, and the extrudate contained 13.49 wt % water) and F-7 (containing 21% w/w tween 80, when dried, and the extrudate contained 13.83 wt % water) have similar dissolution profiles, indicating that the effect is diminished above about 21% w/w tween 80.

Conclusion

The inventors have shown that liqui-pellet is capable of explosive and rapid drug release. In particular, naproxen liqui-pellets can achieve 100% drug release within 20 min at an acidic pH of 1.2.

It appears that the key factors contributing to this remarkable dissolution profile are the use of an effervescent agent (NaHCO$_3$) and neusilin US2 in the liqui-pellet formulation.

Furthermore, as mentioned above, F-11 and F-12 pre-extrusion admixtures flowed smoothly through the machine. The inventors postulate that this is due to the use of a high specific surface area carrier, such as neusilin US2, together with microcrystalline cellulose (MCC), such as avicel PH-102.

Example 7: Using Liqui-Pellet Technique to Enhance Dissolution Rate of Hydrochlorothiazide The inventors decided to test the liqui-pellet dosage form with hydrochlorothiazide (HCTZ), an alternative API with poor water solubility.

Materials and Methods

Materials

Hydrochlorothiazide was obtained from Spectrum Chemical MFG Corp (USA). Other excipients used to prepare the liqui-pellet included microcrystalline cellulose (avicel PH-101), (FMC corp., UK); colloidal silicon dioxide (aerosil 300), (Evonik Industries AG, Hanau, Germany); sodium starch glycolate Type A (primojel), (DFE Pharma, Goch, Germany); synthetic magnesium alumino-metasilicate (Neusilin US2), (Fuji Chemicals, Japan); polysorbate 80 (tween 80), (Acros, Netherlands); propylene glycol (SAFC, Spain); polyethylene glycol 200 (PEG 200), (Fisher Scientific, Leicester, UK) and macrogolglycerol ricinoleate 35 (Kolliphor EL), (BASF SE, Ludwigshafen, Germany). All other reagents and solvent were of analytical grades.

Solubility Studies

Saturation solubility studies were carried out in a similar manner to example 1. However, the liquid vehicles that were used were: tween 80; propylene glycol (PG); kolliphor EL and polyethylene glycol 200 (PEG 200). Also, the duration of time that the sample was left in the bath shaker was longer (96 h).

Preparation of HCTZ 12.5 mg Liqui-Pellet

All liqui-pellet formulations were prepared in a similar manner except for the variation in parameters such as: carrier composition; types of liquid vehicle and water content, see table 21 below. The liquid medication was prepared by mixing a specified amount of HCTZ with specified liquid vehicle using a mortar and pestle. The liquid medication was then incorporated into specified carrier material which could be 100% avicel PH101, 100% avicel PH102 or a mixture of 50% avicel PH102 and 50% neusilin US2.

All formulations made had 5.5% w/w primojel (superdisintegrant) and carrier to coating ratio of 20:1 respectively. The coating material used was aerosil 300. Apart from physical mixture pellet, all liqui-pellet formulation had 34% w/w of specified liquid vehicle and a liquid load factor (Lf) of 0.79.

The liquid medication along with carrier and primojel were mixed 2 min at a constant rate of 125 rpm (Caleva Multitab, Caleva Process Solutions Ltd, UK). The primojel was added intragranularly. Specified amount of granulating liquid (deionized water) was added bit by bit to achieve reasonable plastic property for extrusion (Caleva Multitab, Caleva Process Solutions Ltd, UK). The duration of mixing of the admixture with granulating liquid was 5 min. Aerosil 300 was then added into the admixture and further mixed for 5 min before extrusion. Once the sample was extruded, the extrudate was spheronized at an almost constant rotation at 4000 rpm (decrease to 2000 rpm if agglomeration seems likely). The spheronization time varied depending on the extrudate's plastic property to avoid agglomeration. The pellets were then placed in an oven under a constant temperature of 40° C. overnight to remove water content.

TABLE 21 a: Key formulation characteristics of extrudate of F-13 to F-20

| Formulation | Water conc. in extrudate (% w/w) | Liquid vehicle | Liquid vehicle conc. in extrudate (% w/w) | Carrier type |
|---|---|---|---|---|
| Physical mixture pellet | 52.94 | | | 100% avicel PH 102 |
| HF-1 | 10.95 | Tween 80 | 30.51 | 100% avicel PH 102 |
| HF-2 | 10.95 | Tween 80 | 30.51 | 100% avicel PH 101 |

TABLE 21-continued a: Key formulation characteristics of extrudate of F-13 to F-20

| | | | | |
|---|---|---|---|---|
| HF-3 | 10.95 | PG | 30.51 | 100% avicel PH 102 |
| HF-4 | 10.95 | Kolliphor EL | 30.51 | 100% avicel PH 102 |
| HF-5 | 10.95 | PEG 200 | 30.51 | 100% avicel PH 102 |
| HF-6 | 26.98 | PEG 200 | 25.02 | 100% avicel PH 102 |
| HF-7 | 26.98 | Kolliphor EL | 25.02 | 50% avicel PH101 & 50% neusilin US2 |
| HF-8 | 38.12 | PEG 200 | 21.20 | 50% avicel PH101 & 50% neusilin US2 |

| Formulation | Carrier conc in extrudate (% w/w) | Coating conc in extrudate (% w/w) | Primojel conc in extrudate (% w/w) | HCTZ conc in extrudate (% w/w) |
|---|---|---|---|---|
| Physical mixture pellet | 36.83 | 1.84 | 3.97 | 4.41 |
| HF-1 | 45.81 | 2.29 | 4.94 | 5.49 |
| HF-2 | 45.81 | 2.29 | 4.94 | 5.49 |
| HF-3 | 45.81 | 2.29 | 4.94 | 5.49 |
| HF-4 | 45.81 | 2.29 | 4.94 | 5.49 |
| HF-5 | 45.81 | 2.29 | 4.94 | 5.49 |
| HF-6 | 37.57 | 1.88 | 4.05 | 4.50 |
| HF-7 | 37.57 | 1.88 | 4.05 | 4.50 |
| HF-8 | 31.84 | 1.59 | 3.43 | 3.81 | b: Key formulation characteristics of F-13 to F-20

| Formulation | Liquid vehicle | Liquid vehicle conc after drying (% w/w) | Carrier type | Carrier conc after drying (% w/w) |
|---|---|---|---|---|
| Physical mixture pellet | | | 100% avicel PH 102 | 78.27 |
| HF-1 | Tween 80 | 34.26 | 100% avicel PH 102 | 51.45 |
| HF-2 | Tween 80 | 34.26 | 100% avicel PH 101 | 51.45 |
| HF-3 | PG | 34.26 | 100% avicel PH 102 | 51.45 |
| HF-4 | Kolliphor EL | 34.26 | 100% avicel PH 102 | 51.45 |
| HF-5 | PEG 200 | 34.26 | 100% avicel PH 102 | 51.45 |
| HF-6 | PEG 200 | 34.26 | 100% avicel PH 102 | 51.45 |
| HF-7 | Kolliphor EL | 34.26 | 50% avicel PH101 & 50% neusilin US2 | 51.45 |
| HF-8 | PEG 200 | 34.26 | 50% avicel PH101 & 50% neusilin US2 | 51.45 |

| Formulation | Coating conc after drying (% w/w) | Primojel conc after drying (% w/w) | HCTZ conc after drying (% w/w) | Total weight of 12.5 mg HCTZ liqui-pellet (mg) |
|---|---|---|---|---|
| Physical mixture pellet | 3.91 | 8.44 | 9.37 | 133.34 |
| HF-1 | 2.57 | 5.55 | 6.16 | 202.84 |
| HF-2 | 2.57 | 5.55 | 6.16 | 202.84 |
| HF-3 | 2.57 | 5.55 | 6.16 | 202.84 |
| HF-4 | 2.57 | 5.55 | 6.16 | 202.84 |
| HF-5 | 2.57 | 5.55 | 6.16 | 202.84 |
| HF-6 | 2.57 | 5.55 | 6.16 | 202.84 |
| HF-7 | 2.57 | 5.55 | 6.16 | 202.84 |
| HF-8 | 2.57 | 5.55 | 6.16 | 202.84 |

In-Vitro Drug Dissolution Test

All formulation underwent dissolution test using USP dissolution apparatus II (708-DS Dissolution Apparatus & Cary 60 UV-Vis, Agilent Technologies, USA). The formulations were in a form of pellet filled in capsule. Each capsule contained physical mixture pellet or specified liqui-pellet formulation equivalent to 12.5 mg of HCTZ.

Dissolution test was set under constant condition of 900 ml of dissolution medium, temperature of 37.3±0.50C and paddle agitation of 50 rpm. HCl buffer solution with pH of 1.2 without enzymes was used as dissolution medium to mimic gastric fluid environment. The absorbance reading was taken at 272 nm at time interval of 5 min for an hour then time interval of 10 min for another hour.

Beers Lambert calibration curve obtained from preliminary work was used to calculate the concentration of HCTZ during dissolution test. Note that HCTZ dissolution rate is not significantly affected by the change in pH from the stomach (~1.2) to the small intestine (~7.4); hence, it was considered sufficient to only carry out the dissolution test under pH 1.2 at wavelength 272 nm.

The remaining methods were the same as described in Example 1.

Results and Discussion
Solubility Measurement

The results of the solubility tests are given in table 22, below.

TABLE 22

Solubility of HCTZ in a variety of liquid vehicles

| Non-volatile solvent | Mean concentration (mg/ml) ± SD | Inference |
|---|---|---|
| Tween 80 | 27.46 ± 1.31 | Sparingly soluble |
| PG | 11.35 ± 4.94 | Sparingly soluble |
| Kolliphor EL | 95.93 ± 5.81 | Soluble |
| PEG 200 | 155.92 ± 6.33 | Freely soluble |

The saturation solubility test shows that HCTZ is most soluble in PEG 200 compared to the other liquid vehicles. In fact, the solubility data suggests that HCTZ is freely soluble in PEG 200, making PEG the most suitable candidate for HCTZ liqui-pellet. After PEG 200, the next liquid vehicle which HCTZ is most soluble in is Kolliphor EL, then tween 80, and finally least soluble in PG.

Flowability Studies

The Physical Mixture and HF-1 to HF-8 Underwent Flowability Test, and the Results are shown in table 23.

TABLE 23

Flow rate (g/sec), Angle of repose and Carr's compressible index (CI %) of physical mixture pellet and HF-1 to HF-8

| Formulation | Flow Rate (g/sec) ± SD | Angle of repose ± SD | CI % ± SD | Inference according to Angle of repose | Inference according to CI % |
|---|---|---|---|---|---|
| Physical mixture pellet | 7.73 ± 0.21 | 24.38 ± 0.73 | 11.62 ± 0.00 | Excellent | Good |
| HF-1 | 6.93 ± 0.10 | 27.57 ± 1.00 | 8.83 ± 0.00 | Excellent | Excellent |
| HF-2 | 6.28 ± 0.61 | 28.19 ± 0.84 | 11.71 ± 1.56 | Excellent | Good |
| HF-3 | 6.33 ± 0.19 | 26.38 ± 0.77 | 15.16 ± 0.00 | Excellent | Good-fair |
| HF-4 | 6.31 ± 0.33 | 28.86 ± 0.60 | 11.12 ± 0.00 | Excellent | Good |
| HF-5 | 6.00 ± 0.18 | 27.96 ± 0.46 | 9.80 ± 1.70 | Excellent | Excellent |
| HF-6 | 7.93 ± 0.15 | 25.26 ± 0.14 | 8.84 ± 0.00 | Excellent | Excellent |
| HF-7 | 7.27 ± 0.09 | 24.42 ± 0.49 | 11.4 ± 0.00 | Excellent | Good |
| HF-8 | 7.63 ± 0.20 | 23.41 ± 0.43 | 11.77 ± 0.00 | Excellent | Good |

According to the angle of repose, all formulations have excellent flow properties. As for CI, the flow properties are slightly more disperse but all formulations have excellent, good or good-fair flow properties. In general, the flow properties of all of the formulation do not pose a major issue.

Particle Size Studies

As with the previous examples, all of the formulations were observed to have a relatively narrow size distribution with size below 2 mm.

In-Vitro Dissolution Test

Figure 18:
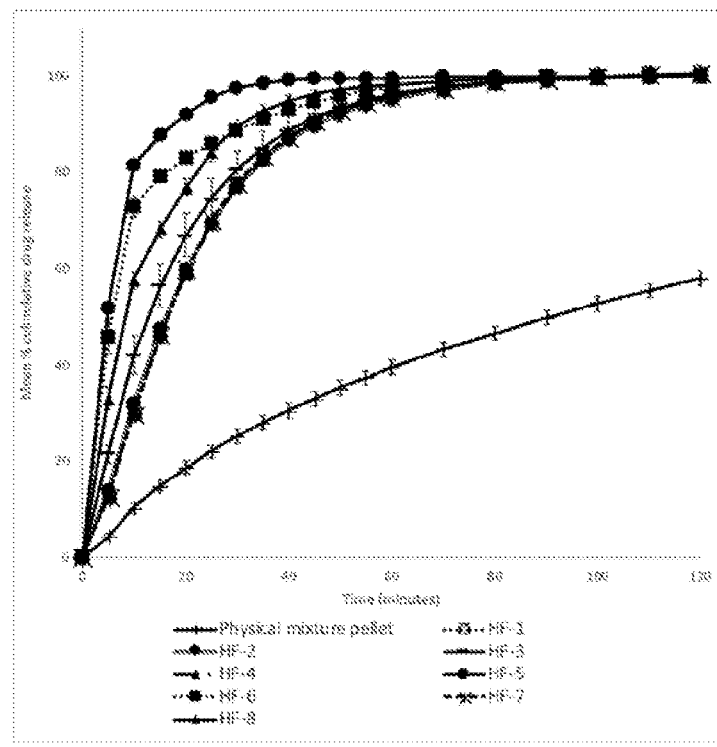
FIG. 18 is a graph showing the dissolution of formulations HF-1 to HF-8 and the physical mixture pellet formulation at pH 1.2

As shown in FIG. 18, formulation HF-5, which contained PEG 200 liquid vehicle, shows the fastest drug release rate, where 100% drug release is achieved in ~40 min. The two next fastest drug release formulations are HF-6 and HF-8. The composition of HF-6 is the same as HF-5 except a higher water content was used during the extrusion and spheronization process, which has resulted in a slightly slower dissolution rate.

Formulation HF-8 show a slower dissolution profile than HF-5. This is interesting because HF-8 comprises neusilin US2 and avicel PH102 as part of the carrier material. As explained in example 6, neusilin US2 significantly improves the dissolution rate of effervescent liqui-pellets where the API is naproxen and co-solvent is tween 80.

However, it should be noted that HF-8 contains 5 times the amount of water content than HF-5, which could be a reason for the slower dissolution rate.

In general, the three best performing formulations (HF-5, HF-6 and HF-8) all contain PEG 200 as the liquid vehicle. This corresponds with the solubility studies discussed above.

Formulation HF-1 and HF-2 all have very similar dissolution profiles. Avicel PH102 is the carrier for HF-1 and avicel PH101 is the carrier for HF-2, indicating that varying these two different grades of avicel does not have an effect on the dissolution rate.

Formulation HF-4 also has a very similar dissolution profile to HF-1 and HF-2. This is surprising as the co-solvent for HF-1 and HF-2 is tween 80 and the co-solvent for HF-5 is kolliphor EL, which showed remarkably different solubility for HCTZ.

Conclusion

The inventors have shown that the liqui-pellet dosage form can be used for APIs other than naproxen. Furthermore, of the liquid vehicles tested, PEG 200 was found to be the best liquid vehicle for use with HCTZ.

Example 8: Optimizing Hydrochlorothiazide Liqui-Pellet

The inventors wanted to investigate ways to further optimise the dissolution properties of the HCTZ liqui-pellets produced in example 7.

Materials and Methods

Materials

Hydrochlorothiazide was obtained from Spectrum Chemical MFG Corp (USA). Other excipients used to prepare the liqui-pellet included microcrystalline cellulose (avicel PH-101), (FMC corp, UK); colloidal silicon dioxide (aerosil 300), (Evonik Industries AG, Hanau, Germany); sodium starch glycolate Type A (primojel), (DFE Pharma, Goch, Germany), sodium bicarbonate, (Acros, New Jersey, USA); synthetic magnesium alumino-metasilicate (Neusilin US2), (Fuji Chemicals, Japan); polysorbate 80 (tween 80), (Acros, Netherlands); polyethylene glycol 200 (PEG 200), (Fisher Scientific, Leicester, UK) and macrogolglycerol ricinoleate 35 (Kolliphor EL), (BASF SE, Ludwigshafen, Germany). All other reagents and solvent were of analytical grades.

Preparation of HCTZ 12.5 mg Liqui-Pellet

The physical mixture pellet and all liqui-pellet formulations were made via extrusion-spheronization process. All formulations were prepared in a similar manner; however, there are variations in parameters such as: carrier composition; types of liquid vehicle; amount of liquid vehicle; amount of water content and the present of sodium bicarbonate, as shown in table 24 below.

The liquid medication was prepared by having a specified amount of HCTZ and specified liquid vehicle of specified amount mixed via a mortar and pestle method. The liquid medication was then incorporated into specified carrier material which could be 100% avicel PH102 or a mixture of 50% avicel PH102 and 50% neusilin US2.

All formulations had ~10% w/w primojel (superdisintegrant) and carrier to coating ratio of 20:1 respectively. The coating material used was aerosil 300. Apart from physical mixture pellet, all liqui-pellet formulation had either 34.26% w/w or 28.29% w/w of specified liquid vehicle and a liquid load factor (Lf) of 0.79 or 1.03. The liquid medication along with carrier and primojel were mixed for 2 min at a constant rate of 125 rpm (Caleva Multitab, Caleva Process Solutions Ltd, UK). The primojel was added intragranularly. Specified amount of granulating liquid (deionized water) was added bit by bit to achieve reasonable plastic property for extrusion (Caleva Multitab, Caleva Process Solutions Ltd, UK). The duration of mixing of the admixture with granulating liquid was 5 min. Aerosil 300 was then added into the admixture and further mixed for 5 min before extrusion. Once the sample was extruded, the extrudate was spheronized at an almost constant rotation at 4000 rpm (decrease to 2000 rpm if agglomeration seems likely). The spheronization time varied depending on the extrudate's plastic property to avoid agglomeration. The pellets were then placed in an oven under a constant temperature of 40° C. overnight to remove water content.

TABLE 24

| a: Key formulation characteristics of extrude of HLP-1 to HLP-6 | | | | | |
|---|---|---|---|---|---|
| Formulation | Water conc in extrudate (% w/w) | Liquid vehicle | Liquid vehicle conc in extrudate (% w/w) | Carrier type | Carrier conc in extrudate (% w/w) |
| Physical mixture pellet | 52.94 | | | Avicel PH 102 | 36.83 |
| HLP-1 | 26.98 | Tween 80 | 25.02 | 50% avicel PH 102 & 50% neusilin US2 | 37.57 |
| HLP-2 | 26.98 | Kolliphor EL | 25.02 | 50% avicel PH 102 & 50% neusilin US2 | 37.57 |
| HLP-3 | 38.12 | PEG 200 | 21.20 | 50% avicel PH 102 & 50% neusilin US2 | 31.84 |
| HLP-4 | 14.42 | Tween 80 | 24.21 | 50% avicel PH 102 & 50% neusilin US2 | 26.74 |
| HLP-5 | 14.42 | Kolliphor EL | 24.21 | 50% avicel PH 102 & 50% neusilin US2 | 26.74 |
| HLP-6 | 20.76 | PEG 200 | 22.42 | 50% avicel PH 102 & 50% neusilin US2 | 24.75 |

| Formulation | Coating conc in extrudate (% w/w) | Primojel conc in extrudate (% w/w) | NaHCO$_3$ conc in extrudate (% w/w) | HCTZ conc in extrudate (% w/w) |
|---|---|---|---|---|
| Physical mixture pellet | 1.84 | 3.97 | | 4.41 |
| HLP-1 | 1.88 | 4.05 | | 4.50 |
| HLP-2 | 1.88 | 4.05 | | 4.50 |
| HLP-3 | 1.59 | 3.43 | | 3.81 |

TABLE 24-continued

| | | | | |
|---|---|---|---|---|
| HLP-4 | 1.34 | 2.88 | 27.21 | 3.20 |
| HLP-5 | 1.34 | 2.88 | 27.21 | 3.20 |
| HLP-6 | 1.24 | 2.67 | 25.20 | 2.96 | b: Key formulation characteristics of HLP-1 to HLP-6

| Formulation | Liquid vehicle | Liquid vehicle conc after drying (% w/w) | Liquid load factor after drying | Carrier type | Carrier conc after drying (% w/w) |
|---|---|---|---|---|---|
| Physical mixture pellet | | 0 | | Avicel PH 102 | 78.27 |
| HLP-1 | Tween 80 | 34.26 | 0.8 | 50% avicel PH 102 & 50% neusilin US2 | 51.45 |
| HLP-2 | Kolliphor EL | 34.26 | 0.8 | 50% avicel PH 102 & 50% neusilin US2 | 51.45 |
| HLP-3 | PEG 200 | 34.26 | 0.8 | 50% avicel PH 102 & 50% neusilin US2 | 51.45 |
| HLP-4 | Tween 80 | 28.29 | 1 | 50% avicel PH 102 & 50% neusilin US2 | 31.24 |
| HLP-5 | Kolliphor EL | 28.29 | 1 | 50% avicel PH 102 & 50% neusilin US2 | 31.24 |
| HLP-6 | PEG 200 | 28.29 | 1 | 50% avicel PH 102 & 50% neusilin US2 | 31.24 |

| Formulation | Coating conc after drying (% w/w) | Primojel conc after drying (% w/w) | NaHCO$_3$ conc after drying (% w/w) | HCTZ conc after drying (% w/w) | Total weight of 12.5 mg HCTZ liqui-pellet (mg) |
|---|---|---|---|---|---|
| Physical mixture pellet | 3.91 | 8.44 | | 9.37 | 133.34 |
| HLP-1 | 2.57 | 5.55 | | 6.16 | 202.84 |
| HLP-2 | 2.57 | 5.55 | | 6.16 | 202.84 |
| HLP-3 | 2.57 | 5.55 | | 6.16 | 202.84 |
| HLP-4 | 1.56 | 3.37 | 31.8 | 3.74 | 334.09 |
| HLP-5 | 1.56 | 3.37 | 31.8 | 3.74 | 334.09 |
| HLP-6 | 1.56 | 3.37 | 31.8 | 3.74 | 334.09 |

The remaining methods were the same as described in Example 1.

Results and Discussion

Flow Properties of HMT Formulations

The physical mixture and HLP-1 to HLP-6 underwent flowability test, and the results are shown in table 25.

TABLE 25

Flow rate (g/sec), Angle of repose and Carr's compressible index (CI %) of physical mixture pellet and HLP-1 to HLP-6

| Formulation | Flow Rate (g/sec) ± SD | Angle of repose ± SD | CI % ± SD | Inference according to Angle of repose | Inference according to CI % |
|---|---|---|---|---|---|
| Physical mixture pellet | 7.73 ± 0.21 | 24.38 ± 0.73 | 11.62 ± 0.00 | Excellent | Good |
| HLP-1 | 6.78 ± 0.25 | 24.95 ± 0.73 | 12.29 ± 1.52 | Excellent | Good |
| HLP-2 | 6.28 ± 0.61 | 28.19 ± 0.84 | 11.71 ± 1.56 | Excellent | Good |
| HLP-3 | 6.33 ± 0.19 | 26.38 ± 0.77 | 15.16 ± 0.00 | Excellent | Good-fair |
| HLP-4 | 8.18 ± 0.08 | 26.18 ± 0.90 | 8.33 ± 0.00 | Excellent | Excellent |
| HLP-5 | 8.24 ± 0.06 | 26.16 ± 0.34 | 12.82 ± 0.00 | Excellent | Good |
| HLP-6 | 9.59 ± 0.04 | 24.03 ± 0.35 | 11.12 ± 0.00 | Excellent | Good |

The angle of repose of all of the formulations indicates excellent flow properties. There are slight variations in the class of flow properties between the angle of repose and CI methods, nonetheless, both results indicate acceptable flowability, which is ideal for manufacturing.

Particle Size Studies

All of the formulations were found to have a very narrow distribution within 500 m, which is considered relatively small in comparison to other examples. This may be due to the present of neusilin US2.

In-Vitro Dissolution Test

Figure 19:
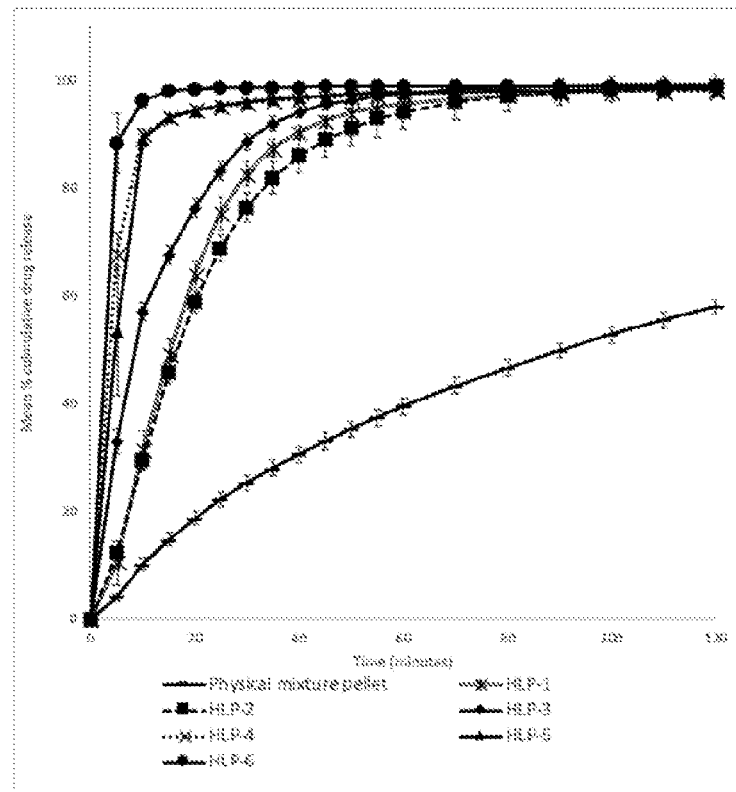
FIG. 19 is a graph showing the dissolution of formulations HLP-1 to HLP-6 and the physical mixture pellet formulation at pH 1.2.

As shown in FIG. 19, formulation HLP-6 has a remarkably fast dissolution rate, where 100% HCTZ release is achieved within 15 min. This is considered extremely fast in comparison to other technologies, which also aims to achieve a fast dissolution rate.

An effervescent agent is not present in HLP-1 (tween 80), HLP-2 (kolliphor EL) and HLP-3 (PEG 200). The composition is the same for these three formulations except for type of liquid vehicle and amount of water used. Note that the amount of water only varied among these formulations to make sure the extrudate have suitable rheological properties for successful liqui-pellet production. Among these three formulations, HLP-3 displayed the fastest dissolution rate, which accord with example 7 where HCTZ was shown to be most soluble in PEG 200 compared to tween 80 and Kolliphor EL.

Meanwhile, HLP-4, HLP-5 and HLP-6 all contain effervescent agent but have a lower concentration of co-solvent than formulation HLP-1, HLP-2 and HLP-3. It is found that although HLP-4, HLP-5 and HLP-6 have lower concentration of co-solvent than the other formulations, their dissolution profile shows markedly faster dissolution rate.

This is due to the presence of the effervescent agent promoting disintegration and disrupting the stagnant layer.

Among these effervescent liqui-pellet formulations, it is not surprising that HLP-6 have the fastest dissolution rate (100% drug release in 15 min) as PEG 200 was the co-solvent and it contained an effervescent agent.

Conclusion

The inventors have shown that HCTZ liqui-pellet is able to achieve remarkably rapid enhanced drug release when the formulation is optimized. In particular, when both the choice of co-solvent and the provision of an effervescent agent were optimised a formulation achieved 100% drug release within 15 min.

Example A: Producing a Naproxen Liqui-Tablet

The inventors decided to investigate if the liqui-pellet formulation could be compressed into tablets (liqui-tablet).

Materials and Methods

Materials

The materials were as described in example 5.

Preparation of Naproxen Liqui-Tablet

The preparation of liqui-pellet was in the same manner as in example 6 but with the addition of a compaction step of different force as shown in Table 26.

Table 26a: Key formulation characteristics of extrudate of NLT-1 to NLT-8

| Formulation | Water conc in extrudate (% w/w) | Liquid vehicle conc in extrudate (% w/w) | Liquid load factor | Carrier type | Carrier conc in extrudate (% w/w) |
|---|---|---|---|---|---|
| Physical mixture 1 | 25.93 | | | 100% avicel PH101 | 31.80 |
| Physical mixture 2 | 25.93 | | | 100% avicel PH101 | 31.80 |
| NLT-1 | 21.88 | 14.84 | 1.00 | 100% avicel PH101 | 24.78 |
| NLT-2 | 13.49 | 19.90 | 1.23 | 100% avicel PH101 | 24.15 |
| NLT-3 | 13.79 | 16.38 | 1.00 | 50% avicel PH101 & 50% neusilin US2 | 27.34 |
| NLT-4 | 13.79 | 19.83 | 1.23 | 50% avicel PH101 & 50% neusilin US2 | 24.07 |
| NLT-5 | 13.79 | 19.83 | 1.23 | 50% avicel PH101 & 50% neusilin US2 | 24.07 |
| NLT-6 | 13.79 | 19.83 | 1.23 | 50% avicel PH101 & 50% neusilin US2 | 24.07 |
| NLT-7 | 21.88 | 14.84 | 1.00 | 100% avicel PH101 | 24.78 |
| NLT-8 | 13.49 | 19.90 | 1.23 | 100% avicel PH101 | 24.15 |

| Formulation | Coating conc in extrudate (% w/w) | Primojel conc in extrudate (% w/w) | Sodium bicarbonate conc in extrudate (% w/w) | Naproxen conc in extrudate (% w/w) |
|---|---|---|---|---|
| Physical mixture 1 | 1.59 | 3.24 | 23.70 | 13.69 |
| Physical mixture 2 | 1.59 | 3.24 | 23.70 | 13.69 |
| NLT-1 | 1.25 | 2.35 | 25.00 | 9.90 |
| NLT-2 | 1.21 | 3.37 | 27.68 | 10.97 |

| | | | | |
|---|---|---|---|---|
| NLT-3 | 1.38 | 2.59 | 27.59 | 10.93 |
| NLT-4 | 1.20 | 2.59 | 27.59 | 10.93 |
| NLT-5 | 1.20 | 2.59 | 27.59 | 10.93 |
| NLT-6 | 1.20 | 2.59 | 27.59 | 10.93 |
| NLT-7 | 1.25 | 2.35 | 25.00 | 9.90 |
| NLT-8 | 1.21 | 3.37 | 27.68 | 10.97 |

Table 26b: Key formulation characteristics of NLT-1 to NLT-8 after drying and compression force used

| Formulation | Liquid vehicle conc after drying (% w/w) | Liquid load factor | Carrier type | Carrier conc after drying (% w/w) | Coating conc after drying (% w/w) |
|---|---|---|---|---|---|
| Physical mixture 1 | | | 100% avicel PH101 | 42.93 | 2.14 |
| Physical mixture 2 | | | 100% avicel PH101 | 42.93 | 2.14 |
| NLT-1 | 19 | 1.00 | 100% avicel PH101 | 31.71 | 1.60 |
| NLT-2 | 23 | 1.23 | 100% avicel PH101 | 27.92 | 1.39 |
| NLT-3 | 19 | 1.00 | 50% avicel PH101 & 50% neusilin US2 | 31.71 | 1.60 |
| NLT-4 | 23 | 1.23 | 50% avicel PH101 & 50% neusilin US2 | 27.92 | 1.39 |
| NLT-5 | 23 | 1.23 | 50% avicel PH101 & 50% neusilin US2 | 27.92 | 1.39 |
| NLT-6 | 23 | 1.23 | 50% avicel PH101 & 50% neusilin US2 | 27.92 | 1.39 |
| NLT-7 | 19 | 1.00 | 100% avicel PH101 | 31.71 | 1.60 |
| NLT-8 | 23 | 1.23 | 100% avicel PH101 | 27.92 | 1.39 |

| Formulation | Primojel conc after drying (% w/w) | Sodium bicarbonate conc after drying (% w/w) | Naproxen conc after drying (% w/w) | Compression force (PSI) | Total weight of 25 mg naproxen liqui-pellet (mg) |
|---|---|---|---|---|---|
| Physical mixture 1 | 4.37 | 32.00 | 18.48 | 400 | 135.25 |
| Physical mixture 2 | 4.37 | 32.00 | 18.48 | 800 | 135.25 |
| NLT-1 | 3.00 | 32.00 | 12.68 | 400 | 197.2 |
| NLT-2 | 2.88 | 32.00 | 12.68 | 400 | 197.2 |
| NLT-3 | 3.00 | 32.00 | 12.68 | 400 | 197.2 |
| NLT-4 | 3.00 | 32.00 | 12.68 | 400 | 197.2 |
| NLT-5 | 3.00 | 32.00 | 12.68 | 600 | 197.2 |
| NLT-6 | 3.00 | 32.00 | 12.68 | 800 | 197.2 |
| NLT-7 | 3.00 | 32.00 | 12.68 | 800 | 197.2 |
| NLT-8 | 2.88 | 32.00 | 12.68 | 800 | 197.2 |

Friability Test

All formulations were subjected to friability test, where 10 liqui-tablets of each formulation were placed in a friabilator chamber (D-63150, Erweka, Germany) and set under constant rotation of 25 rpm for 4 min. The percentage weight loss of sample was calculated using the weight of sample before and after the friability test Tablet hardness test Tablet hardness test was carried using the tablet hardness tester (TBH 125, Erweka, Germany). For each formulation, 5 tablets were tested with tablet mean thickness, mean diameter and mean hardness recorded.

Accelerated Stability Test

A stability test was conducted on formulation NLT-5 which is considered one of the best optimized formulations in this investigation. The storage temperature of the accelerated stability test was kept at 40° C. with relative humidity of 75% for a period of 3 months. Observations of physical changes were recorded and in-vitro drug release studies where carried out each month for 3 months.

The remaining methods were the same as described in Example 1.

Results and Discussion

Friability Studies

The compaction of liqui-pellets into a liqui-tablet was successful for all of the formulations. However, not all formulations passed the friability test, as shown in table 27 which suggests that some formulations are not robust enough.

TABLE 27

Results of friability tests for physical
mixtures 1 and 2 and NLT-1 to NLT-8

| Formulation | % weight loss | Fractured (Yes/No) | Pass/Fail |
|---|---|---|---|
| Physical mixture 1 | n/a | Yes | Fail |
| Physical mixture 2 | 0.15 | No | Pass |
| NLT-1 | n/a | Yes | Fail |
| NLT-2 | n/a | Yes | Fail |
| NLT-3 | 0 | No | Pass |
| NLT-4 | 0 | No | Pass |
| NLT-5 | 0 | No | Pass |
| NLT-6 | 0 | No | Pass |
| NLT-7 | n/a | Yes | Fail |
| NLT-8 | n/a | Yes | Fail |

Physical mixture 1 and formulation NLT-1, NLT-2, NLT-7 and NLT-8 all failed the friability test due to fracturing. It is noted that none of those failed formulations contained neusilin US2. Conversely, with the exception of physical mixture 2, all of the formulations that did passed the friability test contained neusilin US2.

Meanwhile, both physical mixture 1 and 2 have the same composition, the only difference is that different compression forces were applied. Physical mixture 1, which underwent lower compression force, failed the friability test, whereas physical mixture 2, which was compressed at a higher force, passed the test. This suggests that compaction force influences the physical properties of liqui-tablet and a higher compaction force provides a more robust liqui-tablet.

Tablet Hardness Test

The tablet hardness test results are shown in table 28.

TABLE 28

Results of tablet harness test for physical
mixture 1 and 2, NLT-1 and NLT-3 to NLT-7

| Formulation | Mean thickness ± SD (mm) | Mean diameter ± SD (mm) | Mean hardness ± SD (N) |
|---|---|---|---|
| Physical mixture 1 | 5.98 ± 0.05 | 5.23 ± 0.02 | 56.80 ± 10.94 |
| Physical mixture 2 | 5.60 ± 0.01 | 5.25 ± 0.01 | 102.60 ± 13.03 |
| NLT-1 | 7.92 ± 0.05 | 5.25 ± 0.01 | 85.20 ± 8.11 |
| NLT-3 | 7.55 ± 0.02 | 5.26 ± 0.01 | 90.40 ± 2.70 |
| NLT-4 | 7.66 ± 0.02 | 5.26 ± 0.00 | 54.60 ± 3.13 |
| NLT-5 | 7.61 ± 0.03 | 5.25 ± 0.00 | 60.60 ± 5.27 |
| NLT-6 | 7.60 ± 0.02 | 5.27 ± 0.01 | 52.40 ± 2.51 |
| NLT-7 | 7.87 ± 0.02 | 5.26 ± 0.01 | 73.60 ± 5.59 |

The results show that compression force has a major influence on the hardness of physical mixture tablet, but hardly any influence on liqui-tablet formulation. For instance, physical mixture 2 has about double the hardness of physical mixture 1, and was subjected to twice the compression force that physical mixture 1 was subjected to. Conversely, NLT-1 and NLT-7 have the same composition, but NLT-7 was compressed with twice as much force than NLT-1. Despite this difference, the hardness for NLT-1 and NLT-7 is similar. Similarly, the compositions of NLT-4, NLT-5 and NLT-6 is the same but different compression forces were used, and again the tablet hardness is similar for all three compositions.

It is noted that the liquid vehicle concentration has a major influence on liqui-tablet hardness. When liquid vehicle concentration is increased the hardness of liqui-tablet is reduced. For instance, this is shown in formulation NLT-3 and NLT-4 where the amount of liquid vehicle differs between the two formulations. Formulation NLT-4 has a higher concentration of tween 80 than NLT-3, and significantly lower tablet hardness.

Furthermore, formulations comprising neusilin US2 are observed to have increased liqui-tablet hardness. This is shown in NLT-2 and NLT-4 where both have the same high concentration of tween 80 (23% w/w) and compressed at the same force (400 PSI). However, NLT-2 did not contain neusilin US2 and was too soft to be subjected to the tablet hardness test. Similarly, NLT-8 and NLT-6 composition and production both are identical, except NLT-8 was absent of neusilin US2, which made it too soft to be subjected to the tablet hardness test.

In-Vitro Dissolution Test

Figure 20:
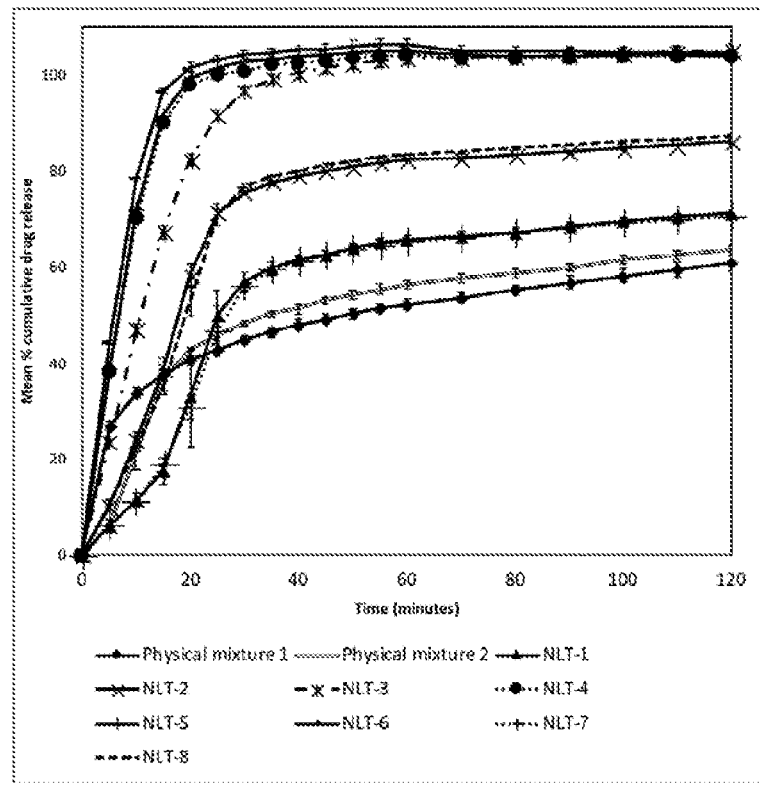
FIG. 20 is a graph showing the dissolution of formulations NLT-1 to NLT-8, physical mixture 1 and physical mixture pellet 2 at pH 1.2.

The dissolution test results of all formulations at acidic condition (pH1.2), and are shown in FIG. 20. When comparing liqui-pellet formulation with identical composition but under different compression force, there is no observable effect on dissolution rate.

As observed in the previous examples, the results show a general trend that increasing liquid vehicle concentration increases the dissolution rate and incorporation of neusilin US2 into the composition also increase the dissolution rate.

Also, the dissolution test results showed that liqui-tablet is capable of rapid enhanced drug release as shown in FIG. 20.

Accelerated Stability Test

Figure 21:
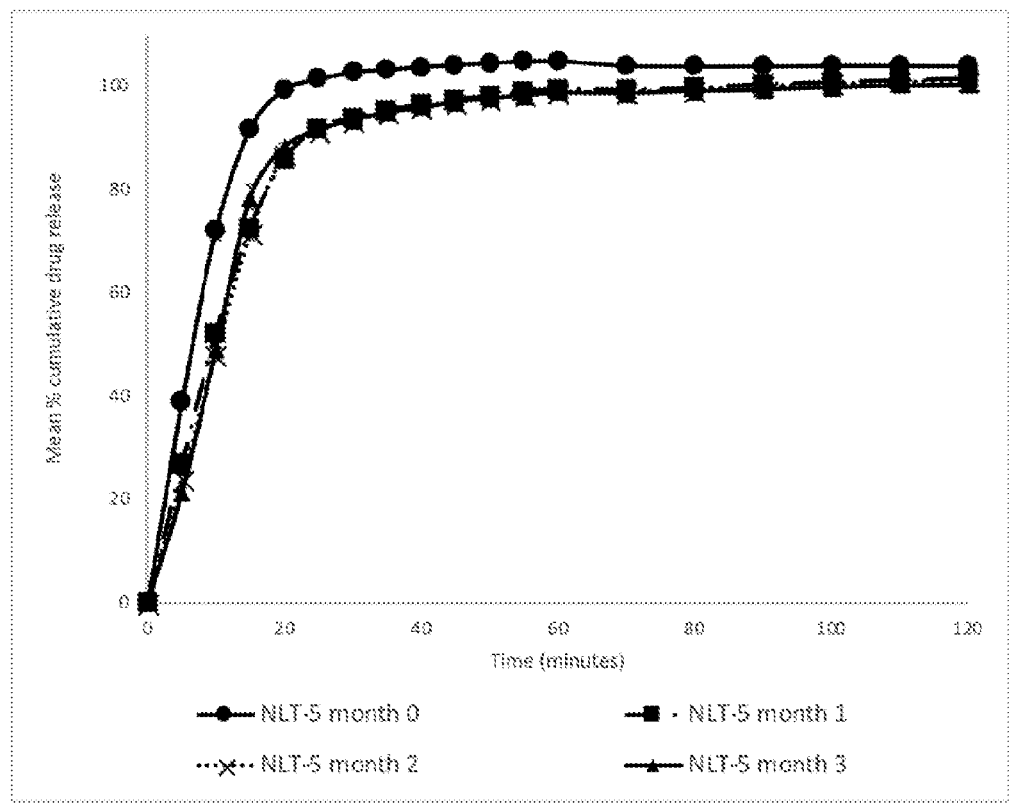
FIG. 21 is a graph showing the dissolution profile of formulation NLT-5 under accelerated stability test condition (40° C. and 75% relative humidity) over the period of 3 months at pH 1.2.

Results from stability tests of formulation NLT-5 kept for various periods of time at 40° C. and under 75% relative humidity are shown in FIG. 21. The sample shows only ~4% in reduction of drug release even for the sample which was maintained under the harsh conditions for 3 months.

Conclusion

The inventors have shown it is possible to compress the liqui-pellet formulation to produce tablets, which are termed liqui-tablet. Advantageously, the step of compressing the pellets does not affect the drug release properties of the composition.

Furthermore, the presence of neusilin US2 in the formulation improves the liqui-tablet hardness and dissolution rate.

Example 10: Producing a High Dose Liqui-Tablet

The inventors decided to investigate if a high dose liqui-tablet could be produced. They used ketoprofen 100 mg as the drug model.

Materials and Methods

Materials

Ketoprofen was obtained from Tokyo Chemical Industry Co (Japan). Other excipients used to prepare the liqui-tablet included microcrystalline cellulose (avicel PH-102), (FMC corp., UK); colloidal silicon dioxide (aerosil 300), (Evonik Industries AG, Hanau, Germany); sodium starch glycolate Type A (primojel); polyethylene glycol 200 (Fisher Scientific, Leicester, UK); propylene glycol (SAFC, Spain); polysorbate 80 (Tween 80), (Acros, Netherlands); sorbitan laurate (Span 80), (Gattefosse, Saint Priest, France) and macrogolglycerol ricinoleate 35 (Kolliphor EL), (BASF SE, Ludwigshafen, Germany). All other reagents and solvent were of analytical grades.

Saturation Solubility Studies

This was carried out in the same manner as example 1 except the samples were left in the bath shaker for 24 h and the liquid vehicles used were span 80, PEG 200, PG, Kolliphor EL and tween 85.

Preparation of Ketoprofen Liqui-Tablet

The liqui-tablet formulations were prepared via compacting liqui-pellet formulation under compression force of 800 PSI using a manual tablet press machine (Compaction model MTCM-I, Lobe pharma, UK). All liqui-pellet formulations were produced in a similar manner except for the variation in parameters such as: type of liquid vehicle and water content, as shown in Table 29. The liquid medication was prepared by mixing ketoprofen and specified liquid vehicle using pestle and mortar. This mixture was then incorporated into a specified carrier material alongside a specified amount of primojel (primojel added intragranularly). The admixture was mixed for 2 min at a constant rate of 125 rpm (Caleva Multitab, Caleva Process Solutions Ltd, UK). Specified amount of deionized water was added bit by bit to achieve reasonable plastic property for extrusion (Caleva Multitab, Caleva Process Solutions Ltd, UK). The admixture with water was mixed for 5 min, then Aerosil 300 (coating material) was added and further mixed for another 5 min before extrusion. Once the sample was extruded, the extrudate was spheronized at an almost constant rotation at 4000 rpm (decrease to 2000 rpm if agglomeration seems likely). The spheronization time varied depending on the extrudate's plastic property to avoid agglomeration. The pellets were then placed in an oven under a constant temperature of 40° C. overnight to remove water content.

Also note that physical mixture pellet was prepared in a similar manner as above, but without liquid vehicle incorporated. All formulation's carrier to coating material ratio were kept constant at 20:1 respectively.

TABLE 29

Key formulation characteristics of extrudate of KLT-1 to KLT-5

| Formulation | Water conc in extrudate (% w/w) | Liquid vehicle | Liquid vehicle conc in extrudate (% w/w) | Carrier conc in extrudate (% w/w) |
|---|---|---|---|---|
| Physical mixture | 49.74 | | 0.00 | 31.97 |
| KLT-1 | 13.42 | Span 80 | 22.37 | 40.27 |
| KLT-2 | 13.42 | PEG 200 | 22.37 | 40.27 |
| KLT-3 | 13.42 | PG | 22.37 | 40.27 |
| KLT-4 | 13.42 | Kolliphor EL | 22.37 | 40.27 |
| KLT-5 | 13.42 | Tween 85 | 22.37 | 40.27 |

| Formulation | Coating conc in extrudate (% w/w) | Primojel conc in extrudate (% w/w) | Ketoprofen conc in extrudate (% w/w) |
|---|---|---|---|
| Physical mixture | 1.60 | 2.51 | 14.21 |
| KLT-1 | 2.01 | 4.33 | 17.90 |
| KLT-2 | 2.01 | 4.33 | 17.90 |
| KLT-3 | 2.01 | 4.33 | 17.90 |
| KLT-4 | 2.01 | 4.33 | 17.90 |
| KLT-5 | 2.01 | 4.33 | 17.90 |

TABLE 29-continued

Key formulation characteristics of KLT-1 to KLT-5

| Formulation | Liquid vehicle | Liquid vehicle conc after drying (% w/w) | Carrier conc after drying (% w/w) | Coating conc after drying (% w/w) |
|---|---|---|---|---|
| Physical mixture | | | 63.60 | 3.18 |
| KLT-1 | Span 80 | 25.84 | 46.51 | 2.33 |
| KLT-2 | PEG 200 | 25.84 | 46.51 | 2.33 |
| KLT-3 | PG | 25.84 | 46.51 | 2.33 |
| KLT-4 | Kolliphor EL | 25.84 | 46.51 | 2.33 |
| KLT-5 | Tween 85 | 25.84 | 46.51 | 2.33 |

| Formulation | Primojel conc after drying (% w/w) | Ketoprofen conc after drying (% w/w) | Total weight of 100 mg ketoprofen liqui-pellet (mg) |
|---|---|---|---|
| Physical mixture | 4.95 | 28.27 | 353.75 |
| KLT-1 | 4.65 | 20.67 | 483.75 |
| KLT-2 | 4.65 | 20.67 | 483.75 |
| KLT-3 | 4.65 | 20.67 | 483.75 |
| KLT-4 | 4.65 | 20.67 | 483.75 |
| KLT-5 | 4.65 | 20.67 | 483.75 |

The remaining methods were the same as described in Examples 1 and 9.

Results and Discussion

Saturation Solubility Studies

Ketoprofen solubility in various liquid vehicles is shown in table 30. Among all of the liquid vehicle/co-solvent, the results indicate that ketoprofen is most soluble in PEG 200.

TABLE 30

Solubility of ketoprofen in various liquid vehicles

| Non-volatile solvent | Mean concentration (mg/ml) ± SD$^a$ | Inference |
|---|---|---|
| Span 80 | 19.83 ± 2.85 | Sparingly soluble |
| PEG 200 | 492.53 ± 2.26 | Freely soluble |
| PG | 257.64 ± 7.13 | Freely soluble |
| Kolliphor EL | 168.67 ± 0.39 | Freely soluble |
| Tween 85 | 294.59 ± 6.54 | Freely soluble |

Pre-Compression Flowability Test

Similar to previous examples, flow property of liqui-pellet is not an issue. All formulation achieved excellent, excellent-good or good flow properties.

Particle Size Analysis

All formulation achieved narrow size distribution.

Friability Studies

Friability test results are shown in table 31. All liqui-tablet formulation passed the friability test; however, the physical mixture tablet was the only one which failed the test. This suggests that liquid vehicle may contribute to improve liqui-tablet robustness against friability

TABLE 31

Friability test result of physical mixture
pellet and formulation KLT 1 to KLT 5

| Formulation | % weight loss | Fractured (Yes/No) | Passed/Failed |
|---|---|---|---|
| Physical mixture | | Yes | Failed |
| KLT-1 | 0.01 | No | Passed |
| KLT-2 | 0.01 | No | Passed |
| KLT-3 | 0.02 | No | Passed |
| KLT-4 | 0.02 | No | Passed |
| KLT-5 | 0.01 | No | Passed |

Tablet Hardness Test

The result from tablet harness test is shown in table 32. The results indicate that different types of liquid vehicles influence the liqui-tablet hardness. Liquid vehicle PG in formulation KLT-3 produces the hardness tablet.

TABLE 32

Results of tablet harness test for
physical mixture and KLT-1 to KLT-5

| Formulation | Mean thickness (mm) | Mean diameter (mm) | Mean hardness (N) |
|---|---|---|---|
| KLT-1 | 6.85 ± 0.04 | 10.09 ± 0.02 | 25.20 ± 1.92 |
| KLT-2 | 6.74 ± 0.03 | 10.08 ± 0.04 | 19.20 ± 0.45 |
| KLT-3 | 6.31 ± 0.01 | 10.2 ± 0.00 | 172.60 ± 10.53 |
| KLT-4 | 6.72 ± 0.02 | 10.06 ± 0.01 | 40.00 ± 1.58 |
| KLT-5 | 6.80 ± 0.01 | 10.09 ± 0.01 | 34.80 ± 2.59 |

In-Vitro Dissolution Test

Figure 22:
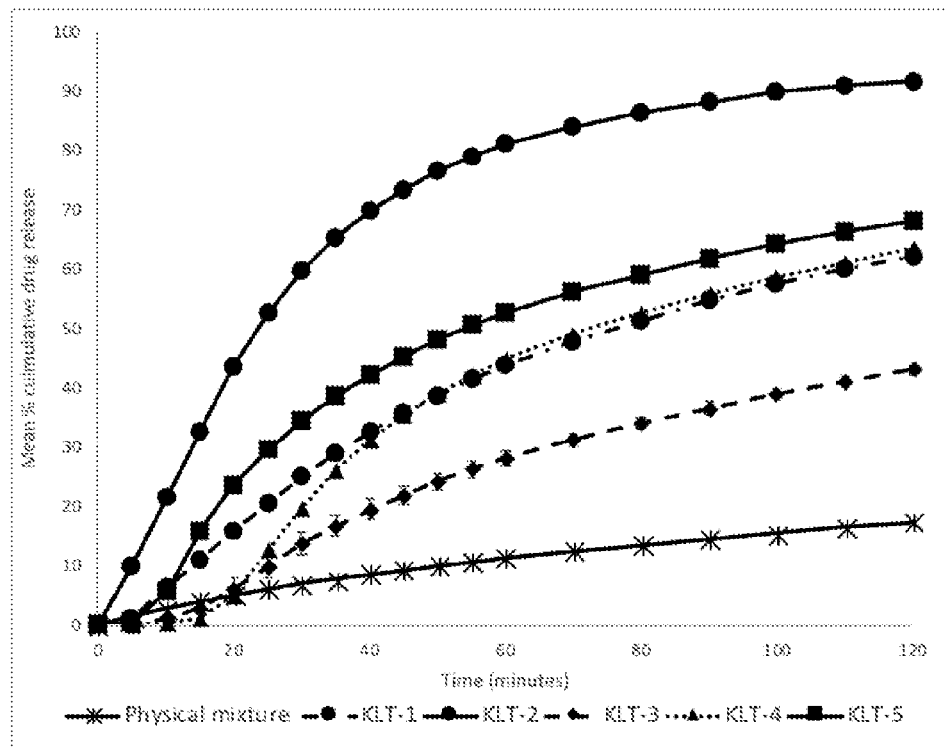
FIG. 22 is a graph showing the dissolution of formulations KLT-1 to KLT-5 and the physical mixture pellet at pH 1.2.
Figure 23:
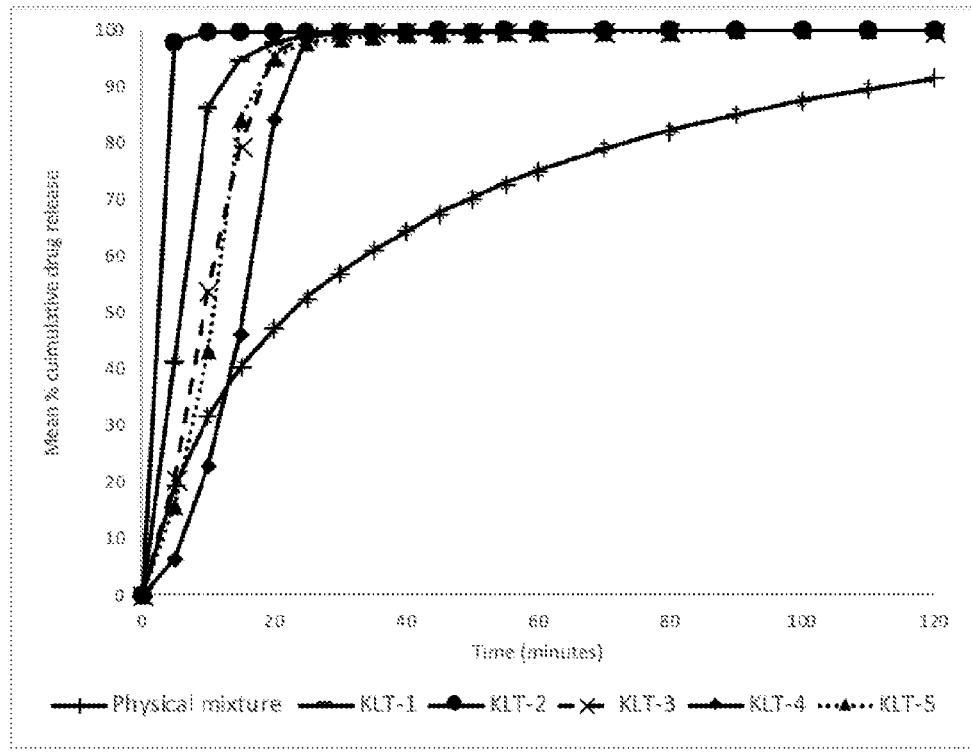
FIG. 23 is a graph showing the dissolution of formulations KLT-1 to KLT-5 and the physical mixture pellet at pH 7.4.

The dissolution test results at pH1.2 are shown in FIG. 22, and at pH7.4 are shown in FIG. 23. In these un-optimised liqui-tablet formulations, KLT-2, which contain PEG 200 liquid vehicle, shows the fastest drug release rate in both acidic and alkaline pH. This corresponds with the solubility studies.

Despite KLT-2 not being optimised, it's dissolution profile already looks promising (91% drug release after 2 h under acidic condition), particularly because ketoprofen is a weakly acidic drug, which means it is not soluble in an acidic environment. Under alkaline environment, KLT-2 achieve rapid drug release of 100% after 5 min.

Conclusion

The inventors have shown it is possible to produce high dose liqui-tablet whilst maintaining good pre-compression flowability and acceptable size and mass for swallowing.

It was also observed that different liquid vehicle influences the liqui-tablet hardness.

Example 11: Reduction of Ketoprofen Liqui-Tablet Via Formulation Weight Reduction Model The inventors investigated a possible approach to further reduce liqui-tablet weight.

Materials and Methods

Materials

The materials used were the same as described in example 10.

Preparation of Ketoprofen Liqui-Tablet

The preparation of ketoprofen liqui-tablet was carried out in the same manner as in example 10. However, there are variations in the formulation of the composition, as shown in Table 33.

One of four weight reduction models were used, these were:

1) Reduction of carrier and coating material to acceptable minimal limit;
2) Increasing the amount of the API in the liqui-mass system;
3) Reduction of carrier and coating material to acceptable minimal limit and increasing the amount of the API in the liqui-mass system; or
4) Reduction of carrier and coating material to acceptable minimal limit, increasing the amount of the API in the liqui-mass system and increasing the amount of the liquid vehicle to improve the dissolution rate.

TABLE 33

Key formulation characteristics of KF-1 to KF-10 and compression force used

| Formulation | Water conc in extrudate (% w/w) | Liquid vehicle conc in extrudate (% w/w) | Liquid load factor | Carrier conc in extrudate (% w/w) |
|---|---|---|---|---|
| Physical mixture | 49.74 | | | 31.97 |
| KF-1 | 13.42 | 22.37 | 1.00 | 40.27 |
| KF-2 | 14.13 | 23.53 | 1.13 | 37.64 |
| KF-3 | 5.88 | 29.32 | 1.50 | 35.19 |
| KF-4 | 6.28 | 31.34 | 1.80 | 31.35 |
| KF-5 | 6.72 | 33.68 | 2.25 | 29.08 |
| KF-6 | 18.93 | 18.92 | 1.22 | 34.06 |
| KF-7 | 5.53 | 27.93 | 2.20 | 27.60 |
| KF-8 | 5.26 | 31.45 | 2.40 | 28.13 |
| KF-9 | 5.12 | 30.36 | 2.40 | 28.68 |
| KF-10 | 8.97 | 26.96 | 1.71 | 31.45 |

| Formulation | Coating conc in extrudate (% w/w) | Primojel conc in extrudate (% w/w) | Ketoprofen conc in extrudate (% w/w) | Successfully spheronized into pellet? (Yes/No) |
|---|---|---|---|---|
| Physical mixture | 1.60 | 2.49 | 14.21 | Yes |
| KF-1 | 2.01 | 4.03 | 17.90 | Yes |
| KF-2 | 1.88 | 4.00 | 18.82 | Yes |
| KF-3 | 1.76 | 4.39 | 23.46 | Yes |
| KF-4 | 1.57 | 4.39 | 25.08 | Yes |
| KF-5 | 1.45 | 0.00 | 29.08 | No |
| KF-6 | 1.70 | 3.67 | 22.71 | Yes |
| KF-7 | 1.38 | 4.32 | 33.25 | Yes |
| KF-8 | 1.41 | 0.00 | 33.75 | No |
| KF-9 | 1.43 | 0.00 | 34.40 | No |
| KF-10 | 1.57 | 4.09 | 26.96 | Yes |

Key formulation characteristics of successfully spheronised formulations after drying and compression force used

| Formulation | Liquid vehicle conc after drying (% w/w) | Liquid load factor | Carrier conc after drying (% w/w) | Coating conc after drying (% w/w) |
|---|---|---|---|---|
| Physical mixture | | | 31.97 | 1.60 |
| KF-1 | 22.37 | 1.00 | 40.27 | 2.01 |
| KF-2 | 23.53 | 1.13 | 37.64 | 1.88 |
| KF-3 | 29.32 | 1.50 | 35.19 | 1.76 |
| KF-4 | 31.34 | 1.80 | 31.35 | 1.57 |
| KF-6 | 18.92 | 1.22 | 34.06 | 1.70 |
| KF-7 | 27.93 | 2.20 | 27.60 | 1.38 |
| KF-10 | 26.96 | 1.71 | 31.45 | 1.57 |

TABLE 33-continued

| Formulation | Primojel conc after drying (% w/w) | Ketoprofen conc after drying (% w/w) | Compression force (PSI) | Total weight of 100 mg ketoprofen liqui-pellet (mg) |
|---|---|---|---|---|
| Physical mixture | 2.49 | 14.21 | 800 | 353.75 |
| KF-1 | 4.03 | 17.90 | 1400 | 483.75 |
| KF-2 | 4.00 | 18.82 | 1400 | 456.25 |
| KF-3 | 4.39 | 23.46 | 1400 | 401.25 |
| KF-4 | 4.39 | 25.08 | 500 | 373.75 |
| KF-6 | 3.67 | 22.71 | 800 | 357 |
| KF-7 | 4.32 | 33.25 | 500 | 283.83 |
| KF-10 | 4.09 | 26.96 | 500 | 337.67 |

The remaining methods were the same as described in Example 1.

Results and Discussion

It has been observed in table 33 that it is possible to further reduce ketoprofen liqui-table weight. However, this reduction in weight is accompanied by a reduction of the dissolution rate.

Model 1

The key differences between KF-1 to KF-5 is a gradual decrease of the carrier and coating material, with KF-1 having the most carrier and coating material and KF-5 having the least. It is noted that the formulation with the least carrier and coating material, KF-5, did not successfully spheronize into a pellet due to agglomeration. This indicates that weight reduction model 1 has a limit and beyond that limit the formulation will fail to pelletise.

Figure 24:
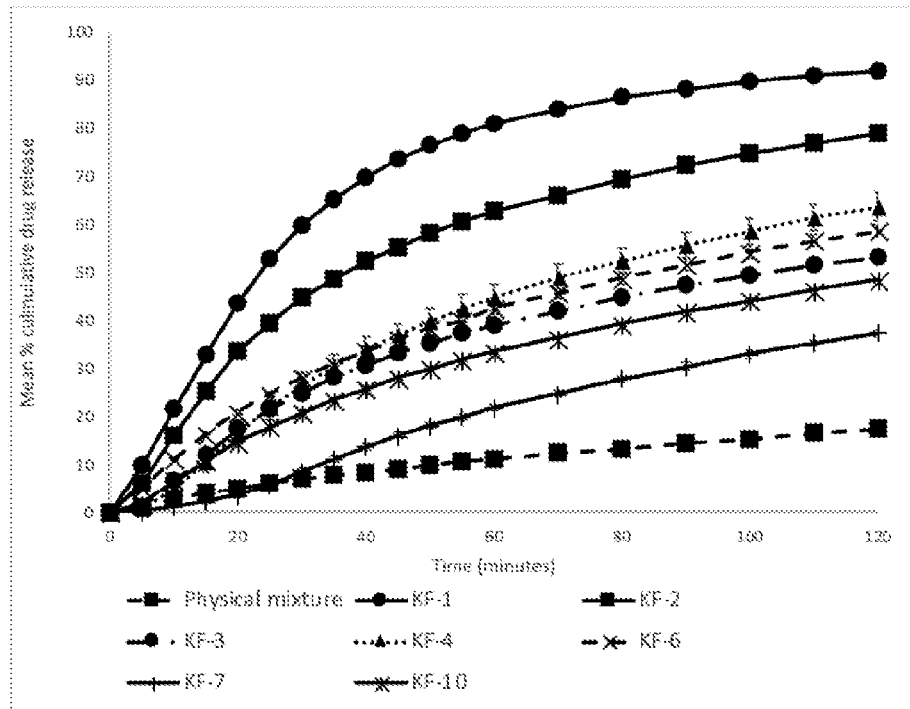
FIG. 24 is a graph showing the dissolution of formulations KF-1 to KF-4, KF-6, KF-7, KF-10 and the physical mixture at pH 1.2.

The dissolution test results at pH1.2 are shown in FIG. 24. In general, the reduction of carrier and coating material reduces the dissolution rate, which could be due to poor disintegration as formulation becomes more cohesive. So KF-1, the formulation with the most carrier and coating material, showed the best dissolution rate, followed by KF-2. Interesting KF-4 showed a better dissolution rate than KF-3. This could be due to KF-4 being subjected to less force during compression stage (500 psi) compared to KF-3 (1400 psi), despite previous studies showing compression force have no effect on dissolution.

Model 2

The key difference between KF-1 and KF-6 is that KF-6 contained more API than KF-1. It is noted that KF-1 shows a much better dissolution rate than KF-6.

Model 3

KF-7 reduces the carrier and coating material and increases the API compared to KF-1 to KF-6. This is effectively a combination of models 1 and 2, and causes a significant reduction in drug dissolution rate. In fact, KF-7 has the slowest drug release after physical mixture tablet.

Model 4

KF-10 reduces the carrier and coating material and increases the API and liquid vehicle compared to KF-1 to KF-6. The introduction of more liquid vehicle improves the dissolution rate, which can be seen when comparing KF-10 with KF-7.

Conclusion

It is possible to apply weight reductions model to further reduce the liqui-tablet weight.

This can be done through reducing carrier and coating materials, increasing the amount of API in the liqui-mass system, or a combination thereof. However, the weight reduction model decreases the drug dissolution rate.

Example 12: Application of Weight Reduction Model Whilst Optimising Ketoprofen Liqui-Tablet to Improve Dissolution Rate The inventors investigated the potential for liqui-tablet of remaining relatively low weight whilst achieving fast dissolution rate.

Materials and Methods

Materials

Ketoprofen was obtained from Tokyo Chemical Industry Co (Japan). Other excipients used to prepare the liqui-tablet included microcrystalline cellulose (avicel PH-102), (FMC corp., UK); colloidal silicon dioxide (aerosil 300), (Evonik Industries AG, Hanau, Germany); synthetic magnesium alumino-metasilicate (Neusilin US2), (Fuji Chemicals, Japan); sodium bicarbonate, (Acros, New Jersey, USA); sodium starch glycolate Type A (primojel); polyethylene glycol 200 (Fisher Scientific, Leicester, UK); propylene glycol (SAFC, Spain); polysorbate 80 (Tween 80), (Acros, Netherlands); sorbitan laurate (Span 80), (Gattefosse, Saint Priest, France) and macrogolglycerol ricinoleate 35 (Kolliphor EL), (BASF SE, Ludwigshafen, Germany). All other reagents and solvent were of analytical grades.

Preparation of Ketoprofen Liqui-Tablet

The preparation of ketoprofen liqui-tablet was carried out in the same manner as Example 10. However, there were variations in the compositions, as shown in table 34.

Table 34a: Key formulation characteristics of extrudate of KLTF-1 to KLTF-10

| Formulation | Water conc in extrudate (% w/w) | Liquid vehicle conc in extrudate (% w/w) | Carrier type | Carrier conc in extrudate (% w/w) | Coating conc in extrudate (% w/w) |
|---|---|---|---|---|---|
| Physical mixture | 49.74 | | 100% avicel PH102 | 31.97 | 1.60 |
| KLTF-1 | 13.42 | 22.37 | 100% avicel PH102 | 40.27 | 2.01 |
| KLTF-2 | 8.97 | 26.96 | 100% avicel PH102 | 31.45 | 1.57 |

-continued

| | | | | | |
|---|---|---|---|---|---|
| KLTF-3 | 12.89 | 25.80 | 50% avicel PH102 & 50% neusilin US2 | 30.09 | 1.50 |
| KLTF-4 | 9.42 | 23.55 | 50 % avicel PH102 & 50% neusilin US2 | 32.97 | 1.65 |
| KLTF-5 | 9.42 | 23.55 | 75% avicel PH102 & 25% neusilin US2 | 32.97 | 1.65 |
| KLTF-6 | 6.76 | 20.31 | 100% avicel PH102 | 23.69 | 1.18 |
| KLTF-7 | 6.32 | 18.96 | 100% avicel PH102 | 22.12 | 1.11 |
| KLTF-8 | 6.54 | 16.31 | 100% avicel PH102 | 22.83 | 1.14 |
| KLTF-9 | 6.32 | 18.96 | 75% avicel PH102 & 25% neusilin US2 | 22.12 | 1.11 |

| Formulation | Primojel conc in extrudate (% w/w) | Sodium bicarbonate conc in extrudate (% w/w) | Ketoprofen conc in extrudate (% w/w) | Successfully spheronized into pellet? (Yes/ No) |
|---|---|---|---|---|
| Physical mixture | 2.49 | | 14.21 | Yes |
| KLTF-1 | 4.03 | | 17.90 | Yes |
| KLTF-2 | 4.09 | | 26.96 | Yes |
| KLTF-3 | 3.91 | | 25.80 | No |
| KLTF-4 | 4.14 | | 28.27 | No |
| KLTF-5 | 4.14 | | 28.27 | Yes |
| KLTF-6 | 4.06 | 23.69 | 20.30 | Yes |
| KLTF-7 | 4.10 | 28.43 | 18.96 | Yes |
| KLTF-8 | 4.24 | 29.36 | 19.58 | Yes |
| KLTF-9 | 4.10 | 28.43 | 18.96 | Yes |

Table 34b: Key formulation characteristics of successfully spheronized formulations after drying and compression force used

| Formulation | Liquid vehicle conc after drying (% w/w) | Carrier type | Carrier conc after drying (% w/w) | Coating conc after drying (% w/w) | Primojel conc after drying (% w/w) |
|---|---|---|---|---|---|
| Physical mixture | | 100% avicel PH102 | 63.6024 | 3.1801221 | 4.9496834 |
| KLTF-1 | 25.84 | 100% avicel PH102 | 46.512 | 2.3257046 | 4.64934184 |
| KLTF-2 | 29.62 | 100% avicel PH102 | 34.5488 | 1.7265533 | 4.48963097 |
| KLTF-5 | 26 | 75% avicel PH102 & 25% neusilin US2 | 36.404 | 1.8192629 | 4.5715611 |
| KLTF-6 | 21.78 | 100% avicel PH102 | 25.4066 | 1.2694607 | 4.35928009 |

-continued

| | | | | | |
|---|---|---|---|---|---|
| KLTF-7 | 20.24 | 100% avicel PH102 | 23.6121 | 1.179898 | 4.37958712 |
| KLTF-8 | 17.45 | 100% avicel PH102 | 24.4327 | 1.2211099 | 4.54093709 |
| KLTF-9 | 20.24 | 75% avicel PH102 & 25% neusilin US2 | 23.6121 | 1.179898 | 4.37958712 |

| Formulation | Sodium bicarbonate conc after drying (% w/w) | Ketoprofen conc after drying (% w/w) | Successfully spheronized into pellet? (Yes/No) | Compression force (PSI) | Total weight of 100 mg ketoprofen liqui-pellet (mg) |
|---|---|---|---|---|---|
| Physical mixture | | 28.2677521 | Yes | 800 | 353.75 |
| KLTF-1 | | 20.6729295 | Yes | 1400 | 483.75 |
| KLTF-2 | | 29.61498 | Yes | 500 | 337.67 |
| KLTF-5 | | 31.2051952 | Yes | 500 | 320.5 |
| KLTF-6 | 25.41 | 21.7746258 | Yes | 500 | 459.17 |
| KLTF-7 | 30.35 | 20.2383878 | Yes | 500 | 494.17 |
| KLTF-8 | 31.41 | 20.9452818 | Yes | 500 | 477.5 |
| KLTF-9 | 30.35 | 20.2383878 | Yes | 500 | 494.17 |

The remaining methods were the same as described in Example 1.

Results and Discussion

Figure 25:
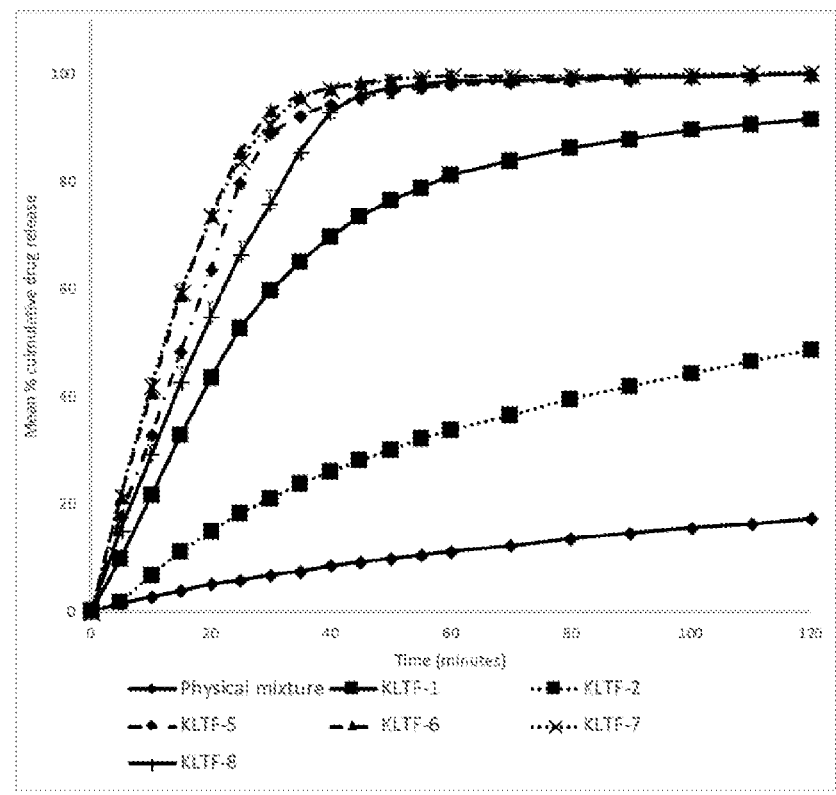
FIG. 25 is a graph showing the dissolution of formulations KLTF-1, KLTF-2, KLTF-5 to KLTF-8 and the physical mixture at pH 1.2.

The dissolution profiles of all successful formulations at pH1.2 are shown in FIG. 25. In comparing KLTF-1 and KLTF-2, it can be seen that the weight reduction model 4 applied in KLTF-2 reduces the dosage form weight considerably, but also reduces the dissolution rate significantly.

The presence of $NaHCO_3$ (effervescent agent) in the liqui-tablet with reduced weight significantly improves the enhancement of drug dissolution rate, see KLTF-5 to KLTF-8.

In comparing formulations KLTF-5 and KLTF-6, where both formulations are similar except KLTF-6 has more $NaHCO_3$ (~25% w/w and 30% w/w respectively), the dissolution profiles are not much different. This indicates that $NaHCO_3$ influence on dissolution rate is reduced as the concentration increase beyond a certain limit. Such observation was also seen in example 5.

Although KLTF-6 shows improved enhanced dissolution rate, the inventor further reduced the weight by reducing liquid vehicle, which is presented in KLTF-7. It can be seen that the liqui-tablet weight is able to reduce whilst not decreasing the dissolution rate. It is noteworthy to mention that KLTF-7 is only 494.17 mg, which is not heavy in terms of tablet. Yet the dose is high (100 mg) relative to liquisolid technology. Hence, there is potential for further improvement of drug release through additional or increase in functional excipient, increasing carrier & coating material or reducing API in the liqui-mass system.

Conclusion

The inventors are able to apply weight reduction models to high dose liqui-tablet, whilst improving the drug dissolution rate. This shows that the technology is capable of reducing dosage form weight and maintain fast drug release.

Example 13: Improving the Flow Property of Pre-Compressed Ketoprofen Liqui-Tablet Using Anti-Tack Agents The inventors investigated the potential for resolving or improving pre-compressed liqui-tablet (or liqui-pellet) flow properties using an anti-tack agent. This is to counter potential issues with flow properties for sticky pellets with a very high liquid vehicle content.

Materials and Methods

Materials

Ketoprofen was obtained from Tokyo Chemical Industry Co (Japan). Other excipients used to prepare the liqui-tablet included microcrystalline cellulose (avicel PH-102), (FMC corp., UK); magnesium stearate; colloidal silicon dioxide (aerosil 300), (Evonik Industries AG, Hanau, Germany); colloidal silicon dioxide (aerosil 200), (Evonik Industries AG, Hanau, Germany); sodium bicarbonate, (Acros, New Jersey, USA); sodium starch glycolate Type A (primojel); and polyethylene glycol 200 (Fisher Scientific, Leicester, UK). All other reagents and solvent were of analytical grades.

Preparation of Ketoprofen Liqui-Tablet

The preparation of ketoprofen liqui-tablet was carried out in the same manner as Example 10. However, there were variations in the compositions and compression force used, as shown in table 35. Additionally, formulations that incorporated anti-tack agent were prepared as described in Example 10, and after pelletisation the anti-tack agent was disposed in a sealed glass bottle with the pelletised formulation, and the bottle was inverted 20 times. The sample was then sieved to remove the excess anti-tack agent. The amount of anti-tack agent incorporated was determined by weighing the sample before and after the incorporation of anti-tack agent.

The physical mixture pellet was prepared in a similar manner as above, but without liquid vehicle incorporated. All formulations' carrier to coating material ratio were kept constant at 20:1 respectively.

TABLE 35

Key formulation characteristics of F-1a to F-7a

| Formulation | Liquid vehicle conc. after drying (% w/w) | Liquid load factor | Carrier conc. after drying (% w/w) | Coating conc. after drying (% w/w) | Primojel conc. after drying (% w/w) | NaHCO$_3$ conc. after drying (% w/w) |
|---|---|---|---|---|---|---|
| Physical mixture pellet 11 | | | 63.6 | 3.18 | 4.95 | 0 |
| F-1a | 11.26 | 1.28 | 26.27 | 1.31 | 4.33 | 33.77 |
| F-2a | 14.47 | 1.43 | 25.32 | 1.27 | 4.02 | 32.55 |
| F-3a | 17.45 | 1.57 | 24.43 | 1.22 | 3.75 | 31.41 |
| F-4a | 11.19 | 1.28 | 25.86 | 1.29 | 4.31 | 33.56 |
| F-5a | 14.39 | 1.43 | 25.04 | 1.25 | 4.01 | 32.39 |
| F-6a | 17.34 | 1.57 | 24.14 | 1.21 | 3.73 | 31.21 |
| F-7a | 17.23 | 1.57 | 23.64 | 1.18 | 3.71 | 31.01 |

| Formulation | Type of anti-tack agent | Amount of anti-tack agent after drying (% w/w) | Ketoprofen conc. after drying (% w/w) | Total weight of 100 mg ketoprofen liqui-pellet (mg) | Compression force (PSI) | Amount of pre-extrusion liquid during extrusion-spheronization (ml) per 20 g of admixture of API and excipients |
|---|---|---|---|---|---|---|
| Physical mixture pellet | | | 28.27 | 353.75 | 800 | 19.79 |
| F-1a | | | 22.51 | 444.2 | 1000 | 2.25 |
| F-2a | | | 21.7 | 460.8 | 1000 | 2.17 |
| F-3a | | | 20.94 | 477.5 | 1000 | 1.4 |
| F-4a | Magnesium stearate | 0.63 | 22.16 | 451.2 | 1500 | 2.24 |
| F-5a | Magnesium stearate | 0.5 | 21.46 | 466 | 1500 | 2.16 |
| F-6a | Magnesium stearate | 0.66 | 20.69 | 483.4 | 1500 | 1.39 |
| F-7a | Aerosil 200 | 1.25 | 20.26 | 493.5 | 1500 | 1.38 |

Formulations F-1a to F-3a were used to investigate the physicochemical properties (particularly flow property) on varying liquid vehicle concentration. Formulations F-4a to F-6a were mainly used to observe the influence of magnesium stearate (anti-tack agent) influence on flow properties. Formulation F-7a used silicone dioxide (Aerosil 200) anti-tack agent to observe its influence on flow properties.

Results and Discussion

Flow Properties of Ketoprofen Pre-Compressed Liqui-Tablet

The flow properties are summarised in Table 36.

TABLE 36

Results of flowability studies

| Formulation | Flow Rate (g/sec) ± SD | Angle of repose ± SD | CI % ± SD | Inference according to Angle of repose | Inference according to CI % |
|---|---|---|---|---|---|
| Physical mixture pellet | 9.4 ± 0.36 | 20.52 ± 3.18 | 10.56 ± 0.00 | Excellent flowability | Excellent-good flowability |
| F-1a | 7.41 ± 0.72 | 23.28 ± 0.78 | 12.36 ± 2.15 | Excellent flowability | Good flowability |
| F-2a | 7.87 ± 0.71 | 22.79 ± 3.10 | 6.89 ± 0.00 | Excellent flowability | Excellent flowability |
| F-3a | | 26.20 ± 1.09 | | Excellent flowability | |
| F-4a | 9.48 ± 0.46 | 20.83 ± 0.72 | 10.63 ± 0.00 | Excellent flowability | Excellent-good flowability |

TABLE 36-continued

Results of flowability studies

| Formulation | Flow Rate (g/sec) ± SD | Angle of repose ± SD | CI % ± SD | Inference according to Angle of repose | Inference according to CI % |
|---|---|---|---|---|---|
| F-5a | 10.45 ± 0.24 | 18.6 ± 0.43 | 12.49 ± 0.00 | Excellent flowability | Good flowability |
| F-6a | 10.09 ± 0.16 | 19.17 ± 0.44 | 10.23 ± 0.00 | Excellent flowability | Excellent-good flowability |
| F-7a | 7.57 ± 0.41 | 21.08 ± 0.43 | 12.54 ± 0.00 | Excellent flowability | Good flowability |

With the exception of formulation F-3a, there is no issue with flow properties. Formulations F-1a to F-3a have different concentrations of PEG 200, with F-3a having the highest among these three formulations. This large amount of liquid vehicle gave rise to sticky liqui-pellet, such that flow rate test and CI test were inapplicable. Although the angle of repose for F-3a indicates excellent flowability, this is only true once the liqui-pellet start flowing. Initially a slight agitation may be required to trigger the flow.

Formulations F-4a to F-6a are the same as F-1a to F-3a (respectively), except F-4a to F-6a have magnesium stearate, an anti-tack agent, incorporated therein. It is clear from the data that an anti-tack agent can improve flow properties. In particular, the incorporation of magnesium stearate into F-6a overcame the cohesive issue observed for formulation F-3a.

Formulation F-7a is the same as F-3a except Aerosil 200, an alternative anti-tack agent, has been incorporated therein. The results show that Aerosil can also act as an anti-tack agent and improve flow properties.

Surface Analysis of Pre-Compressed Liqui-Tablet Using Digital Microscope Analysis The inventors conducted analysis of images obtained using a digital microscope for the pre-compressed liqui-tablet (liqui-pellet) formulations of F-3a, F-6a and F-7a. The inventors noted that formulations magnesium stearate and Aerosil 200 can be seen on the surface of the pellets of F-6a and F-7a, respectively. For formulation F-6 the magnesium stearate was concentrated in the gaps of the imperfect spherical pellet.

However, in F-7, the Aerosil 200 seemed to comprise a thicker layer of covering of the pellet. It is reasonable to postulate that Aerosil 200 anti-tack agent has thicker layer due to its unique nano-sized range. Nano-particle are usually more cohesive than coarser particles due to a higher area to volume ratio, thus, Aerosil 200 would adhere to the pellet and cohere to other adjacent Aerosil 200 extensively, forming a layer around the pellet.

This shows that depending on the physico-chemical properties of the anti-tack agent, it may coat the pellet with a different degree. A desired anti-tack agent can be selected for different formulations.

In-Vitro Drug Release Test

Figure 26:
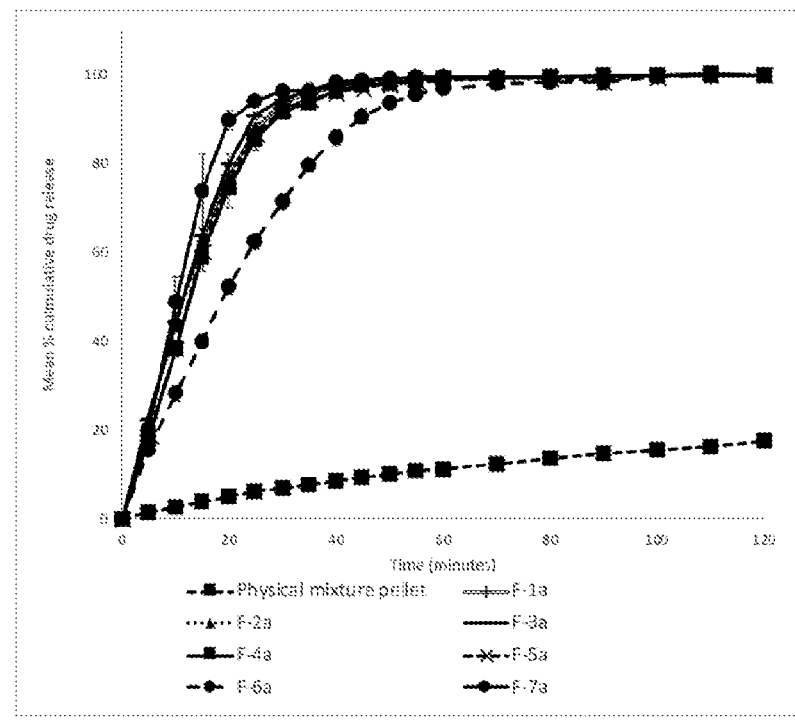
FIG. 26 is a graph showing the dissolution of formulations F-1a to F-7a and the physical mixture at pH 1.2.

The dissolution profile of all formulations is shown in FIG. 26. Formulations F-1a, F-2a and F-3a have very similar dissolution profiles, which means that the lowest concentration of PEG 200 in F-1 is already nearing or is at the optimal concentration for enhanced Ketoprofen release formulation. But for the purpose of making cohesive pellet, F-2 and F-3 were included with higher PEG 200 concentration.

The incorporation of magnesium stearate in formulations F-4a and F-5a had a negligible effect on the dissolution profiles when compared to formulations F-1a and F-2a, respectively. However, the drug release rate of formulation F-6a is significantly slower than F-3a. The higher degree of magnesium stearate incorporated in F-6a may have reached a threshold that results in retardation of drug release. Conversely, formulation F-7a, which incorporated Aerosil 200 had a slightly improved drug release rate when compared to formulation F-3a.

Conclusion

The inventors have shown that for compositions comprising higher proportions a liquid vehicle, flowability issues can be overcome using an anti-tack agent. Furthermore, different anti-tack agents have different physicochemical properties that can influence liqui-tablet (and liqui-pellet) drug release rate. In particular, hydrophilic anti-tack agents such as, Aerosil 200, can enhance drug release rate.

Example 14: Producing Sustained Release Propranolol Liqui-Tablet Through Matrix System Approach, Using Eudragit Retarding Agent The examples above describe the production of fast release formulations. The present example aims to investigate the potential for incorporating the liqui-pellet system into a sustained release formulation.

Materials and Methods

Materials

Propranolol was obtained from Tokyo Chemical Industry Co (Japan). Other excipients used to prepare the liqui-tablet included microcrystalline cellulose (avicel PH-102), (FMC corp., UK); Eudragit RS PO; colloidal silicon dioxide (aerosil 300), (Evonik Industries AG, Hanau, Germany); colloidal silicon dioxide (aerosil 200), (Evonik Industries AG, Hanau, Germany); polysorbate 80 (Tween 80), (Acros, Netherlands); polysorbate 20 (Tween 20), (Acros, Netherlands); and macrogolglycerol ricinoleate 35 (Kolliphor EL), (BASF SE, Ludwigshafen, Germany). All other reagents and solvent were of analytical grades.

Preparation of Propranolol Liqui-Tablet

The liqui-tablet formulations were prepared via compressing liqui-pellets under specified compression force using a manual tablet press machine (Compaction model MTCM-I, Globe pharma, UK). All liqui-pellet formulations were produced in a similar manner except for the variation in parameters such as: type of liquid vehicle, concentration of liquid vehicle, water content, presence or absence of Eudragit RS PO and ratio of binary mixture of carriers as shown in Table 37. The liquid medication was prepared by mixing propranolol and a specified liquid vehicle using pestle and mortar. This mixture was then incorporated into avicel PH 102 (carrier material) and Eudragit RS PO, in formulations where this was present. The admixture was mixed for 2 min at a constant rate of 125 rpm (Caleva Multitab, Caleva Process Solutions Ltd, UK). A specified amount of deionized water (granulating liquid) was added bit by bit to achieve reasonable plastic property for extrusion (Caleva Multitab, Caleva Process Solutions Ltd, UK). The admixture with water was mixed for 5 min, then Aerosil 300 (coating material) was added and further mixed for another 5 min before extrusion. Once the sample was extruded, the extrudates were spheronized at an almost constant rotation at 4000 rpm (decrease to 2000 rpm if agglomeration seemed likely). The spheronization time varied depending on the extrudates' plastic property to avoid agglomeration. The pellets were then placed in an oven under a constant temperature of 40° C. overnight to remove the water content.

The physical mixture pellet was prepared in a similar manner as above, but without liquid vehicle incorporated and Eudragits RS PO added. All formulations' carrier to coating material ratio were kept constant at 20:1 respectively.

TABLE 37

Key formulation characteristics of F-1b to F-8b

| Formulation | Liquid vehicle | Liquid vehicle conc. after drying (% w/w) | Liquid load factor | Carrier conc. after drying (% w/w) | Coating conc. after drying (% w/w) |
|---|---|---|---|---|---|
| Physical mixture pellet | | | | 66.91 | 3.35 |
| F-1b | Tween 80 | 12.94 | 0.67 | 58.25 | 2.91 |
| F-2b | Tween 20 | 12.94 | 0.67 | 58.25 | 2.91 |
| F-3b | Kolliphor EL | 12.94 | 0.67 | 58.25 | 2.91 |
| F-4b | Tween 20 | 18.24 | 0.78 | 54.71 | 2.74 |
| F-5b | Tween 20 | 22.92 | 0.89 | 51.58 | 2.58 |
| F-6b | Tween 20 | 18.24 | 0.78 | 41.03 | 2.74 |
| F-7b | Tween 20 | 18.24 | 0.78 | 27.36 | 2.74 |
| F-8b | Tween 20 | 18.24 | 0.78 | 13.68 | 2.74 |

| Formulation | Amount of Eudragit RS PO after drying (% w/w) | Propranolol conc. after drying (% w/w) | Total weight of 80 mg propranolol liqui-pellet (mg) | Compression force (PSI) | Amount of pre-extrusion liquid during extrusion-spheronization (ml) per 20 g of admixture of API and excipients |
|---|---|---|---|---|---|
| Physical mixture pellet | | 29.74 | 269 | 1000 | 22.3 |
| F-1b | | 25.89 | 309 | 1400 | 12.9 |
| F-2b | | 25.89 | 309 | 1400 | 12.9 |
| F-3b | | 25.89 | 309 | 1400 | 12.9 |
| F-4b | | 24.32 | 329 | 1400 | 12.2 |
| F-5b | | 22.92 | 349 | 1400 | 11.5 |
| F-6b | 13.68 | 24.32 | 329 | 1400 | 9.7 |
| F-7b | 27.36 | 24.32 | 329 | 1400 | 4.9 |
| F-8b | 41.03 | 24.32 | 329 | 1400 | 3.0 |

Results and Discussion
Saturation Solubility Test
The data from the saturation solubility test is provided in table 38.

TABLE 38

Solubility of Propranolol in various solvents at 37° C. (n = 3)

| Solvent | Mean concentration (mg/ml) ± SD | Inference |
|---|---|---|
| Tween 80 | 1.89 ± 0.01 | Slightly soluble |
| Tween 20 | 1.86 ± 0.00 | Slightly soluble |
| Kolliphor EL | 1.32 ± 0.00 | Slightly soluble |
| Water | 29.03 ± 0.12 | Sparingly soluble |

This data clearly shows that propranolol is less soluble in non-volatile liquid vehicles than water.

Flowability Test on Pre-Compressed Propranolol Liqui-Tablet

The flow properties are summarised in Table 39.

TABLE 39

Results of flowability studies

| Formulation | Flow Rate (g/sec) ± SD | Angle of repose ± SD | CI % ± SD | Inference according to Angle of repose | Inference according to CI % |
|---|---|---|---|---|---|
| Physical mixture tablet | 6.86 ± 0.31 | 24.48 ± 1.17 | 16.17 ± 0.00 | Excellent flowability | Fair flowability |
| F-1b | 8.50 ± 0.14 | 20.77 ± 0.14 | 12.56 ± 2.06 | Excellent flowability | Good flowability |
| F-2b | 8.17 ± 0.35 | 22.94 ± 0.65 | 13.53 ± 0.00 | Excellent flowability | Good flowability |
| F-3b | 7.86 ± 0.33 | 22.79 ± 0.81 | 12.50 ± 0.00 | Excellent flowability | Good flowability |
| F-4b | 6.50 ± 0.03 | 26.82 ± 0.88 | 13.86 ± 0.00 | Excellent flowability | Good flowability |
| F-5b | 6.80 ± 0.32 | 23.39 ± 0.39 | 6.47 ± 0.00 | Excellent flowability | Excellent flowability |
| F-6b | 6.44 ± 0.13 | 24.84 ± 1.14 | 12.79 ± 0.00 | Excellent flowability | Good flowability |
| F-7b | 7.28 ± 0.21 | 24.11 ± 0.88 | 12.26 ± 0.00 | Excellent flowability | Good flowability |
| F-8b | 7.04 ± 0.144 | 24.51 ± 0.74 | 11.84 ± 0.00 | Excellent flowability | Good flowability |

The data provided above shows that no flowability issues were observed,

Particle Size Analysis Via Sieve Method

Data from particle size analysis show all pre-compressed liqui-tablet formulation have narrow size distribution.

Friability Test

The results of friability tests are provided in Table 40.

TABLE 40

Results of friability tests

| Formulation | % weight loss | Fractured (Yes/No) | Passed/Failed |
|---|---|---|---|
| Physical mixture tablet | | Yes | Failed |
| F-1b | 0 | | Passed |
| F-2b | 0 | | Passed |
| F-3b | 0.08 | | Passed |
| F-4b | 0 | | Passed |
| F-5b | | Yes | Failed |
| F-6b | 0 | | Passed |
| F-7b | 0 | | Passed |
| F-8b | 0 | | Passed |

All formulation passed the friability test except for physical mixture tablet and F-5b. Formulation F-5b had the highest amount of liquid vehicle which may have contributed to a reduction in robustness, causing F-5b to fracture.

In-Vitro Drug Release Test

Figure 27:
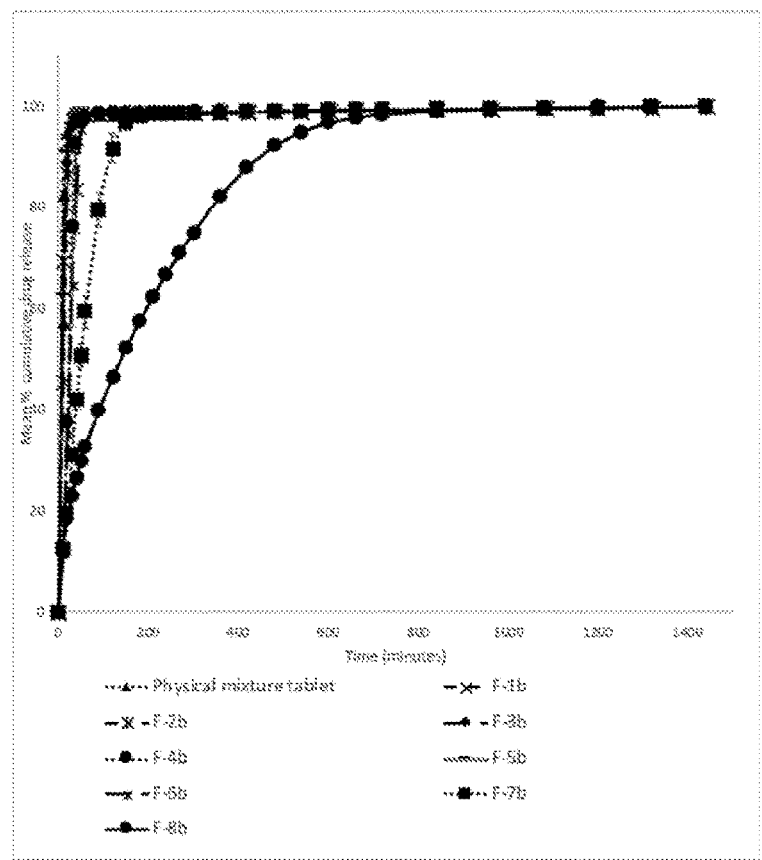
FIG. 27 is a graph showing the dissolution of formulations F-1b to F-8b and the physical mixture at pH 1.2.
Figure 28:
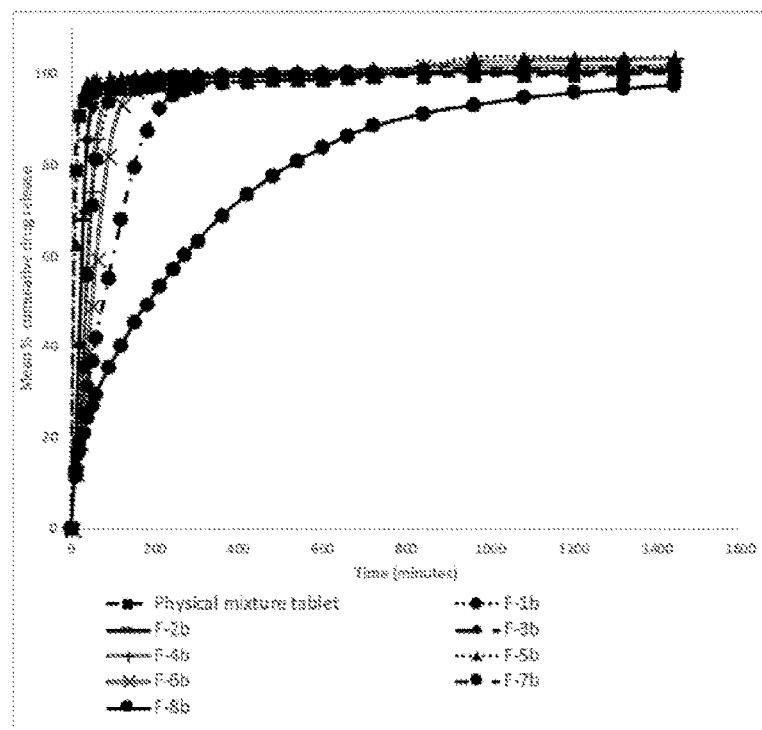
FIG. 28 is a graph showing the dissolution of formulations F-1b to F-8b and the physical mixture at pH 7.4.

Data from drug dissolution tests is shown in FIGS. 27 and 28 and verifies that it is possible to make sustained release propranolol liqui-tablet formulation. In particular, formulation F-8b has the best sustained drug release rate, due to the high amount of Eudragit RS PO in the formulation. It is noted that the use of Eudragit RS PO did not cause issues in production.

Conclusion

It is possible to make sustained release liqui-tablet (and liqui-pellet) formulation with the use of suitable liquid vehicles and retarding agents.

The invention claimed is:

1. A method of producing a pharmaceutical composition, the method comprising:
   dissolving an active pharmaceutical ingredient (API) in a liquid vehicle to form a liquid medicament;
   contacting the liquid medicament with a pharmaceutical carrier such that the liquid load factor of the resultant composition is at least 0.5, wherein the liquid load factor is calculated as being the weight of the liquid medication divided by the weight of the carrier powder;
   contacting the composition comprising the liquid medicament and pharmaceutical carrier with a pharmaceutical coating material having a Brunauer-Emmett-Teller (BET) specific surface area of at least 10 m²/g to form a liqui-mass composition, wherein the weight ratio of the carrier to the coating material is between 30:1 and 2:1; and pelletising the liqui-mass composition to form the pharmaceutical composition.

2. A method according to claim 1, wherein the amount of the API used is sufficient to cause the liqui-mass composition to comprise between 1 wt % and 60 wt % API, between 2 wt % and 50 wt % API, between 3 wt % and 35 wt % API, between 4 wt % and 25 wt % API or between 5 wt % and 20 wt % API.

3. A method according to claim 1, wherein the liquid vehicle comprises a non-volatile organic solvent.

4. A method according to claim 1, wherein the amount of the liquid vehicle used is sufficient to cause the liqui-mass composition to comprise between 5 wt % and 50 wt % liquid vehicle, between 10 wt % and 45 wt % liquid vehicle, between 15 wt % and 40 wt % liquid vehicle, or between 20 wt % and 35 wt % liquid vehicle.

5. A method according to claim 1, wherein the method further comprises contacting the liquid medicament, the composition comprising the liquid medicament and pharmaceutical carrier, the liqui-mass composition and/or the pelletised liqui-mass composition with one or more additional excipients.

6. A method according to claim 5, wherein the additional excipient comprises a disintegrant, optionally wherein the disintegrant is a superdisintegrant and comprises starch glycolate, polyvinylpolypyrrolidone (PVPP), croscarmellose, chitin-silica, chitosan-silica, indion 414, or mucilage of *Plantago ovate*, or a pharmaceutically acceptable salt thereof and/or wherein the amount of disintegrant used is sufficient to cause the liqui-mass composition to comprise between 1 wt % and 15 wt % disintegrant.

7. A method according to claim 5, wherein the one or more additional excipients comprise an effervescent agent, optionally wherein the amount of effervescent agent used is sufficient to cause the liqui-mass composition to comprise between 1 wt % and 60 wt % effervescent agent.

8. A method according claim 5, wherein the one or more additional excipients comprise a retarding agent, optionally wherein the retarding agent is a polymer configured to sustainably release the API.

9. A method according to claim 5, wherein the one or more additional excipient comprise an anti-tack agent.

10. A method according to claim 1, wherein the pharmaceutical carrier comprises cellulose and a material with a large BET specific surface area, wherein the material with a large BET specific surface area has a BET specific surface area of at least 10 m²/g.

11. A method according to claim 10, wherein the material with the large BET specific surface area comprises magnesium aluminometasilicate or calcium phosphate and/or wherein the weight ratio of cellulose to the material with the large BET specific surface area is between 1:99 and 99:1.

12. A method according to claim 1, wherein the amount of the carrier used is sufficient to cause the liqui-mass composition to comprise between 5 wt % and 60 wt % carrier, between 10 wt % and 55 wt % carrier, between 15 wt % and 50 wt % carrier, or between 20 wt % and 45 wt % carrier.

13. A method according to claim 1, wherein the weight ratio of the carrier to the coating material is between 25:1 and 4:1, or between 20:1 and 5:1.

14. A method according to claim 1, wherein the method further comprises contacting the composition comprising the liquid medicament and pharmaceutical carrier with a granulating liquid, optionally wherein the composition comprising the liquid medicament and pharmaceutical carrier is contacted with a granulating liquid before the composition has been contacted with a pharmaceutical coating, optionally wherein the method comprises drying the pharmaceutical composition.

15. A method according to claim 14, wherein the granulating liquid comprises water, alcohol and/or polyethylene glycol (PEG) and/or wherein the amount of the granulating liquid used is sufficient to cause the liqui-mass composition to comprise at between 1 wt % and 50 wt % granulating liquid.

16. A method according to claim 1, wherein the method further comprises compressing the pharmaceutical composition into a tablet.

17. A pharmaceutical composition comprising a plurality of pellets or granules comprising an active pharmaceutical ingredient (API), a liquid vehicle, a pharmaceutical carrier and a pharmaceutical coating material, wherein the composition has a liquid load factor of at least 0.5, wherein the liquid load factor is calculated as being the weight of the liquid medication divided by the weight of the carrier powder, and the pharmaceutical coating material has a Brunauer-Emmett-Teller (BET) specific surface area of at least 10 m²/g.

18. A pharmaceutical composition comprising an active pharmaceutical ingredient (API), a liquid vehicle, a pharmaceutical carrier and a pharmaceutical coating material, wherein the composition has a liquid load factor of at least 1, wherein the liquid load factor is calculated as being the weight of the liquid medication divided by the weight of the carrier powder, and the pharmaceutical coating material has a Brunauer-Emmett-Teller (BET) specific surface area of at least 10 m²/g.

19. A tablet comprising an active pharmaceutical ingredient (API), a liquid vehicle, a pharmaceutical carrier and a pharmaceutical coating material, wherein the composition has a liquid load factor of at least 0.5, wherein the liquid load factor is calculated as being the weight of the liquid medication divided by the weight of the carrier powder, and the pharmaceutical coating material has a Brunauer-Emmett-Teller (BET) specific surface area of at least 10 m²/g.

20. The method according to claim 1, wherein the composition comprising the liquid medicament and pharmaceutical carrier has a liquid load factor of at least 1.

21. The method according to claim 1, wherein the liqui-mass composition comprises less than 15 wt % disintegrant.

* * * * *